US012747467B2

(12) United States Patent
Chee

(10) Patent No.: US 12,747,467 B2
(45) **Date of Patent: *Sep. 29, 2026**

(54) SPATIALLY ENCODED BIOLOGICAL ASSAYS

(71) Applicant: Prognosys Biosciences, Inc., San Diego, CA (US)

(72) Inventor: Mark S. Chee, San Diego, CA (US)

(73) Assignee: Prognosys Biosciences, Inc.

( * ) Notice: Subject to any disclaimer, the term of this patent is extended or adjusted under 35 U.S.C. 154(b) by 921 days.

This patent is subject to a terminal disclaimer.

(21) Appl. No.: 18/100,127

(22) Filed: Jan. 23, 2023

(65) Prior Publication Data

US 2023/0332211 A1 Oct. 19, 2023

Related U.S. Application Data

(63) Continuation of application No. 17/878,519, filed on Aug. 1, 2022, now Pat. No. 11,560,587, which is a continuation of application No. 17/556,588, filed on Dec. 20, 2021, now Pat. No. 11,401,545, which is a continuation of application No. 17/223,669, filed on Apr. 6, 2021, now Pat. No. 11,208,684, which is a continuation of application No. 17/030,230, filed on Sep. 23, 2020, now Pat. No. 11,384,386, which is a continuation of application No. 16/988,284, filed on Aug. 7, 2020, now Pat. No. 10,961,566, which is a continuation of application No. 16/414,213, filed on May 16, 2019, now Pat. No. 10,787,701, which is a continuation of application No. 16/402,098, filed on May 2, 2019, now Pat. No. 10,472,669, which is a continuation of application No. 16/276,235, filed on Feb. 14, 2019, now Pat. No. 10,480,022, which is a continuation of application No. 15/187,661, filed on (Continued)

(51) Int. Cl.

| | |
|---|---|
| ***C12Q 1/6837*** | (2018.01) |
| ***B01L 3/00*** | (2006.01) |
| ***C12Q 1/68*** | (2018.01) |
| ***C12Q 1/6804*** | (2018.01) |
| ***C12Q 1/6809*** | (2018.01) |
| ***C12Q 1/6834*** | (2018.01) |
| ***C12Q 1/6841*** | (2018.01) |
| ***C12Q 1/6858*** | (2018.01) |
| ***C12Q 1/6869*** | (2018.01) |
| ***C12Q 1/6874*** | (2018.01) |
| ***C12Q 1/6876*** | (2018.01) |
| ***C40B 30/04*** | (2006.01) |
| ***C40B 60/04*** | (2006.01) |
| ***G01N 33/53*** | (2006.01) |
| ***G01N 33/543*** | (2006.01) |
| ***G01N 33/68*** | (2006.01) |

(52) U.S. Cl.

CPC ...... *C12Q 1/6837* (2013.01); *B01L 3/502715* (2013.01); *C12Q 1/68* (2013.01); *C12Q 1/6804* (2013.01); *C12Q 1/6809* (2013.01); *C12Q 1/6834* (2013.01); *C12Q 1/6841* (2013.01); *C12Q 1/6869* (2013.01); *C12Q 1/6874* (2013.01); *C12Q 1/6876* (2013.01); *C40B 30/04* (2013.01); *C40B 60/04* (2013.01); *G01N 33/5308* (2013.01); *G01N 33/543* (2013.01); *G01N 33/54366* (2013.01); *G01N 33/6845* (2013.01); *G01N 33/6848* (2013.01); *C12Q 1/6858* (2013.01); *C12Q 2600/156* (2013.01); *C12Q 2600/158* (2013.01); *G01N 2458/10* (2013.01); *G01N 2458/40* (2013.01)

(58) Field of Classification Search

CPC ... B01L 3/502715; C12Q 1/68; C12Q 1/6804; C12Q 1/6809; C12Q 1/6834; C12Q 1/6837; C12Q 1/6841; C12Q 1/6869; C12Q 1/6874; C12Q 1/6876; C12Q 2600/156; C12Q 2600/158; C12Q 2535/122; C12Q 2543/10; C12Q 2563/179; C12Q 2565/515; C12Q 2565/507; C12Q 2565/513; C40B 30/04; C40B 60/04; G01N 33/5308; G01N 33/543; G01N 33/54366; G01N 33/6845; G01N 33/6848; G01N 2458/10

See application file for complete search history.

(56) References Cited

U.S. PATENT DOCUMENTS

| | | | |
|---|---|---|---|
| 4,514,388 | A | 4/1985 | Psaledakis |
| 4,557,903 | A | 12/1985 | McCormick |

(Continued)

FOREIGN PATENT DOCUMENTS

| | | |
|---|---|---|
| AU | 2003200718 | 10/2006 |
| CA | 2169928 | 4/2007 |

(Continued)

OTHER PUBLICATIONS

Almog et al., "The crystal structures of the psychrophilic subtilisin S41 and the mesophilic subtilisin Sph reveal the same calcium-loaded state," Proteins, Feb. 1, 2009, 74(2):489-496.

(Continued)

*Primary Examiner* — Jeremy C Flinders
(74) *Attorney, Agent, or Firm* — Fish & Richardson P.C.

(57) ABSTRACT

The present invention provides assays and assay systems for use in spatially encoded biological assays. The invention provides an assay system comprising an assay capable of high levels of multiplexing where reagents are provided to a biological sample in defined spatial patterns; instrumentation capable of controlled delivery of reagents according to the spatial patterns; and a decoding scheme providing a readout that is digital in nature.

20 Claims, 5 Drawing Sheets

Related U.S. Application Data

Jun. 20, 2016, now Pat. No. 10,308,982, which is a continuation of application No. 13/080,616, filed on Apr. 5, 2011, now Pat. No. 9,371,598.

(60) Provisional application No. 61/321,124, filed on Apr. 5, 2010.

(56) References Cited

U.S. PATENT DOCUMENTS

| | | | |
|---|---|---|---|
| 4,574,729 | A | 3/1986 | Wells |
| 4,683,195 | A | 7/1987 | Mullis |
| 4,683,202 | A | 7/1987 | Mullis |
| 4,731,335 | A | 3/1988 | Brigati |
| 4,800,159 | A | 1/1989 | Mullis |
| 4,829,012 | A | 5/1989 | Cambiaso et al. |
| 4,883,867 | A | 11/1989 | Lee |
| 4,965,188 | A | 10/1990 | Mullis |
| 4,968,601 | A | 11/1990 | Jacobson et al. |
| 4,988,617 | A | 1/1991 | Landegren et al. |
| 5,002,882 | A | 3/1991 | Lunnen |
| 5,061,049 | A | 10/1991 | Hornbeck |
| 5,130,238 | A | 7/1992 | Malek |
| 5,183,053 | A | 2/1993 | Yeh et al. |
| 5,308,751 | A | 5/1994 | Ohkawa |
| 5,321,130 | A | 6/1994 | Yue |
| 5,410,030 | A | 4/1995 | Yue |
| 5,436,129 | A | 7/1995 | Stapleton |
| 5,436,134 | A | 7/1995 | Haugland |
| 5,455,166 | A | 10/1995 | Walker |
| 5,472,881 | A | 12/1995 | Beebe et al. |
| 5,487,972 | A | 1/1996 | Gelfand et al. |
| 5,494,810 | A | 2/1996 | Barany et al. |
| 5,496,518 | A | 3/1996 | Arai et al. |
| 5,503,980 | A | 4/1996 | Cantor |
| 5,512,439 | A | 4/1996 | Hornes |
| 5,512,462 | A | 4/1996 | Cheng |
| 5,512,478 | A | 4/1996 | Orser et al. |
| 5,543,291 | A | 8/1996 | Keyomarsi et al. |
| 5,559,032 | A | 9/1996 | Porneroy |
| 5,578,467 | A | 11/1996 | Schuster et al. |
| 5,582,977 | A | 12/1996 | Yue |
| 5,589,173 | A | 12/1996 | O'Brien |
| 5,599,675 | A | 2/1997 | Brenner |
| 5,610,287 | A | 3/1997 | Nikiforov et al. |
| 5,641,658 | A | 6/1997 | Adams |
| 5,648,245 | A | 7/1997 | Fire et al. |
| 5,658,751 | A | 8/1997 | Yue |
| 5,667,976 | A | 9/1997 | Van Ness et al. |
| 5,672,344 | A | 9/1997 | Kelley et al. |
| 5,695,940 | A | 12/1997 | Drmanac et al. |
| 5,716,825 | A | 2/1998 | Hancock et al. |
| 5,750,333 | A | 5/1998 | Clark |
| 5,750,341 | A | 5/1998 | Macevicz |
| 5,752,982 | A | 5/1998 | Lang et al. |
| 5,763,175 | A | 6/1998 | Brenner |
| 5,807,522 | A | 9/1998 | Brown et al. |
| 5,817,783 | A | 10/1998 | Calabretta et al. |
| 5,830,711 | A | 11/1998 | Barany et al. |
| 5,837,832 | A | 11/1998 | Chee et al. |
| 5,837,860 | A | 11/1998 | Anderson et al. |
| 5,854,033 | A | 12/1998 | Lizardi |
| 5,863,753 | A | 1/1999 | Haugland |
| 5,866,377 | A | 2/1999 | Kim et al. |
| 5,871,921 | A | 2/1999 | Landegren et al. |
| 5,875,258 | A | 2/1999 | Ortyn et al. |
| 5,912,148 | A | 6/1999 | Eggerding |
| 5,919,626 | A | 7/1999 | Shi et al. |
| 5,925,545 | A | 7/1999 | Reznikoff et al. |
| 5,928,906 | A | 7/1999 | Koester et al. |
| 5,958,775 | A | 9/1999 | Wickstrom et al. |
| 5,962,271 | A | 10/1999 | Chenchik et al. |
| 5,962,272 | A | 10/1999 | Chenchik et al. |
| 5,965,443 | A | 10/1999 | Reznikoff et al. |
| 5,994,136 | A | 11/1999 | Naldini et al. |
| 6,013,440 | A | 1/2000 | Lipshutz |
| 6,013,516 | A | 1/2000 | Verma et al. |
| 6,017,923 | A | 1/2000 | Sabol |
| 6,027,889 | A | 2/2000 | Barany et al. |
| 6,054,274 | A | 4/2000 | Sampson et al. |
| 6,060,240 | A | 5/2000 | Kamb et al. |
| 6,083,761 | A | 7/2000 | Kedar et al. |
| 6,130,073 | A | 10/2000 | Eggerding |
| 6,133,436 | A | 10/2000 | Koester et al. |
| 6,136,592 | A | 10/2000 | Leighton |
| 6,143,496 | A | 11/2000 | Brown |
| 6,153,389 | A | 11/2000 | Haarer |
| 6,153,408 | A | 11/2000 | Abastado et al. |
| 6,157,432 | A | 12/2000 | Helbing |
| 6,159,736 | A | 12/2000 | Reznikoff et al. |
| 6,165,714 | A | 12/2000 | Lane et al. |
| 6,172,218 | B1 | 1/2001 | Brenner |
| 6,210,891 | B1 | 4/2001 | Nyren |
| 6,210,894 | B1 | 4/2001 | Brennan |
| 6,214,587 | B1 | 4/2001 | Dattagupta |
| 6,221,591 | B1 | 4/2001 | Aerts |
| 6,221,654 | B1 | 4/2001 | Quake |
| 6,245,518 | B1 | 6/2001 | Baier |
| 6,251,639 | B1 | 6/2001 | Kurn |
| 6,258,558 | B1 | 7/2001 | Szostak |
| 6,258,568 | B1 | 7/2001 | Nyren |
| 6,261,804 | B1 | 7/2001 | Szostak |
| 6,265,552 | B1 | 7/2001 | Schatz |
| 6,266,459 | B1 | 7/2001 | Walt |
| 6,268,148 | B1 | 7/2001 | Barany et al. |
| 6,274,320 | B1 | 8/2001 | Rothberg |
| 6,281,804 | B1 | 8/2001 | Haller |
| 6,291,180 | B1 | 9/2001 | Chu |
| 6,291,187 | B1 | 9/2001 | Kingsmore et al. |
| 6,300,063 | B1 | 10/2001 | Lipshutz et al. |
| 6,300,093 | B1 | 10/2001 | Kindsvogel et al. |
| 6,306,597 | B1 | 10/2001 | Macevicz |
| 6,309,824 | B1 | 10/2001 | Drmanac |
| 6,313,284 | B1 | 11/2001 | Kwiatkowski et al. |
| 6,323,009 | B1 | 11/2001 | Lasken et al. |
| 6,337,472 | B1 | 1/2002 | Garner et al. |
| 6,344,316 | B1 | 2/2002 | Lockhart |
| 6,344,329 | B1 | 2/2002 | Lizardi et al. |
| 6,348,990 | B1 | 2/2002 | Igasaki et al. |
| 6,355,431 | B1 | 3/2002 | Chee |
| 6,358,508 | B1 | 3/2002 | Ni et al. |
| 6,368,801 | B1 | 4/2002 | Faruqi |
| 6,391,937 | B1 | 5/2002 | Beuhler et al. |
| 6,401,267 | B1 | 6/2002 | Drmanac |
| 6,404,907 | B1 | 6/2002 | Gilchrist |
| 6,410,708 | B1 | 6/2002 | Ashkenazi et al. |
| 6,416,950 | B1 | 7/2002 | Lohse |
| 6,426,215 | B1 | 7/2002 | Sandell |
| 6,432,360 | B1 | 8/2002 | Church et al. |
| 6,444,661 | B1 | 9/2002 | Barton et al. |
| 6,485,982 | B1 | 11/2002 | Charlton |
| 6,503,713 | B1 | 1/2003 | Rana |
| 6,506,561 | B1 | 1/2003 | Cheval et al. |
| 6,518,018 | B1 | 2/2003 | Szostak |
| 6,534,266 | B1 | 3/2003 | Singer |
| 6,544,732 | B1 | 4/2003 | Chee |
| 6,544,790 | B1 | 4/2003 | Sabatini |
| 6,565,727 | B1 | 5/2003 | Shenderov |
| 6,573,043 | B1 | 6/2003 | Cohen et al. |
| 6,579,695 | B1 | 6/2003 | Lambalot |
| 6,620,584 | B1 | 9/2003 | Chee |
| 6,632,641 | B1 | 10/2003 | Brennan |
| 6,673,620 | B1 | 1/2004 | Loeffler |
| 6,677,160 | B1 | 1/2004 | Stockman et al. |
| 6,699,710 | B1 | 3/2004 | Kononen |
| 6,716,579 | B1 | 4/2004 | Baidya et al. |
| 6,737,236 | B1 | 5/2004 | Pieken et al. |
| 6,770,441 | B2 | 8/2004 | Dickinson |
| 6,773,566 | B2 | 8/2004 | Shenderov |
| 6,773,886 | B2 | 8/2004 | Kaufman |
| 6,787,308 | B2 | 9/2004 | Balasubramanian |
| 6,794,138 | B1 | 9/2004 | Cao et al. |
| 6,797,470 | B2 | 9/2004 | Barany et al. |
| 6,800,453 | B2 | 10/2004 | Labaer |

(56) References Cited

U.S. PATENT DOCUMENTS

| | | | |
|---|---|---|---|
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,852,487 | B1 | 2/2005 | Barany et al. |
| 6,859,570 | B2 | 2/2005 | Walt |
| 6,864,052 | B1 | 3/2005 | Drmanac |
| 6,867,028 | B2 | 3/2005 | Janulaitis |
| 6,872,816 | B1 | 3/2005 | Hall et al. |
| 6,875,572 | B2 | 4/2005 | Prudent et al. |
| 6,878,515 | B1 | 4/2005 | Landegren |
| 6,890,741 | B2 | 5/2005 | Fan et al. |
| 6,897,023 | B2 | 5/2005 | Fu |
| 6,911,132 | B2 | 6/2005 | Pamula |
| 6,911,345 | B2 | 6/2005 | Quake |
| 6,913,881 | B1 | 7/2005 | Aizenstein et al. |
| 6,913,921 | B2 | 7/2005 | Fischer |
| 6,942,968 | B1 | 9/2005 | Dickinson et al. |
| 6,969,488 | B2 | 11/2005 | Bridgham |
| 6,969,589 | B2 | 11/2005 | Patil |
| 6,977,033 | B2 | 12/2005 | Becker |
| 7,001,792 | B2 | 2/2006 | Sauer et al. |
| 7,008,788 | B2 | 3/2006 | Schremp et al. |
| 7,011,944 | B2 | 3/2006 | Prudent et al. |
| 7,052,244 | B2 | 5/2006 | Fouillet |
| 7,057,026 | B2 | 6/2006 | Barnes |
| 7,060,431 | B2 | 6/2006 | Chee et al. |
| 7,081,565 | B2 | 7/2006 | Ohlrogge et al. |
| 7,083,980 | B2 | 8/2006 | Reznikoff et al. |
| 7,098,041 | B2 | 8/2006 | Kaylor et al. |
| 7,115,400 | B1 | 10/2006 | Adessi |
| 7,118,883 | B2 | 10/2006 | Inoue |
| 7,128,893 | B2 | 10/2006 | Leamon et al. |
| 7,138,506 | B2 | 11/2006 | Fagan |
| 7,163,612 | B2 | 1/2007 | Sterling |
| 7,166,431 | B2 | 1/2007 | Chee et al. |
| 7,192,735 | B2 | 3/2007 | Lambalot |
| 7,211,414 | B2 | 5/2007 | Hardin |
| 7,220,573 | B2 | 5/2007 | Shea et al. |
| 7,223,371 | B2 | 5/2007 | Hayenga et al. |
| 7,223,592 | B2 | 5/2007 | Shea et al. |
| 7,229,769 | B2 | 6/2007 | Kozlov |
| 7,244,559 | B2 | 7/2007 | Rothberg |
| 7,255,994 | B2 | 8/2007 | Lao |
| 7,258,976 | B2 | 8/2007 | Mitsuhashi |
| 7,259,258 | B2 | 8/2007 | Kozlov et al. |
| 7,262,063 | B2 | 8/2007 | Banerjee et al. |
| 7,264,929 | B2 | 9/2007 | Rothberg |
| 7,270,950 | B2 | 9/2007 | Szostak |
| 7,282,328 | B2 | 10/2007 | Kong et al. |
| 7,297,518 | B2 | 11/2007 | Quake |
| 7,315,019 | B2 | 1/2008 | Turner |
| 7,328,979 | B2 | 2/2008 | Decre |
| 7,329,492 | B2 | 2/2008 | Hardin |
| 7,358,047 | B2 | 4/2008 | Hafner et al. |
| 7,361,488 | B2 | 4/2008 | Fan et al. |
| 7,364,897 | B2 | 4/2008 | Heaney |
| 7,375,234 | B2 | 5/2008 | Sharpless et al. |
| 7,378,242 | B2 | 5/2008 | Hurt |
| 7,393,665 | B2 | 7/2008 | Brenner |
| 7,405,281 | B2 | 7/2008 | Xu |
| 7,407,757 | B2 | 8/2008 | Brenner |
| 7,427,678 | B2 | 9/2008 | Pieken et al. |
| 7,456,012 | B2 | 11/2008 | Ryttsen et al. |
| 7,462,449 | B2 | 12/2008 | Quake |
| 7,473,767 | B2 | 1/2009 | Dimitrov |
| 7,499,806 | B2 | 3/2009 | Kermani et al. |
| 7,500,637 | B2 | 3/2009 | Marimon et al. |
| 7,501,245 | B2 | 3/2009 | Quake |
| 7,510,637 | B2 | 3/2009 | Barlow et al. |
| 7,534,991 | B2 | 5/2009 | Miller et al. |
| 7,537,897 | B2 | 5/2009 | Brenner |
| 7,544,473 | B2 | 6/2009 | Brennan |
| 7,547,380 | B2 | 6/2009 | Velev |
| 7,555,155 | B2 | 6/2009 | Levenson et al. |
| 7,561,336 | B2 | 7/2009 | Osaka et al. |
| 7,563,576 | B2 | 7/2009 | Chee |
| 7,579,153 | B2 | 8/2009 | Brenner |
| 7,582,420 | B2 | 9/2009 | Oliphant et al. |
| 7,595,883 | B1 | 9/2009 | El Gamal |
| 7,601,492 | B2 | 10/2009 | Fu et al. |
| 7,601,498 | B2 | 10/2009 | Mao |
| 7,608,434 | B2 | 10/2009 | Reznikoff et al. |
| 7,611,869 | B2 | 11/2009 | Fan |
| 7,625,765 | B2 | 12/2009 | Banerjee et al. |
| 7,635,566 | B2 | 12/2009 | Brenner |
| 7,641,779 | B2 | 1/2010 | Becker |
| 7,655,898 | B2 | 2/2010 | Miller |
| 7,666,612 | B2 | 2/2010 | Johnsson |
| 7,674,589 | B2 | 3/2010 | Cohen et al. |
| 7,674,752 | B2 | 3/2010 | He |
| 7,700,286 | B2 | 4/2010 | Stroun et al. |
| 7,709,198 | B2 | 5/2010 | Luo et al. |
| 7,741,106 | B2 | 6/2010 | Moyle et al. |
| 7,754,429 | B2 | 7/2010 | Rigatti |
| 7,776,547 | B2 | 8/2010 | Roth |
| 7,776,567 | B2 | 8/2010 | Mao |
| 7,785,869 | B2 | 8/2010 | Belgrader et al. |
| 7,803,943 | B2 | 9/2010 | Mao |
| 7,844,940 | B2 | 11/2010 | Shin et al. |
| 7,848,553 | B2 | 12/2010 | Hertel et al. |
| 7,858,321 | B2 | 12/2010 | Glezer |
| 7,888,009 | B2 | 2/2011 | Barany et al. |
| 7,892,747 | B2 | 2/2011 | Barany et al. |
| 7,910,304 | B2 | 3/2011 | Drmanac |
| 7,914,981 | B2 | 3/2011 | Barany et al. |
| 7,919,308 | B2 | 4/2011 | Paul |
| 7,941,279 | B2 | 5/2011 | Hwang et al. |
| 7,955,794 | B2 | 6/2011 | Shen et al. |
| 7,960,119 | B2 | 6/2011 | Chee |
| 7,960,120 | B2 | 6/2011 | Rigatti |
| 7,985,565 | B2 | 7/2011 | Mayer et al. |
| 8,003,354 | B2 | 8/2011 | Shen et al. |
| 8,030,466 | B2 | 10/2011 | Shin et al. |
| 8,030,477 | B2 | 10/2011 | Cerrina et al. |
| 8,046,043 | B2 | 10/2011 | Asano et al. |
| 8,074,802 | B2 | 12/2011 | Webb et al. |
| 8,076,063 | B2 | 12/2011 | Fan |
| 8,092,784 | B2 | 1/2012 | Mao |
| 8,124,751 | B2 | 2/2012 | Pierce et al. |
| D655,421 | S | 3/2012 | Lee et al. |
| 8,131,476 | B2 | 3/2012 | Cline et al. |
| 8,148,068 | B2 | 4/2012 | Brenner |
| 8,148,518 | B2 | 4/2012 | Buchanan |
| 8,168,134 | B2 | 5/2012 | Lehto |
| 8,198,028 | B2 | 6/2012 | Rigatti et al. |
| 8,199,999 | B2 | 6/2012 | Hoyt et al. |
| 8,206,917 | B2 | 6/2012 | Chee |
| 8,207,093 | B2 | 6/2012 | Szostak |
| 8,268,554 | B2 | 9/2012 | Schallmeiner |
| 8,278,034 | B2 | 10/2012 | Muraca |
| 8,288,103 | B2 | 10/2012 | Oliphant |
| 8,288,122 | B2 | 10/2012 | O'Leary et al. |
| 8,330,087 | B2 | 12/2012 | Domenicali |
| 8,337,851 | B2 | 12/2012 | Aukerman |
| 8,343,500 | B2 | 1/2013 | Wraith |
| 8,383,338 | B2 | 2/2013 | Kitzman |
| 8,415,102 | B2 | 4/2013 | Geiss et al. |
| 8,431,691 | B2 | 4/2013 | McKernan et al. |
| 8,460,865 | B2 | 6/2013 | Chee |
| 8,462,981 | B2 | 6/2013 | Determan et al. |
| 8,481,257 | B2 | 7/2013 | Van Eijk |
| 8,481,258 | B2 | 7/2013 | Church et al. |
| 8,481,292 | B2 | 7/2013 | Casbon |
| 8,481,698 | B2 | 7/2013 | Lieberman et al. |
| 8,486,625 | B2 | 7/2013 | Gunderson |
| 8,507,204 | B2 | 8/2013 | Pierce et al. |
| 8,519,115 | B2 | 8/2013 | Webster et al. |
| 8,551,710 | B2 | 10/2013 | Bernitz et al. |
| 8,568,979 | B2 | 10/2013 | Stuelpnagel et al. |
| RE44,596 | E | 11/2013 | Stroun et al. |
| 8,586,310 | B2 | 11/2013 | Mitra |
| 8,597,891 | B2 | 12/2013 | Barany et al. |
| 8,603,743 | B2 | 12/2013 | Liu et al. |
| 8,604,182 | B2 | 12/2013 | Luo et al. |

(56) References Cited

U.S. PATENT DOCUMENTS 8,614,073 B2 12/2013 Van Eijk
8,624,016 B2 1/2014 Barany et al.
8,637,242 B2 1/2014 Shen
8,658,361 B2 2/2014 Wu et al.
8,685,889 B2 4/2014 Van Eijk
8,741,564 B2 6/2014 Seligmann
8,741,606 B2 6/2014 Casbon
8,748,103 B2 6/2014 Faham et al.
8,771,950 B2 7/2014 Church et al.
8,778,849 B2 7/2014 Bowen
8,785,353 B2 7/2014 Van Eijk
8,790,873 B2 7/2014 Namsaraev et al.
8,809,238 B2 8/2014 Livak et al.
8,815,512 B2 8/2014 Van Eijk
8,835,358 B2 9/2014 Fodor
8,865,410 B2 10/2014 Shendure
8,906,626 B2 12/2014 Oliphant et al.
8,911,945 B2 12/2014 Van Eijk
8,925,175 B2 1/2015 Aldred et al.
8,936,912 B2 1/2015 Mitra
8,951,726 B2 2/2015 Luo et al.
8,951,728 B2 2/2015 Rasmussen
8,951,781 B2 2/2015 Reed
8,986,926 B2 3/2015 Ferree et al.
9,005,891 B2 4/2015 Sinicropi et al.
9,005,935 B2 4/2015 Belyaev
9,023,768 B2 5/2015 Van Eijk
9,062,348 B1 6/2015 Van Eijk
9,080,210 B2 7/2015 Van Eijk
9,085,798 B2 7/2015 Chee
9,103,785 B2 8/2015 Okura et al.
9,121,069 B2 9/2015 Lo
9,163,283 B2 10/2015 Chee et al.
9,194,001 B2 11/2015 Brenner
9,201,063 B2 12/2015 Sood et al.
9,217,176 B2 12/2015 Faham et al.
9,290,808 B2 3/2016 Fodor
9,290,809 B2 3/2016 Fodor
9,309,556 B2 4/2016 Myllykangas et al.
9,328,383 B2 5/2016 Van Eijk
9,334,536 B2 5/2016 Van Eijk
9,340,830 B2 5/2016 Lipson
9,371,563 B2 6/2016 Geiss et al.
9,371,598 B2 6/2016 Chee
9,376,716 B2 6/2016 Van Eijk
9,376,717 B2 6/2016 Gao et al.
9,376,719 B2 6/2016 Eijk
9,404,156 B2 8/2016 Hicks
9,416,409 B2 8/2016 Hayden
9,436,088 B2 9/2016 Seul et al.
9,447,459 B2 9/2016 Van Eijk
9,453,256 B2 9/2016 Van Eijk
9,493,820 B2 11/2016 Van Eijk
9,494,588 B2 11/2016 Springer
9,506,061 B2 11/2016 Brown
9,512,487 B2 12/2016 Faham et al.
9,541,504 B2 1/2017 Hoyt
9,557,330 B2 1/2017 Siciliano et al.
9,574,230 B2 2/2017 Van Eijk
9,593,365 B2 3/2017 Frisen et al.
9,598,728 B2 3/2017 Barany et al.
9,624,538 B2 4/2017 Church et al.
9,657,335 B2 5/2017 Van Eijk
9,670,542 B2 6/2017 Eijk
9,671,344 B2 6/2017 Staker
9,694,361 B2 7/2017 Bharadwaj
9,702,004 B2 7/2017 Van Eijk
9,714,446 B2 7/2017 Webster et al.
9,714,937 B2 7/2017 Dunaway
9,745,627 B2 8/2017 Van Eijk
9,751,084 B2 9/2017 Greenizen et al.
9,777,324 B2 10/2017 Van Eijk
9,816,134 B2 11/2017 Namsaraev
9,850,536 B2 12/2017 Oliphant et al.
9,868,979 B2 1/2018 Chee et al.
9,879,313 B2 1/2018 Chee et al.
9,889,422 B2 2/2018 Smith et al.
9,896,721 B2 2/2018 Van Eijk
9,898,576 B2 2/2018 Van Eijk
9,898,577 B2 2/2018 Van Eijk
9,902,950 B2 2/2018 Church et al.
9,902,991 B2 2/2018 Sinicropi et al.
9,958,454 B2 5/2018 Kozlov et al.
10,023,907 B2 7/2018 Van Eijk
10,030,261 B2 7/2018 Frisen et al.
10,072,104 B2 9/2018 Winnik et al.
10,077,478 B2 9/2018 Faham et al.
10,095,832 B2 10/2018 Van Eijk
10,144,966 B2 12/2018 Cantor
10,196,691 B2 2/2019 Harkin et al.
10,227,639 B2 3/2019 Levner et al.
10,246,752 B2 4/2019 Faham et al.
10,266,876 B2 4/2019 Cai et al.
10,267,808 B2 4/2019 Cai
10,357,771 B2 7/2019 Bharadwaj
10,391,467 B2 8/2019 Zhou et al.
10,428,326 B2 10/2019 Belhocine et al.
10,465,235 B2 11/2019 Gullberg et al.
10,501,791 B2 12/2019 Church et al.
10,633,648 B2 4/2020 Seelig et al.
10,662,466 B2 5/2020 Berry et al.
10,669,569 B2 6/2020 Gullberg et al.
10,685,210 B2 6/2020 Wimberger-Friedl et al.
10,697,013 B1 6/2020 Brenner et al.
10,725,027 B2 7/2020 Bell
10,767,223 B1 9/2020 Brenner et al.
10,774,372 B2 9/2020 Chee et al.
10,774,374 B2 9/2020 Frisen et al.
10,829,803 B2 11/2020 Terbrueggen et al.
10,858,702 B2 12/2020 Lucero et al.
10,927,403 B2 2/2021 Chee et al.
10,995,362 B2 5/2021 Dallett et al.
11,046,996 B1 6/2021 Chee et al.
11,162,132 B2 11/2021 Frisen et al.
11,180,805 B2 11/2021 Lucero et al.
11,214,796 B2 1/2022 Shirai et al.
11,286,515 B2 3/2022 Chee et al.
11,299,774 B2 4/2022 Frisen et al.
11,332,790 B2 5/2022 Chell et al.
11,352,659 B2 6/2022 Frisen et al.
11,359,228 B2 6/2022 Chee et al.
11,390,912 B2 7/2022 Frisen et al.
11,407,992 B2 8/2022 Dadhwal
11,408,029 B2 8/2022 Katiraee et al.
11,434,524 B2 9/2022 Ramachandran Iyer et al.
11,459,607 B1 10/2022 Terry et al.
11,479,809 B2 10/2022 Frisen et al.
11,492,612 B1 11/2022 Dadhwal
11,501,440 B2 11/2022 Weisenfeld et al.
11,505,828 B2 11/2022 Chell et al.
11,512,308 B2 11/2022 Gallant et al.
11,519,033 B2 12/2022 Schnall-Levin et al.
11,535,887 B2 12/2022 Gallant et al.
11,560,592 B2 1/2023 Chew et al.
11,560,593 B2 1/2023 Chell et al.
11,592,447 B2 2/2023 Uytingco et al.
11,608,498 B2 3/2023 Gallant et al.
11,608,520 B2 3/2023 Galonska et al.
11,613,773 B2 3/2023 Frisen et al.
11,618,897 B2 4/2023 Kim et al.
11,618,918 B2 4/2023 Chee et al.
11,624,063 B2 4/2023 Dadhwal
11,624,086 B2 4/2023 Uytingco et al.
11,649,485 B2 5/2023 Yin et al.
11,661,626 B2 5/2023 Katiraee et al.
11,680,260 B2 6/2023 Kim et al.
11,692,218 B2 7/2023 Engblom et al.
11,702,693 B2 7/2023 Bharadwaj
11,702,698 B2 7/2023 Stoeckius
11,732,299 B2 8/2023 Ramachandran Iyer
11,732,300 B2 8/2023 Bava
11,739,372 B2 8/2023 Frisen et al.
11,739,381 B2 8/2023 Chew et al.
11,753,673 B2 9/2023 Chew et al.

(56) References Cited

U.S. PATENT DOCUMENTS 11,753,674 B2 9/2023 Chee et al.
11,753,675 B2 9/2023 Ramachandran Iyer
11,761,038 B1 9/2023 Stoeckius
11,768,175 B1 9/2023 Kim et al.
11,773,433 B2 10/2023 Gallant et al.
11,781,130 B2 10/2023 Dadhwal
11,788,122 B2 10/2023 Frisen et al.
11,795,498 B2 10/2023 Frisen et al.
11,795,507 B2 10/2023 Chell et al.
11,808,769 B2 11/2023 Uytingco et al.
11,821,024 B2 11/2023 Chee et al.
11,821,035 B1 11/2023 Bent et al.
11,827,935 B1 11/2023 Ramachandran Iyer et al.
11,835,462 B2 12/2023 Bava
11,840,687 B2 12/2023 Gallant et al.
11,840,724 B2 12/2023 Chew et al.
11,845,979 B2 12/2023 Engblom et al.
11,859,178 B2 1/2024 Gallant et al.
11,866,767 B2 1/2024 Uytingco et al.
11,873,482 B2 1/2024 Kim et al.
11,891,654 B2 2/2024 Alvarado Martinez et al.
11,898,205 B2 2/2024 Bava
11,926,822 B1 3/2024 Gohil et al.
11,926,863 B1 3/2024 Boutet
11,926,867 B2 3/2024 Yin et al.
11,933,957 B1 3/2024 Tentori et al.
11,952,627 B2 4/2024 Stoeckius
11,959,076 B2 4/2024 Kim et al.
11,959,130 B2 4/2024 Galonska et al.
11,965,213 B2 4/2024 Williams
11,970,739 B2 4/2024 Chew et al.
11,981,958 B1 5/2024 Galonska
11,981,960 B1 5/2024 Lin et al.
11,981,965 B2 5/2024 Chell et al.
RE50,065 E 7/2024 Frisen et al.
12,024,741 B2 7/2024 Tentori et al.
12,031,177 B1 7/2024 Tentori et al.
12,060,604 B2 8/2024 Katiraee et al.
12,071,655 B2 8/2024 Sukovich et al.
12,076,701 B2 9/2024 Bava
12,098,417 B2 9/2024 Engblom et al.
12,098,985 B2 9/2024 Cox et al.
12,110,541 B2 10/2024 Bava
12,117,439 B2 10/2024 Delaney et al.
12,128,403 B2 10/2024 Kim et al.
12,129,516 B2 10/2024 Tentori et al.
12,157,124 B2 12/2024 Cox et al.
12,180,543 B2 12/2024 Uytingco et al.
12,195,790 B2 1/2025 Sukovich et al.
12,203,134 B2 1/2025 Nagendran et al.
12,209,280 B1 1/2025 Mignardi et al.
D1,064,308 S 2/2025 Alimsijah et al.
12,223,751 B2 2/2025 Li et al.
12,228,544 B2 2/2025 Kim et al.
12,241,060 B2 3/2025 Kim et al.
12,241,890 B2 3/2025 Delaney et al.
12,249,085 B2 3/2025 Tentori et al.
12,265,079 B1 4/2025 Bent
12,270,077 B2 4/2025 Schnall-Levin et al.
12,275,988 B2 4/2025 Galonska et al.
12,281,357 B1 4/2025 Tentori et al.
12,286,673 B2 4/2025 Bava
12,287,264 B2 4/2025 Cox et al.
12,297,486 B2 5/2025 Patterson et al.
12,344,892 B2 7/2025 Schnall-Levin et al.
12,365,935 B2 7/2025 Chew et al.
12,365,942 B2 7/2025 Stoeckius
12,371,688 B2 7/2025 Kim et al.
12,378,607 B2 8/2025 Schnall-Levin et al.
12,385,083 B2 8/2025 Shah
12,399,123 B1 8/2025 Shah et al.
12,404,544 B2 9/2025 Tentori et al.
12,405,264 B2 9/2025 Stoeckius
12,416,603 B2 9/2025 Tentori et al.
12,435,363 B1 10/2025 Gallant et al.
12,442,045 B2 10/2025 Williams
12,497,654 B2 12/2025 Ramachandran Iyer et al.
12,508,590 B2 12/2025 Kim et al.
D1,108,656 S 1/2026 Alimsijah et al.
12,529,094 B2 1/2026 Bent et al.
12,545,949 B2 2/2026 Bent et al.
12,553,805 B2 2/2026 Shahjamali
12,553,898 B1 2/2026 Uytingco et al.
12,566,113 B2 3/2026 Delaney et al.
12,566,114 B2 3/2026 Cox et al.
12,571,029 B1 3/2026 Galonska et al.
2001/0029017 A1 10/2001 Yasuda et al.
2001/0035763 A1 11/2001 Mess
2001/0039029 A1 11/2001 Nemori et al.
2001/0053519 A1 12/2001 Fodor et al.
2001/0055764 A1 12/2001 Empendocles et al.
2002/0006477 A1 1/2002 Shishido et al.
2002/0022261 A1 2/2002 Anderson et al.
2002/0040275 A1 4/2002 Cravatt
2002/0045169 A1 4/2002 Shoemaker et al.
2002/0045272 A1 4/2002 McDevitt et al.
2002/0048766 A1 4/2002 Doyle et al.
2002/0051986 A1 5/2002 Baez et al.
2002/0055100 A1 5/2002 Kawashima
2002/0058250 A1 5/2002 Firth
2002/0064779 A1 5/2002 Landegren
2002/0086441 A1 7/2002 Baranov et al.
2002/0127552 A1 9/2002 Church et al.
2002/0132246 A1 9/2002 Kallioniemi et al.
2002/0137031 A1 9/2002 Wolber
2002/0146745 A1 10/2002 Natan et al.
2002/0150909 A1 10/2002 Stuelpnagel
2002/0164611 A1 11/2002 Bamdad
2002/0168645 A1 11/2002 Taylor
2002/0194938 A1 12/2002 Koo et al.
2003/0017451 A1 1/2003 Wang et al.
2003/0022207 A1 1/2003 Balasubramanian
2003/0027342 A1 2/2003 Sheridan et al.
2003/0040011 A1 2/2003 Barth et al.
2003/0040035 A1 2/2003 Slamon
2003/0064398 A1 4/2003 Barnes
2003/0073086 A1 4/2003 Guire et al.
2003/0087232 A1 5/2003 Christians
2003/0092624 A1 5/2003 Wang et al.
2003/0096323 A1 5/2003 James
2003/0108726 A1 6/2003 Schembri et al.
2003/0113713 A1 6/2003 Glezer
2003/0124595 A1 7/2003 Lizardi
2003/0134279 A1 7/2003 Isola et al.
2003/0134410 A1 7/2003 Silva et al.
2003/0138353 A1 7/2003 Bargoot et al.
2003/0138879 A1 7/2003 Lambalot
2003/0148335 A1 8/2003 Shen et al.
2003/0152927 A1 8/2003 Jakobsen et al.
2003/0153850 A1 8/2003 Davis et al.
2003/0162216 A1 8/2003 Gold
2003/0165948 A1 9/2003 Alsmadi et al.
2003/0170637 A1 9/2003 Pirrung et al.
2003/0175947 A1 9/2003 Liu et al.
2003/0186310 A1 10/2003 Kincaid
2003/0190744 A1 10/2003 McGarry et al.
2003/0205632 A1 11/2003 Kim et al.
2003/0211483 A1 11/2003 Schroeder et al.
2003/0211489 A1 11/2003 Shen et al.
2003/0215936 A1 11/2003 Kallioniemi et al.
2003/0224419 A1 12/2003 Corcoran
2003/0231983 A1 12/2003 Schleifer
2003/0232348 A1 12/2003 Jones et al.
2003/0232382 A1 12/2003 Brennan
2003/0235535 A1 12/2003 Zhou
2003/0235852 A1 12/2003 Roberts
2003/0235854 A1 12/2003 Chan et al.
2004/0002090 A1 1/2004 Mayer et al.
2004/0009487 A1 1/2004 Kadushin et al.
2004/0019005 A1 1/2004 Van Ness
2004/0019196 A1 1/2004 Beir et al.
2004/0023320 A1 2/2004 Steiner et al.
2004/0029203 A1 2/2004 Gumbrecht et al.
2004/0033499 A1 2/2004 Ilsley et al.

(56) References Cited

U.S. PATENT DOCUMENTS

2004/0050699 A1 3/2004 Goncalves
2004/0067492 A1 4/2004 Peng et al.
2004/0067493 A1 4/2004 Matsuzaki
2004/0071605 A1 4/2004 Coonan et al.
2004/0082058 A1 4/2004 Schleifer et al.
2004/0082059 A1 4/2004 Webb
2004/0096853 A1 5/2004 Mayer
2004/0101835 A1 5/2004 Willis et al.
2004/0106110 A1 6/2004 Balasubramanian
2004/0112442 A1 6/2004 Maerkl
2004/0121456 A1 6/2004 Fischer
2004/0166553 A1 8/2004 Nguyen et al.
2004/0175822 A1 9/2004 Timperman et al.
2004/0219588 A1 11/2004 Furuta
2004/0223890 A1 11/2004 Summers et al.
2004/0224326 A1 11/2004 Kim et al.
2004/0235103 A1 11/2004 Reznikoff et al.
2004/0241660 A1 12/2004 Wojtowicz et al.
2004/0248287 A1 12/2004 Hu et al.
2004/0248325 A1 12/2004 Bukusoglu et al.
2004/0259105 A1 12/2004 Fan et al.
2005/0003431 A1 1/2005 Wucherpfennig
2005/0014203 A1 1/2005 Darfler et al.
2005/0019776 A1 1/2005 Callow et al.
2005/0019842 A1 1/2005 Prober et al.
2005/0026188 A1 2/2005 Van Kessel
2005/0037362 A1 2/2005 Remacle et al.
2005/0037393 A1 2/2005 Gunderson et al.
2005/0042695 A1 2/2005 Meares et al.
2005/0048498 A1 3/2005 Woudenberg et al.
2005/0048535 A1 3/2005 Santin
2005/0048580 A1 3/2005 Labaer
2005/0064432 A1 3/2005 Huang et al.
2005/0064460 A1 3/2005 Holliger et al.
2005/0079518 A1 4/2005 Baker et al.
2005/0079520 A1 4/2005 Wu
2005/0095627 A1 5/2005 Kolman et al.
2005/0100900 A1 5/2005 Kawashima et al.
2005/0106617 A1 5/2005 Besemer et al.
2005/0118602 A1 6/2005 Li et al.
2005/0130120 A1 6/2005 Lambotte et al.
2005/0130173 A1 6/2005 Leamon et al.
2005/0130188 A1 6/2005 Walt
2005/0130223 A1 6/2005 Varon
2005/0136414 A1 6/2005 Gunderson et al.
2005/0147537 A1 7/2005 Sangha
2005/0148500 A1 7/2005 Heller et al.
2005/0164292 A1 7/2005 Farooqui
2005/0170373 A1 8/2005 Monforte
2005/0179746 A1 8/2005 Roux et al.
2005/0191656 A1 9/2005 Drmanac et al.
2005/0191698 A1 9/2005 Chee et al.
2005/0196786 A1 9/2005 Levy
2005/0202433 A1 9/2005 Van Beuningen
2005/0226780 A1 10/2005 Sandell et al.
2005/0227271 A1 10/2005 Kwon
2005/0239079 A1 10/2005 Erlander et al.
2005/0239119 A1 10/2005 Tsukada et al.
2005/0239192 A1 10/2005 Nasarabadi et al.
2005/0244850 A1 11/2005 Huang
2005/0255548 A1 11/2005 Lipovsek et al.
2005/0257284 A1 11/2005 Nakajima et al.
2005/0260653 A1 11/2005 LaBaer
2005/0266417 A1 12/2005 Barany et al.
2006/0003394 A1 1/2006 Song
2006/0039823 A1 2/2006 Yamakawa et al.
2006/0041384 A1 2/2006 Kermani et al.
2006/0041385 A1 2/2006 Bauer et al.
2006/0046313 A1 3/2006 Roth
2006/0063160 A1 3/2006 West et al.
2006/0073506 A1 4/2006 Christians et al.
2006/0079453 A1 4/2006 Sidney et al.
2006/0084078 A1 4/2006 Zhao
2006/0088872 A1 4/2006 Ahmadian et al.
2006/0093528 A1 5/2006 Benerjee et al.
2006/0105352 A1 5/2006 Qiao et al.
2006/0110739 A1 5/2006 Heyduk
2006/0127946 A1 6/2006 Montagu et al.
2006/0134669 A1 6/2006 Casasanta
2006/0153736 A1 7/2006 Kalra et al.
2006/0154286 A1 7/2006 Kong et al.
2006/0164490 A1 7/2006 Kim et al.
2006/0172278 A1 8/2006 Bonner et al.
2006/0180489 A1 8/2006 Guiney et al.
2006/0183150 A1 8/2006 Cohen et al.
2006/0188875 A1 8/2006 Cox et al.
2006/0188901 A1 8/2006 Barnes et al.
2006/0188906 A1 8/2006 Kim et al.
2006/0194331 A1 8/2006 Pamula et al.
2006/0199183 A1 9/2006 Valat et al.
2006/0199207 A1 9/2006 Matysiak
2006/0211001 A1 9/2006 Yu et al.
2006/0216721 A1 9/2006 Kozlov et al.
2006/0216775 A1 9/2006 Burkart et al.
2006/0228758 A1 10/2006 Muchhal et al.
2006/0240439 A1 10/2006 Smith et al.
2006/0246475 A1 11/2006 Peterson et al.
2006/0263789 A1 11/2006 Kincaid
2006/0275782 A1 12/2006 Gunderson et al.
2006/0275799 A1 12/2006 Banerjee et al.
2006/0281109 A1 12/2006 Barr Ost et al.
2006/0292559 A1 12/2006 Reddy et al.
2007/0003954 A1 1/2007 Kodadek et al.
2007/0014810 A1 1/2007 Baker et al.
2007/0020625 A1 1/2007 Duchaud et al.
2007/0020640 A1 1/2007 McCloskey et al.
2007/0020669 A1 1/2007 Ericsson
2007/0023292 A1 2/2007 Kim et al.
2007/0026430 A1 2/2007 Andersen et al.
2007/0036511 A1 2/2007 Lundquist et al.
2007/0048812 A1 3/2007 Moravec et al.
2007/0054288 A1 3/2007 Su et al.
2007/0087360 A1 4/2007 Boyd
2007/0099208 A1 5/2007 Drmanac et al.
2007/0116612 A1 5/2007 Williamson
2007/0128071 A1 6/2007 Shea et al.
2007/0128624 A1 6/2007 Gormley et al.
2007/0128656 A1 6/2007 Agrawal
2007/0134723 A1 6/2007 Kozlov et al.
2007/0141718 A1 6/2007 Bui et al.
2007/0161020 A1 7/2007 Luo et al.
2007/0161029 A1 7/2007 Li et al.
2007/0166705 A1 7/2007 Milton et al.
2007/0166725 A1 7/2007 McBride et al.
2007/0172873 A1 7/2007 Brenner et al.
2007/0178503 A1 8/2007 Jiang
2007/0184456 A1 8/2007 Chee et al.
2007/0207482 A1 9/2007 Church et al.
2007/0215466 A1 9/2007 Okada
2007/0231823 A1 10/2007 McKernan
2007/0231824 A1 10/2007 Chee et al.
2007/0243634 A1 10/2007 Pamula et al.
2007/0251824 A1 11/2007 Patton
2007/0254305 A1 11/2007 Paik et al.
2007/0264656 A1 11/2007 Kawamura
2007/0269347 A1 11/2007 Stanchfield et al.
2007/0269805 A1 11/2007 Hogers
2007/0280517 A1 12/2007 Torre-Bueno et al.
2008/0003586 A1 1/2008 Hyde et al.
2008/0009071 A1 1/2008 Sogard
2008/0009420 A1 1/2008 Schroth et al.
2008/0020453 A1 1/2008 Ehben et al.
2008/0032301 A1 2/2008 Rank et al.
2008/0032310 A1 2/2008 Shannon et al.
2008/0033159 A1 2/2008 Kadushin et al.
2008/0038734 A1 2/2008 Sorge et al.
2008/0043235 A1 2/2008 Oldham et al.
2008/0047835 A1 2/2008 MacConnell
2008/0050780 A1 2/2008 Lee et al.
2008/0071071 A1 3/2008 LaBaer et al.
2008/0108082 A1 5/2008 Rank et al.
2008/0108804 A1 5/2008 Hayashizaki et al.
2008/0124252 A1 5/2008 Marchand et al.
2008/0124810 A1 5/2008 Terbrueggen et al.

(56) References Cited

U.S. PATENT DOCUMENTS

| | | | |
|---|---|---|---|
| 2008/0128627 | A1 | 6/2008 | Lundquist et al. |
| 2008/0132429 | A1 | 6/2008 | Perov et al. |
| 2008/0145378 | A1 | 6/2008 | Ovaa et al. |
| 2008/0145616 | A1 | 6/2008 | Gharib et al. |
| 2008/0153086 | A1 | 6/2008 | Wong |
| 2008/0160580 | A1 | 7/2008 | Adessi et al. |
| 2008/0199929 | A1 | 8/2008 | Yeung et al. |
| 2008/0218838 | A1 | 9/2008 | Rey-Mermet |
| 2008/0220434 | A1 | 9/2008 | Thomas |
| 2008/0220981 | A1 | 9/2008 | McGregor |
| 2008/0261204 | A1 | 10/2008 | Lexow |
| 2008/0280773 | A1 | 11/2008 | Fedurco et al. |
| 2008/0286795 | A1 | 11/2008 | Kawashima et al. |
| 2008/0286878 | A1 | 11/2008 | Vezenov |
| 2008/0293046 | A1 | 11/2008 | Allawi et al. |
| 2008/0293591 | A1 | 11/2008 | Taussig et al. |
| 2008/0312103 | A1 | 12/2008 | Nemoto et al. |
| 2009/0005252 | A1 | 1/2009 | Drmanac et al. |
| 2009/0006002 | A1 | 1/2009 | Honisch et al. |
| 2009/0011943 | A1 | 1/2009 | Drmanac et al. |
| 2009/0018024 | A1 | 1/2009 | Church et al. |
| 2009/0023148 | A1 | 1/2009 | Moyle et al. |
| 2009/0026082 | A1 | 1/2009 | Rothberg et al. |
| 2009/0035777 | A1 | 2/2009 | Kokoris et al. |
| 2009/0036323 | A1 | 2/2009 | van Eijk et al. |
| 2009/0048510 | A1 | 2/2009 | Miller et al. |
| 2009/0060866 | A1 | 3/2009 | Dousson et al. |
| 2009/0062148 | A1 | 3/2009 | Goldberg |
| 2009/0068667 | A1 | 3/2009 | Meisner et al. |
| 2009/0082212 | A1 | 3/2009 | Williams |
| 2009/0099041 | A1 | 4/2009 | Church et al. |
| 2009/0105959 | A1 | 4/2009 | Braverman et al. |
| 2009/0117573 | A1 | 5/2009 | Fu et al. |
| 2009/0127589 | A1 | 5/2009 | Rothberg et al. |
| 2009/0136932 | A1 | 5/2009 | Craighead |
| 2009/0152116 | A1 | 6/2009 | Boles et al. |
| 2009/0155781 | A1 | 6/2009 | Drmanac et al. |
| 2009/0169089 | A1 | 7/2009 | Hunt et al. |
| 2009/0170713 | A1 | 7/2009 | van Eijk et al. |
| 2009/0181375 | A1 | 7/2009 | Peter et al. |
| 2009/0192044 | A1 | 7/2009 | Fouillet |
| 2009/0197326 | A1 | 8/2009 | El Gamal et al. |
| 2009/0202998 | A1 | 8/2009 | Schlumpberger et al. |
| 2009/0215633 | A1 | 8/2009 | Van Eijk et al. |
| 2009/0226911 | A1 | 9/2009 | Mauk et al. |
| 2009/0233802 | A1 | 9/2009 | Bignell et al. |
| 2009/0239232 | A1 | 9/2009 | Kurn |
| 2009/0253163 | A1 | 10/2009 | Xie et al. |
| 2009/0253581 | A1 | 10/2009 | Van Eijk et al. |
| 2009/0253582 | A1 | 10/2009 | Pena et al. |
| 2009/0264299 | A1 | 10/2009 | Drmanac et al. |
| 2009/0270273 | A1 | 10/2009 | Burns et al. |
| 2009/0280487 | A1 | 11/2009 | Hung et al. |
| 2009/0283407 | A1 | 11/2009 | Eijk |
| 2009/0286249 | A1 | 11/2009 | Becker et al. |
| 2009/0289184 | A1 | 11/2009 | Deininger |
| 2009/0291854 | A1 | 11/2009 | Weisinger-Mayr et al. |
| 2009/0298075 | A1 | 12/2009 | Travers et al. |
| 2009/0305237 | A1 | 12/2009 | Cantor et al. |
| 2009/0312193 | A1 | 12/2009 | Kim et al. |
| 2009/0321262 | A1 | 12/2009 | Adachi et al. |
| 2010/0009871 | A1 | 1/2010 | Reed et al. |
| 2010/0014537 | A1 | 1/2010 | Jacquet et al. |
| 2010/0031757 | A1 | 2/2010 | Hoyer |
| 2010/0035249 | A1 | 2/2010 | Hayashizaki et al. |
| 2010/0047790 | A1 | 2/2010 | Southern et al. |
| 2010/0055733 | A1 | 3/2010 | Lutolf et al. |
| 2010/0069263 | A1 | 3/2010 | Shendure et al. |
| 2010/0096266 | A1 | 4/2010 | Kim et al. |
| 2010/0099103 | A1 | 4/2010 | Hsieh et al. |
| 2010/0105052 | A1 | 4/2010 | Drmanac et al. |
| 2010/0105112 | A1 | 4/2010 | Heltze et al. |
| 2010/0108577 | A1 | 5/2010 | Wang et al. |
| 2010/0111768 | A1 | 5/2010 | Banerjee et al. |
| 2010/0113302 | A1 | 5/2010 | Williams |
| 2010/0120043 | A1 | 5/2010 | Sood et al. |
| 2010/0120097 | A1 | 5/2010 | Matz et al. |
| 2010/0120098 | A1 | 5/2010 | Grunenwald et al. |
| 2010/0126862 | A1 | 5/2010 | Sabin et al. |
| 2010/0129874 | A1 | 5/2010 | Mitra et al. |
| 2010/0137143 | A1 | 6/2010 | Rothberg et al. |
| 2010/0145037 | A1 | 6/2010 | Makarov et al. |
| 2010/0151447 | A1 | 6/2010 | Ely |
| 2010/0151464 | A1 | 6/2010 | Stuelpnagel et al. |
| 2010/0151511 | A1 | 6/2010 | Gereenizer et al. |
| 2010/0159446 | A1 | 6/2010 | Haff et al. |
| 2010/0173384 | A1 | 7/2010 | Johnsson et al. |
| 2010/0184614 | A1 | 7/2010 | Ye et al. |
| 2010/0184618 | A1 | 7/2010 | Namsaraev et al. |
| 2010/0201809 | A1 | 8/2010 | Oyama et al. |
| 2010/0210475 | A1 | 8/2010 | Lee et al. |
| 2010/0216137 | A1 | 8/2010 | Bankaitis-Davis et al. |
| 2010/0227329 | A1 | 9/2010 | Cuppens |
| 2010/0267590 | A1 | 10/2010 | Grudzien et al. |
| 2010/0273219 | A1 | 10/2010 | May et al. |
| 2010/0273679 | A1 | 10/2010 | Cuppoletti et al. |
| 2010/0282617 | A1 | 11/2010 | Rothberg et al. |
| 2010/0303722 | A1 | 12/2010 | Jin et al. |
| 2011/0015494 | A1 | 1/2011 | Spaulding |
| 2011/0024511 | A1 | 2/2011 | Rietzler et al. |
| 2011/0027772 | A1 | 2/2011 | Ahn et al. |
| 2011/0028685 | A1 | 2/2011 | Purkayastha et al. |
| 2011/0031123 | A1 | 2/2011 | Schulze et al. |
| 2011/0033854 | A1 | 2/2011 | Drmanac et al. |
| 2011/0045462 | A1 | 2/2011 | Fu et al. |
| 2011/0048951 | A1 | 3/2011 | Wu |
| 2011/0059436 | A1 | 3/2011 | Hardin et al. |
| 2011/0059865 | A1 | 3/2011 | Smith et al. |
| 2011/0086774 | A1 | 4/2011 | Dunaway |
| 2011/0090563 | A1 | 4/2011 | Krasov |
| 2011/0111409 | A1 | 5/2011 | Sinicropi et al. |
| 2011/0130307 | A1 | 6/2011 | Takahashi et al. |
| 2011/0151451 | A1 | 6/2011 | Lemaire et al. |
| 2011/0152111 | A1 | 6/2011 | Fan et al. |
| 2011/0165178 | A1 | 7/2011 | Wasylyk et al. |
| 2011/0172115 | A1 | 7/2011 | Thompson et al. |
| 2011/0177518 | A1 | 7/2011 | Kartalov et al. |
| 2011/0201515 | A1 | 8/2011 | Webster et al. |
| 2011/0207134 | A1 | 8/2011 | Faham et al. |
| 2011/0223613 | A1 | 9/2011 | Gut |
| 2011/0237449 | A1 | 9/2011 | McMaster et al. |
| 2011/0244448 | A1 | 10/2011 | Shirai et al. |
| 2011/0245101 | A1 | 10/2011 | Chee et al. |
| 2011/0245111 | A1 | 10/2011 | Chee |
| 2011/0269155 | A1 | 11/2011 | Reker-Hadrup et al. |
| 2011/0269631 | A1 | 11/2011 | Fu et al. |
| 2011/0269647 | A1 | 11/2011 | Ule et al. |
| 2011/0275077 | A1 | 11/2011 | James |
| 2011/0287435 | A1 | 11/2011 | Grunenwald et al. |
| 2012/0004140 | A1 | 1/2012 | Staker |
| 2012/0010091 | A1 | 1/2012 | Linnarson |
| 2012/0021930 | A1 | 1/2012 | Schoen et al. |
| 2012/0046175 | A1 | 2/2012 | Rodesch et al. |
| 2012/0046178 | A1 | 2/2012 | Van Den Boom et al. |
| 2012/0065081 | A1 | 3/2012 | Chee |
| 2012/0077693 | A1 | 3/2012 | Cazalis et al. |
| 2012/0129248 | A1 | 5/2012 | Chee et al. |
| 2012/0135871 | A1 | 5/2012 | Van Eijk et al. |
| 2012/0142014 | A1 | 6/2012 | Cai |
| 2012/0157322 | A1 | 6/2012 | Myllykangas |
| 2012/0160683 | A1 | 6/2012 | Ye et al. |
| 2012/0177543 | A1 | 7/2012 | Battrell |
| 2012/0195810 | A1 | 8/2012 | Cohen et al. |
| 2012/0196297 | A1 | 8/2012 | Yost et al. |
| 2012/0202698 | A1 | 8/2012 | Van Eijk et al. |
| 2012/0202704 | A1 | 8/2012 | Fan et al. |
| 2012/0220479 | A1 | 8/2012 | Ericsson et al. |
| 2012/0245053 | A1 | 9/2012 | Shirai et al. |
| 2012/0252702 | A1 | 10/2012 | Muratani et al. |
| 2012/0258871 | A1 | 10/2012 | Kozlov et al. |
| 2012/0270305 | A1 | 10/2012 | Reed et al. |
| 2012/0270748 | A1 | 10/2012 | Chee et al. |
| 2012/0279954 | A1 | 11/2012 | Ceremony et al. |
| 2012/0283106 | A1 | 11/2012 | Wang et al. |

(56) References Cited

U.S. PATENT DOCUMENTS

| | | | |
|---|---|---|---|
| 2012/0283829 | A1 | 11/2012 | Temple et al. |
| 2012/0289414 | A1 | 11/2012 | Mitra et al. |
| 2012/0301925 | A1 | 11/2012 | Belyaev |
| 2012/0308445 | A1 | 12/2012 | Roper et al. |
| 2012/0316086 | A1 | 12/2012 | Lin et al. |
| 2012/0322099 | A1 | 12/2012 | Lapen et al. |
| 2013/0005594 | A1 | 1/2013 | Terbrueggen et al. |
| 2013/0005600 | A1 | 1/2013 | Olek |
| 2013/0023433 | A1 | 1/2013 | Luo et al. |
| 2013/0035239 | A1 | 2/2013 | Kong et al. |
| 2013/0040842 | A1 | 2/2013 | Lim et al. |
| 2013/0045473 | A1 | 2/2013 | Duerr et al. |
| 2013/0052331 | A1 | 2/2013 | Kram et al. |
| 2013/0053273 | A1 | 2/2013 | Juncker et al. |
| 2013/0065768 | A1 | 3/2013 | Zheng et al. |
| 2013/0079232 | A1 | 3/2013 | Kain et al. |
| 2013/0096033 | A1 | 4/2013 | Routenberg |
| 2013/0109595 | A1 | 5/2013 | Routenberg |
| 2013/0122516 | A1 | 5/2013 | Hong et al. |
| 2013/0146459 | A1 | 6/2013 | Bazant et al. |
| 2013/0171621 | A1 | 7/2013 | Luo et al. |
| 2013/0195963 | A1 | 8/2013 | Serda et al. |
| 2013/0202718 | A1 | 8/2013 | Pepin et al. |
| 2013/0203100 | A1 | 8/2013 | Otter et al. |
| 2013/0211249 | A1 | 8/2013 | Barnett et al. |
| 2013/0244884 | A1 | 9/2013 | Jacobson et al. |
| 2013/0244895 | A1 | 9/2013 | Voros et al. |
| 2013/0252847 | A1 | 9/2013 | McKenna et al. |
| 2013/0260372 | A1 | 10/2013 | Buermann et al. |
| 2013/0261019 | A1 | 10/2013 | Lin et al. |
| 2013/0302801 | A1 | 11/2013 | Asbury et al. |
| 2013/0338038 | A1 | 12/2013 | Dubridge et al. |
| 2014/0011289 | A1 | 1/2014 | Smith et al. |
| 2014/0011707 | A1 | 1/2014 | Ye et al. |
| 2014/0065609 | A1 | 3/2014 | Hicks et al. |
| 2014/0066318 | A1 | 3/2014 | Frisen et al. |
| 2014/0121118 | A1 | 5/2014 | Warner |
| 2014/0155274 | A1 | 6/2014 | Xie et al. |
| 2014/0155297 | A1 | 6/2014 | Heinz |
| 2014/0162293 | A1 | 6/2014 | Springer et al. |
| 2014/0227705 | A1 | 8/2014 | Vogelstein et al. |
| 2014/0342921 | A1 | 11/2014 | Weiner |
| 2014/0378350 | A1 | 12/2014 | Hindson et al. |
| 2015/0010860 | A1 | 1/2015 | Kataoka et al. |
| 2015/0051085 | A1 | 2/2015 | Vogelstein et al. |
| 2015/0065371 | A1 | 3/2015 | Seppo et al. |
| 2015/0072867 | A1 | 3/2015 | Soldatov |
| 2015/0087027 | A1 | 3/2015 | Makarov et al. |
| 2015/0344942 | A1 | 12/2015 | Frisen et al. |
| 2016/0003812 | A1 | 1/2016 | Porreca et al. |
| 2016/0024576 | A1 | 1/2016 | Chee |
| 2016/0138091 | A1 | 5/2016 | Chee et al. |
| 2016/0145677 | A1 | 5/2016 | Chee et al. |
| 2016/0201125 | A1 | 7/2016 | Samuels et al. |
| 2016/0291006 | A1 | 10/2016 | Trau et al. |
| 2016/0298180 | A1 | 10/2016 | Chee |
| 2016/0304952 | A1 | 10/2016 | Boyden et al. |
| 2016/0333403 | A1 | 11/2016 | Chee |
| 2016/0369066 | A1 | 12/2016 | Seul et al. |
| 2017/0058339 | A1 | 3/2017 | Chee |
| 2017/0058340 | A1 | 3/2017 | Chee |
| 2017/0058345 | A1 | 3/2017 | Chee |
| 2017/0088881 | A1 | 3/2017 | Chee |
| 2017/0166962 | A1 | 6/2017 | Van Eijk et al. |
| 2017/0266667 | A1 | 9/2017 | Mortillaro et al. |
| 2018/0094316 | A1 | 4/2018 | Scott et al. |
| 2018/0105808 | A1 | 4/2018 | Mikkelsen et al. |
| 2018/0112209 | A1 | 4/2018 | Eshoo |
| 2018/0179590 | A1 | 6/2018 | Belgrader et al. |
| 2018/0201980 | A1 | 7/2018 | Chee et al. |
| 2018/0216162 | A1 | 8/2018 | Belhocine et al. |
| 2018/0247017 | A1 | 8/2018 | Van Eijk et al. |
| 2018/0291439 | A1 | 10/2018 | Van Eijk et al. |
| 2018/0334670 | A1 | 11/2018 | Bharadwaj et al. |
| 2019/0002971 | A1 | 1/2019 | Koslover et al. |
| 2019/0017106 | A1 | 1/2019 | Frisen et al. |
| 2019/0024153 | A1 | 1/2019 | Frisen et al. |
| 2019/0024154 | A1 | 1/2019 | Frisen et al. |
| 2019/0064173 | A1 | 2/2019 | Bharadwaj et al. |
| 2019/0177800 | A1 | 6/2019 | Boutet et al. |
| 2019/0203275 | A1 | 7/2019 | Friesen et al. |
| 2019/0264268 | A1 | 8/2019 | Frisen et al. |
| 2019/0360034 | A1 | 11/2019 | Zhou et al. |
| 2019/0367982 | A1 | 12/2019 | Belhocine et al. |
| 2019/0367997 | A1 | 12/2019 | Bent et al. |
| 2020/0109443 | A1 | 4/2020 | Chee |
| 2020/0277663 | A1 | 9/2020 | Ramachandran Iyer et al. |
| 2020/0277664 | A1 | 9/2020 | Frenz |
| 2020/0283852 | A1 | 9/2020 | Oliphant et al. |
| 2020/0354774 | A1 | 11/2020 | Church et al. |
| 2020/0362392 | A1 | 11/2020 | Nolan |
| 2020/0399687 | A1 | 12/2020 | Frisen et al. |
| 2020/0407781 | A1 | 12/2020 | Schnall-Levin et al. |
| 2021/0010068 | A1 | 1/2021 | Chee et al. |
| 2021/0010070 | A1 | 1/2021 | Schnall-Levin et al. |
| 2021/0017583 | A1 | 1/2021 | Chee et al. |
| 2021/0140982 | A1 | 5/2021 | Uytingco |
| 2021/0172007 | A1 | 6/2021 | Chee et al. |
| 2021/0189475 | A1 | 6/2021 | Tentori et al. |
| 2021/0190770 | A1 | 6/2021 | Delaney et al. |
| 2021/0198741 | A1 | 7/2021 | Williams |
| 2021/0199660 | A1 | 7/2021 | Williams et al. |
| 2021/0214785 | A1 | 7/2021 | Stoeckius |
| 2021/0222241 | A1 | 7/2021 | Bharadwaj |
| 2021/0222242 | A1 | 7/2021 | Ramachandran Iyer |
| 2021/0222253 | A1 | 7/2021 | Uytingco |
| 2021/0223227 | A1 | 7/2021 | Stoeckius |
| 2021/0230681 | A1 | 7/2021 | Patterson et al. |
| 2021/0230692 | A1 | 7/2021 | Daugharthy et al. |
| 2021/0237022 | A1 | 8/2021 | Bava |
| 2021/0238581 | A1 | 8/2021 | Mikkelsen et al. |
| 2021/0238664 | A1 | 8/2021 | Bava |
| 2021/0238675 | A1 | 8/2021 | Bava |
| 2021/0238680 | A1 | 8/2021 | Bava |
| 2021/0247316 | A1 | 8/2021 | Bava |
| 2021/0262019 | A1 | 8/2021 | Alvarado Martinez et al. |
| 2021/0277460 | A1 | 9/2021 | Bava |
| 2021/0285036 | A1 | 9/2021 | Yin et al. |
| 2021/0285046 | A1 | 9/2021 | Chell et al. |
| 2021/0292748 | A1 | 9/2021 | Frisen et al. |
| 2021/0292822 | A1 | 9/2021 | Frisen et al. |
| 2021/0317510 | A1 | 10/2021 | Chee et al. |
| 2021/0317524 | A1 | 10/2021 | Lucero et al. |
| 2021/0324457 | A1 | 10/2021 | Ramachandran Iyer et al. |
| 2021/0332424 | A1 | 10/2021 | Schnall-Levin |
| 2021/0332425 | A1 | 10/2021 | Pfeiffer et al. |
| 2021/0348221 | A1 | 11/2021 | Chell et al. |
| 2022/0002791 | A1 | 1/2022 | Frisen et al. |
| 2022/0010367 | A1 | 1/2022 | Ramachandran Iyer et al. |
| 2022/0017951 | A1 | 1/2022 | Ramachandran Iyer et al. |
| 2022/0025446 | A1 | 1/2022 | Shah |
| 2022/0025447 | A1 | 1/2022 | Tentori et al. |
| 2022/0033888 | A1 | 2/2022 | Schnall-Levin et al. |
| 2022/0049293 | A1 | 2/2022 | Frenz et al. |
| 2022/0049294 | A1 | 2/2022 | Uytingco et al. |
| 2022/0064630 | A1 | 3/2022 | Bent et al. |
| 2022/0081728 | A1 | 3/2022 | Williams |
| 2022/0088561 | A1 | 3/2022 | Brenan et al. |
| 2022/0090058 | A1 | 3/2022 | Frisen et al. |
| 2022/0090175 | A1 | 3/2022 | Uytingco et al. |
| 2022/0090181 | A1 | 3/2022 | Gallant et al. |
| 2022/0098576 | A1 | 3/2022 | Dadhwal |
| 2022/0098661 | A1 | 3/2022 | Chew et al. |
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0119869 | A1 | 4/2022 | Ramachandran Iyer et al. |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |
| 2022/0170083 | A1 | 6/2022 | Khaled et al. |
| 2022/0195422 | A1 | 6/2022 | Gallant et al. |

(56) References Cited

U.S. PATENT DOCUMENTS

2022/0195505 A1 6/2022 Frisen et al.
2022/0213526 A1 7/2022 Frisen et al.
2022/0228210 A1 7/2022 Patterson et al.
2022/0241780 A1 8/2022 Tentori et al.
2022/0267844 A1 8/2022 Ramachandran Iyer et al.
2022/0275444 A1 9/2022 Salmanzadeh
2022/0282329 A1 9/2022 Chell et al.
2022/0290217 A1 9/2022 Frenz et al.
2022/0298560 A1 9/2022 Frisen et al.
2022/0325325 A1 10/2022 Chee et al.
2022/0326251 A1 10/2022 Uytingco et al.
2022/0333191 A1 10/2022 Mikkelsen et al.
2022/0333192 A1 10/2022 Uytingco
2022/0333195 A1 10/2022 Schnall-Levin et al.
2022/0334031 A1 10/2022 Delaney et al.
2022/0348905 A1 11/2022 Dadhwal
2022/0348992 A1 11/2022 Stoeckius et al.
2022/0356464 A1 11/2022 Kim et al.
2022/0364163 A1 11/2022 Stahl et al.
2022/0389503 A1 12/2022 Mikkelsen et al.
2022/0389504 A1 12/2022 Chew et al.
2022/0403455 A1 12/2022 Ramachandran Iyer et al.
2022/0404245 A1 12/2022 Chell et al.
2023/0002812 A1 1/2023 Stoeckius et al.
2023/0014008 A1 1/2023 Shastry
2023/0017773 A1 1/2023 Kim et al.
2023/0031305 A1 2/2023 Neuta et al.
2023/0033960 A1 2/2023 Gallant et al.
2023/0034039 A1 2/2023 Shahjamali
2023/0034216 A1 2/2023 Bava
2023/0042817 A1 2/2023 Mignardi
2023/0047782 A1 2/2023 Tentori et al.
2023/0056549 A1 2/2023 Dadhwal
2023/0064372 A1 3/2023 Chell et al.
2023/0069046 A1 3/2023 Chew et al.
2023/0077364 A1 3/2023 Patterson et al.
2023/0080543 A1 3/2023 Katiraee et al.
2023/0081381 A1 3/2023 Chew et al.
2023/0100497 A1 3/2023 Frisen et al.
2023/0111225 A1 4/2023 Chew et al.
2023/0113230 A1 4/2023 Kim et al.
2023/0126825 A1 4/2023 Nagendran et al.
2023/0129552 A1 4/2023 Ramachandran Iyer
2023/0135010 A1 5/2023 Tentori et al.
2023/0143569 A1 5/2023 Iyer et al.
2023/0145575 A1 5/2023 Gallant et al.
2023/0147726 A1 5/2023 Hadrup et al.
2023/0159995 A1 5/2023 Iyer et al.
2023/0160008 A1 5/2023 Chell et al.
2023/0175045 A1 6/2023 Katsori et al.
2023/0183684 A1 6/2023 Gallant et al.
2023/0183785 A1 6/2023 Frisen et al.
2023/0194469 A1 6/2023 Tentori et al.
2023/0194470 A1 6/2023 Kim et al.
2023/0203478 A1 6/2023 Kim et al.
2023/0212650 A1 7/2023 Chew et al.
2023/0220368 A1 7/2023 Kim
2023/0220454 A1 7/2023 Bent et al.
2023/0220455 A1 7/2023 Galonska et al.
2023/0227811 A1 7/2023 Dadhwal
2023/0228762 A1 7/2023 Uytingco et al.
2023/0242973 A1 8/2023 Frisen et al.
2023/0242976 A1 8/2023 Tentori et al.
2023/0265488 A1 8/2023 Gohil et al.
2023/0265489 A1 8/2023 Uytingco et al.
2023/0265491 A1 8/2023 Tentori et al.
2023/0267625 A1 8/2023 Tentori et al.
2023/0279474 A1 9/2023 Katiraee
2023/0279477 A1 9/2023 Kvastad et al.
2023/0279481 A1 9/2023 Marrache et al.
2023/0287399 A1 9/2023 Gallant et al.
2023/0287475 A1 9/2023 Chell et al.
2023/0287481 A1 9/2023 Katsori et al.
2023/0295699 A1 9/2023 Sukovich et al.
2023/0295722 A1 9/2023 Bharadwaj
2023/0304072 A1 9/2023 Gohil et al.
2023/0304074 A1 9/2023 Chee et al.
2023/0304078 A1 9/2023 Frisen et al.
2023/0313279 A1 10/2023 Giacomello et al.
2023/0323340 A1 10/2023 Dadhwal
2023/0323434 A1 10/2023 Yin et al.
2023/0323447 A1 10/2023 Schnall-Levin et al.
2023/0323453 A1 10/2023 Stoeckius
2023/0332138 A1 10/2023 Kim et al.
2023/0332212 A1 10/2023 Chew et al.
2023/0332227 A1 10/2023 Ramachandran Iyer
2023/0332247 A1 10/2023 Singh et al.
2023/0351619 A1 11/2023 Tentori et al.
2023/0358733 A1 11/2023 Chee
2023/0366008 A1 11/2023 Chew et al.
2023/0383285 A1 11/2023 Kim et al.
2023/0383344 A1 11/2023 Stoeckius
2023/0392204 A1 12/2023 Chell et al.
2023/0393071 A1 12/2023 Bava
2023/0407404 A1 12/2023 Baumgartner et al.
2023/0416808 A1 12/2023 Sukovich et al.
2023/0416850 A1 12/2023 Singh et al.
2024/0002931 A1 1/2024 Bava
2024/0011090 A1 1/2024 Chew et al.
2024/0018572 A1 1/2024 Mignardi
2024/0018575 A1 1/2024 Gallant et al.
2024/0018589 A1 1/2024 Schnall-Levin et al.
2024/0026445 A1 1/2024 Ramachandran Iyer et al.
2024/0033743 A1 2/2024 Tentori et al.
2024/0035937 A1 2/2024 Cox et al.
2024/0043908 A1 2/2024 Chew et al.
2024/0043925 A1 2/2024 Bent et al.
2024/0052343 A1 2/2024 Gallant et al.
2024/0053351 A1 2/2024 Uytingco et al.
2024/0060115 A1 2/2024 Chee et al.
2024/0067953 A1 2/2024 Mikkelsen et al.
2024/0068016 A1 2/2024 Frisen et al.
2024/0068017 A1 2/2024 Lundeberg et al.
2024/0076723 A1 3/2024 Mignardi
2024/0080346 A1 3/2024 Engblom et al.
2024/0084365 A1 3/2024 Frisen et al.
2024/0084366 A1 3/2024 Chee
2024/0084383 A1 3/2024 Ramachandran Iyer et al.
2024/0093274 A1 3/2024 Frisen et al.
2024/0093290 A1 3/2024 Stahl et al.
2024/0110228 A1 4/2024 Uytingco et al.
2024/0124933 A1 4/2024 Chell et al.
2024/0125772 A1 4/2024 Delaney et al.
2024/0141327 A1 5/2024 Kim et al.
2024/0158838 A1 5/2024 Alvarado Martinez et al.
2024/0175080 A1 5/2024 Galonska et al.
2024/0182968 A1 6/2024 Bava
2024/0191286 A1 6/2024 Boutet et al.
2024/0200121 A1 6/2024 Boutet
2024/0209425 A1 6/2024 Yin et al.
2024/0218427 A1 7/2024 Sukovich et al.
2024/0218432 A1 7/2024 Mielinis
2024/0219701 A1 7/2024 Tentori et al.
2024/0253036 A1 8/2024 Kim et al.
2024/0263218 A1 8/2024 Katiraee et al.
2024/0271190 A1 8/2024 Stoeckius et al.
2024/0271195 A1 8/2024 Mikhaiel et al.
2024/0279747 A1 8/2024 Williams
2024/0287600 A1 8/2024 Iyer et al.
2024/0294971 A1 9/2024 Galonska
2024/0294974 A1 9/2024 Galonska et al.
2024/0294975 A1 9/2024 Lin et al.
2024/0301488 A1 9/2024 Stoeckius
2024/0301489 A1 9/2024 Chew et al.
2024/0360494 A1 10/2024 Costa et al.
2024/0368711 A1 11/2024 Giacomello et al.
2024/0377297 A1 11/2024 Cox et al.
2024/0385088 A1 11/2024 Kim et al.
2024/0392349 A1 11/2024 Frisen et al.
2024/0392352 A1 11/2024 Stahl et al.
2024/0392353 A1 11/2024 Engblom et al.
2024/0401109 A1 12/2024 Kim et al.
2024/0401117 A1 12/2024 Bava
2024/0401118 A1 12/2024 Tentori et al.

(56) References Cited

U.S. PATENT DOCUMENTS

| | | | |
|---|---|---|---|
| 2024/0404301 | A1 | 12/2024 | Li et al. |
| 2024/0408593 | A1 | 12/2024 | Kim et al. |
| 2024/0416315 | A1 | 12/2024 | Bava |
| 2024/0417783 | A1 | 12/2024 | Chew et al. |
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019689 | A1 | 1/2025 | Galonska et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |
| 2025/0179475 | A1 | 6/2025 | Borgstrom et al. |
| 2025/0182305 | A1 | 6/2025 | Tentori et al. |
| 2025/0182503 | A1 | 6/2025 | Li et al. |
| 2025/0188526 | A1 | 6/2025 | Sukovich et al. |
| 2025/0189483 | A1 | 6/2025 | Kim et al. |
| 2025/0197847 | A1 | 6/2025 | Kim et al. |
| 2025/0197938 | A1 | 6/2025 | Bjorninen |
| 2025/0207125 | A1 | 6/2025 | Gupta et al. |
| 2025/0207195 | A1 | 6/2025 | Chell et al. |
| 2025/0208115 | A1 | 6/2025 | Bent |
| 2025/0215482 | A1 | 7/2025 | Mignardi et al. |
| 2025/0215484 | A1 | 7/2025 | Ramachandran Iyer et al. |
| 2025/0216300 | A1 | 7/2025 | Delaney et al. |
| 2025/0216303 | A1 | 7/2025 | Cox et al. |
| 2025/0223633 | A1 | 7/2025 | Frenz et al. |
| 2025/0230487 | A1 | 7/2025 | Chee et al. |
| 2025/0230498 | A1 | 7/2025 | Katiraee |
| 2025/0250621 | A1 | 8/2025 | Galonska et al. |
| 2025/0250632 | A1 | 8/2025 | Mignardi et al. |
| 2025/0257393 | A1 | 8/2025 | Katiraee et al. |
| 2025/0263791 | A1 | 8/2025 | Bava |
| 2025/0264411 | A1 | 8/2025 | Bava |
| 2025/0283154 | A1 | 9/2025 | Iyer et al. |
| 2025/0283157 | A1 | 9/2025 | Uytingco et al. |
| 2025/0297308 | A1 | 9/2025 | Tentori |
| 2025/0313890 | A1 | 10/2025 | Lundeberg et al. |
| 2025/0313892 | A1 | 10/2025 | Stoeckius |
| 2025/0340933 | A1 | 11/2025 | Giacomello et al. |
| 2025/0354931 | A1 | 11/2025 | Shah et al. |
| 2025/0369037 | A1 | 12/2025 | Gupta |
| 2025/0376676 | A1 | 12/2025 | Kim et al. |
| 2025/0376719 | A1 | 12/2025 | Shah |
| 2025/0382665 | A1 | 12/2025 | Frenz et al. |
| 2026/0002202 | A1 | 1/2026 | Schnall-Levin et al. |
| 2026/0009784 | A1 | 1/2026 | Stoeckius |
| 2026/0015653 | A1 | 1/2026 | Chew et al. |
| 2026/0022419 | A1 | 1/2026 | Bent et al. |
| 2026/0049349 | A1 | 2/2026 | Gallant et al. |
| 2026/0055443 | A1 | 2/2026 | Tentori et al. |
| 2026/0071262 | A1 | 3/2026 | Yin et al. |
| 2026/0103754 | A1 | 4/2026 | Schnall-Levin et al. |
| 2026/0117286 | A1 | 4/2026 | Katiraee et al. |
| 2026/0117289 | A1 | 4/2026 | Kim |
| 2026/0117298 | A1 | 4/2026 | Doddridge |
| 2026/0117302 | A1 | 4/2026 | Chell et al. |
| 2026/0124615 | A1 | 5/2026 | Kim et al. |
| 2026/0177299 | A1 | 6/2026 | Schroeder et al. |

FOREIGN PATENT DOCUMENTS

| | | | |
|---|---|---|---|
| CN | 1273609 | | 11/2000 |
| CN | 1425133 | | 6/2003 |
| CN | 1537953 | | 10/2004 |
| CN | 1680594 | | 2/2005 |
| CN | 1680604 | | 10/2005 |
| CN | 1749752 | | 3/2006 |
| CN | 1813059 | | 8/2006 |
| CN | 1898398 | | 1/2007 |
| CN | 1934452 | | 3/2007 |
| CN | 1981188 | | 6/2007 |
| CN | 101142325 | | 3/2008 |
| CN | 101205560 | | 6/2008 |
| CN | 101221182 | | 7/2008 |
| CN | 101405400 | | 4/2009 |
| CN | 101432698 | | 5/2009 |
| CN | 101460633 | | 6/2009 |
| CN | 101522915 | | 9/2009 |
| CN | 101809165 | | 8/2010 |
| CN | 102216456 | | 10/2011 |
| CN | 102232189 | | 11/2011 |
| CN | 202548048 | | 11/2012 |
| CN | 102851369 | | 1/2013 |
| CN | 102947330 | | 2/2013 |
| CN | 105441549 | | 3/2016 |
| EP | 0901631 | | 3/1999 |
| EP | 0961110 | | 12/1999 |
| EP | 1160563 | | 12/2001 |
| EP | 1782737 | | 5/2007 |
| EP | 1878502 | | 1/2008 |
| EP | 1910562 | | 4/2008 |
| EP | 1923471 | | 5/2008 |
| EP | 1929039 | | 6/2008 |
| EP | 1966393 | | 9/2008 |
| EP | 2002017 | | 12/2008 |
| EP | 2130913 | | 12/2009 |
| EP | 2161336 | | 3/2010 |
| EP | 2292788 | | 3/2011 |
| EP | 2302070 | | 3/2011 |
| EP | 2350648 | | 8/2011 |
| EP | 2363504 | | 9/2011 |
| EP | 2580351 | | 4/2013 |
| EP | 2789696 | | 10/2014 |
| EP | 2963127 | | 1/2016 |
| EP | 3045544 | | 7/2016 |
| EP | 3239304 | | 11/2017 |
| EP | 1846164 | | 5/2018 |
| JP | 2007-014297 | | 1/2007 |
| JP | 2007-074967 | | 3/2007 |
| JP | 2009-036694 | | 2/2009 |
| JP | 2011-182702 | | 9/2011 |
| JP | 2013-544498 | | 12/2013 |
| JP | 2014-217381 | | 11/2014 |
| KR | 10-2009-0000812 | | 1/2009 |
| KR | 10-2009-0081260 | | 7/2009 |
| RU | 2145635 | | 2/2000 |
| RU | 2270254 | | 2/2006 |
| RU | 2410439 | C1 | 1/2011 |
| WO | WO 1989/010977 | | 11/1989 |
| WO | WO 1991/006678 | | 5/1991 |
| WO | WO 1993/004199 | | 3/1993 |
| WO | WO 1995/023875 | | 9/1995 |
| WO | WO 1995/025116 | | 9/1995 |
| WO | WO 1995/035505 | | 12/1995 |
| WO | WO 1996/007669 | | 3/1996 |
| WO | WO 1997/031256 | | 8/1997 |
| WO | WO 1997/047640 | | 12/1997 |
| WO | WO 1998/010277 | | 3/1998 |
| WO | WO 1998/044151 | | 10/1998 |
| WO | WO 1999/032654 | | 7/1999 |
| WO | WO 1999/044062 | | 9/1999 |

(56) References Cited

FOREIGN PATENT DOCUMENTS

| | | |
|---|---|---|
| WO | WO 1999/044063 | 9/1999 |
| WO | WO 1999/049082 | 9/1999 |
| WO | WO 1999/063385 | 12/1999 |
| WO | WO 1999/067641 | 12/1999 |
| WO | WO 2000/017390 | 3/2000 |
| WO | WO 2000/018957 | 4/2000 |
| WO | WO 2000/024940 | 5/2000 |
| WO | WO 2000/075373 | 12/2000 |
| WO | WO 2001/006012 | 1/2001 |
| WO | WO 2001/007915 | 2/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/024952 | 3/2002 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2002/088396 | 11/2002 |
| WO | WO 2003/002979 | 1/2003 |
| WO | WO 2003/003810 | 1/2003 |
| WO | WO 2003/008538 | 1/2003 |
| WO | WO 2003/010176 | 2/2003 |
| WO | WO 2003/020261 | 3/2003 |
| WO | WO 2003/076666 | 9/2003 |
| WO | WO 2003/077851 | 9/2003 |
| WO | WO 2003/102233 | 12/2003 |
| WO | WO 2003/106973 | 12/2003 |
| WO | WO 2004/015080 | 2/2004 |
| WO | WO 2004/028955 | 4/2004 |
| WO | WO 2004/055159 | 7/2004 |
| WO | WO 2004/067759 | 8/2004 |
| WO | WO 2004/081225 | 9/2004 |
| WO | WO 2004/087323 | 10/2004 |
| WO | WO 2004/108268 | 12/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/067648 | 7/2005 |
| WO | WO 2005/084367 | 9/2005 |
| WO | WO 2005/113804 | 12/2005 |
| WO | WO 2006/020515 | 2/2006 |
| WO | WO 2006/056861 | 6/2006 |
| WO | WO 2006/064199 | 6/2006 |
| WO | WO 2006/065597 | 6/2006 |
| WO | WO 2006/074351 | 7/2006 |
| WO | WO 2006/081021 | 8/2006 |
| WO | WO 2006/081222 | 8/2006 |
| WO | WO 2006/084130 | 8/2006 |
| WO | WO 2006/117541 | 11/2006 |
| WO | WO 2006/124771 | 11/2006 |
| WO | WO 2006/137733 | 12/2006 |
| WO | WO 2007/000669 | 1/2007 |
| WO | WO 2007/010251 | 1/2007 |
| WO | WO 2007/030373 | 3/2007 |
| WO | WO 2007/037678 | 4/2007 |
| WO | WO 2007/041689 | 4/2007 |
| WO | WO 2007/053719 | 5/2007 |
| WO | WO 2007/060599 | 5/2007 |
| WO | WO 2007/073165 | 6/2007 |
| WO | WO 2007/073171 | 6/2007 |
| WO | WO 2007/073271 | 6/2007 |
| WO | WO 2007/076128 | 7/2007 |
| WO | WO 2007/076726 | 7/2007 |
| WO | WO 2007/114693 | 10/2007 |
| WO | WO 2007/120241 | 10/2007 |
| WO | WO 2007/139766 | 12/2007 |
| WO | WO 2007/145612 | 12/2007 |
| WO | WO 2008/005673 | 1/2008 |
| WO | WO 2008/022332 | 2/2008 |
| WO | WO 2008/069906 | 6/2008 |
| WO | WO 2008/075086 | 6/2008 |
| WO | WO 2008/157801 | 12/2008 |
| WO | WO 2009/029937 | 3/2009 |
| WO | WO 2009/032167 | 3/2009 |
| WO | WO 2009/036525 | 3/2009 |
| WO | WO 2009/086487 | 7/2009 |
| WO | WO 2009/137521 | 11/2009 |
| WO | WO 2009/152928 | 12/2009 |
| WO | WO 2009/156725 | 12/2009 |
| WO | WO 2010/019826 | 2/2010 |
| WO | WO 2010/027870 | 3/2010 |
| WO | WO 2010/053587 | 5/2010 |
| WO | WO 2010/060439 | 6/2010 |
| WO | WO 2010/062310 | 6/2010 |
| WO | WO 2010/088517 | 8/2010 |
| WO | WO 2010/100265 | 9/2010 |
| WO | WO 2010/110929 | 9/2010 |
| WO | WO 2010/126614 | 11/2010 |
| WO | WO 2010/127186 | 11/2010 |
| WO | WO 2011/002779 | 1/2011 |
| WO | WO 2011/008502 | 1/2011 |
| WO | WO 2011/014879 | 2/2011 |
| WO | WO 2011/062933 | 5/2011 |
| WO | WO 2011/071943 | 6/2011 |
| WO | WO 2011/102903 | 8/2011 |
| WO | WO 2011/127006 | 10/2011 |
| WO | WO 2011/127099 | 10/2011 |
| WO | WO 2011/143583 | 11/2011 |
| WO | WO 2011/155833 | 12/2011 |
| WO | WO 2012/022975 | 2/2012 |
| WO | WO 2012/049316 | 4/2012 |
| WO | WO 2012/058096 | 5/2012 |
| WO | WO 2012/061832 | 5/2012 |
| WO | WO 2012/071428 | 5/2012 |
| WO | WO 2012/083225 | 6/2012 |
| WO | WO 2012/129242 | 9/2012 |
| WO | WO 2012/139110 | 10/2012 |
| WO | WO 2012/140224 | 10/2012 |
| WO | WO 2012/142213 | 10/2012 |
| WO | WO 2012/148477 | 11/2012 |
| WO | WO 2012/148497 | 11/2012 |
| WO | WO 2012/159089 | 11/2012 |
| WO | WO 2012/168003 | 12/2012 |
| WO | WO 2013/022807 | 2/2013 |
| WO | WO 2013/033271 | 3/2013 |
| WO | WO 2013/040257 | 3/2013 |
| WO | WO 2013/090390 | 6/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150083 | 10/2013 |
| WO | WO 2013/025952 | 12/2013 |
| WO | WO 2014/060483 | 4/2014 |
| WO | WO 2014/210223 | 12/2014 |
| WO | WO 2014/210225 | 12/2014 |
| WO | WO 2014/210353 | 12/2014 |
| WO | WO 2017/013170 | 1/2017 |
| WO | WO 2020/041148 | 2/2020 |
| WO | WO 2020/076979 | 4/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/167862 | 8/2020 |
| WO | WO 2020/176882 | 9/2020 |
| WO | WO 2020/190509 | 9/2020 |
| WO | WO 2020/198071 | 10/2020 |
| WO | WO 2020/219901 | 10/2020 |
| WO | WO 2021/091611 | 5/2021 |
| WO | WO 2021/092433 | 5/2021 |
| WO | WO 2021/097255 | 5/2021 |
| WO | WO 2021/133842 | 7/2021 |
| WO | WO 2021/133849 | 7/2021 |
| WO | WO 2021/142233 | 7/2021 |

(56) References Cited

FOREIGN PATENT DOCUMENTS

| | | |
|---|---|---|
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/087273 | 4/2022 |
| WO | WO 2022/098810 | 5/2022 |
| WO | WO 2022/099037 | 5/2022 |
| WO | WO 2022/103712 | 5/2022 |
| WO | WO 2022/109181 | 5/2022 |
| WO | WO 2011/019964 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |
| WO | WO 2026/024934 | 1/2026 |

OTHER PUBLICATIONS

Bibikova et al., "Quantitative gene expression profiling in formalin-fixed paraffin-embedded tissues using universal bead arrays," The American Journal of Pathology, Nov. 1, 2004, 165(5): 1799- 1807.

Cai et al., "Glutathione-mediated shedding of PEG layers based on disulfide-linked catiomers for DNA delivery," J. Mater. Chem., Sep. 20, 2011, 21(38):14639-14645.

Fan et al., "A versatile assay for high-throughput gene expression profiling on universal array matrices," Genome Research, May 1, 2004, 14(5):878-885.

Ha et al., "Self-assembly hollow nanosphere for enzyme encapsulation," Soft Matter, Feb. 11, 2010, 6, 1405-1408, 10 pages.

Holscher et al., "Application of Laser-Assisted Microdissection for Tissue and Cell-Specific Analysis of RNA," Progress in Botany, Jan. 2008, 69(3):141-167.

Jeffers, "A Basic Subroutine for Geary's Contiguity Ratio," J. Royal Stat. Society, Series D, Dec. 1973, 22(4):299-302.

Ju et al., "Supramolecular dendrimer capsules by cooperative binding," Chem. Commun., Jan. 7, 2011, 47(1):268-270, 8 pages.

Kim, "Development of Microdevices for Applications to Bioanalysis," Dissertation for the degree of Doctor of Philosophy, University of Texas at Austin, Aug. 2007, 176 pages.

Kuiper et al., "Enzymes containing porous polymersomes as nano reaction vessels for cascade reactions," Org. Biomol, Chem, Oct. 15, 2008, 6(23):4315-4318.

Li et al., "Beyond Moran's I: Testing for Spatial Dependence Based on the Spatial Autoregressive Model," Geographical Analysis, Sep. 18, 2007, 39(4):357-375.

Liu et al., "Preparation and Characterization of Temperature-Sensitive Poly(N-isopropylacrylamide)-b-poly(d,1-lactide) Microspheres for Protein Delivery," Biomacromolecules, 2003, 4(6):1784-1793.

Miller et al., "Rapid and Efficient Enzyme Encapsulation in a Dendrimer Silica Nanocomposite," Macromolecular Bioscience, Oct. 25, 2006, 6(10):839-845.

Rahimi et al., "Synthesis and Characterization of Thermo-Sensitive Nanoparticles for Drug Delivery Applications," J. Biomed. Nanotechnol. Dec. 2008, 4(4):482-490, 19 pages.

Hamers-Casterman et al., "Naturally occurring antibodies devoid of light chains," Nature, 1993, 363:446-448.

He et al., "Ribosome display: Cell-free protein display technology," Briefings in Functional Genomics and Proteomics, Jul. 2002, 204-212.

Illumina Gene Expression Profiling, "Whole-Genome Expression Analysis Using the Sentrix Human-6 and HumanRef-8 Expression BeadChips," Illumina, 2005, pp. 1-8.

Lee et al., "Hydrogels for Tissue Engineering," Chemical Reviews, 2001, 101(7): 1869-1879.

Life Technologies, "Illumina TotalPrep RNA Amplification Kit," Ambion, 2011, 17 pages.

Verma et al., "Modified Oligonucleotides: Synthesis and Strategy for Users," Annual Review of Biochemistry, 1998, 67(1):99-134.

Fiandaca et al., "Self-Reporting PNA/DNA Primers for PCR Analysis," Genome Research, Apr. 2001, 11:609-613.

Heiter et al., "Site-Specific DNA-nicking Mutants of the Heterodimeric Restriction Endonuclease R.BbvC," J. Mol. Biol., 2005, 348:631-40.

Higgins et al., "The nicking endonuclease N.BstNBI is closely related to Type IIs restriction endonucleases MlyI and PleI," Nucleic Acids Res., 2001, 29:2492-2501.

Kong et al., "Duplex probes: a new approach for the detection of specific nucleic acids in homogenous assays," Analytics Chimica Acta, Sep. 2003, 491:135-143, 16 pages.

Morgan et al., "Characterization of the specific DNA nicking activity of restriction endonuclease N. BstNBI," Biol. Chem., 2000, 381:1123-1125.

Park et al., "Detection of Hepatitis C Virus RNA Using Ligation-Dependent Polymerase Chain Reaction in Formalin-Fixed, Paraffin-Embedded Liver Tissues," American Journal of Pathology, Nov. 5, 1996, 149(5):1485-1491.

Pringle et al., "In situ hybridization demonstration of poly-adenylated RNA sequences in formalin- fixed paraffin sections

(56) References Cited

OTHER PUBLICATIONS using a biotinylated oligonucleotide poly d(T) probe," Journal of Pathology, Aug. 1989, 158:279-286.
Rasila et al., "Flexibility in MuA transposase family protein structures: functional mapping with scanning mutagenesis and sequence alignment of protein homologues," PLoS ONE, 2012, 7(5): e37922, 14 pages.
Samuelson et al., "The isolation of strand-specific nicking endonucleases from a randomized SapI expression library," Nucleic Acids Res., 2004, 32:3661-3671.
Villemejane et al., "Physical methods of nucleic acid transfer: general concepts and applications," British Journal of Pharmacology, 2009, 157:207-219.
Walker et al., "Isothermal in vitro amplification of DNA by a restriction enzyme/DNA polymerase system," Proc. Natl. Acad. Sci. USA, 1992, 89:392-396.
Wang "Preparation of DNA substrates for in vitro mismatch repair," Mol. Biotechnol., 2000, 15:97-104.
Wolf et al., "tadA, an essential tRNA-specific adenosine deaminase from *Escherichia coli*," EMBO J., Jul. 15, 2002, 21(14):3841-3851.
Xu et al., "Engineering a nicking endonuclease N.AlwI by domain swapping," Proc. Natl. Acad. Sci. USA, 2001, 98:12990-12995.
Zhu et al., "Engineering strand-specific DNA nicking enzymes from the type IIS restriction endonucleases BsaI, BsmBI, and BsmAI," J. Mol. Biol., 2004, 337:573-583.
AJCC, "25 Lungs and 26 Pleural Mesothelioma," AJCC Cancer Staging Manual 7th Ed., Springer, 2010, pp. 253-278, 38 pages.
Berent et al., "Comparison of oligonucleotide and long DNA fragments as probes in DNA and RNA dot, Southern, Northern, colony and plaque hybridizations," Biotechniques, 1985, 3(3):208-220 (Abstract Only).
Cardullo et al., "Detection of nucleic acid hybridization by nonradiative fluorescence resonance energy transfer," PNAS, Dec. 1, 1988, 85:8790-8794.
Crisalli et al., "Multi-Path Quenchers: Efficient Quenching of Common Fluorophores," Bioconjug Chem., Oct. 28, 2011, 22(11): 2345-2354.
Falconnet et al., "Rapid, Sensitive and Real-Time Multiplexing Platform for the Analysis of Protein and Nucleic-Acid Biomarkers," Anal. Chem., Jan. 7, 2015, 87:1582-1589.
Friedman et al., "The synthesis of high yields of full-length reverse transcripts of globin mRNA," Nucleic Acids Res., Oct. 1, 1977, 4(10):3455-3471.
Howell et al., "iFRET: An Improved Fluorescence System for DNA-Melting Analysis," Genome Research, 2002, 12:1401-1407.
Lin et al., "Replication of DNA microarrays from zip code masters," J. Am. Chem. Soc., 2006, 128(10):3268-3272.
Nuovo, "In situ detection of microRNAs in paraffin embedded, formalin fixed tissues and the co-localization of their putative targets," Methods, 2010, 52(4):307-315.
Stougaard et al., "In situ detection of non-polyadenylated RNA molecules using Turtle Probes and target primed rolling circle Prins," Bmc Biotechnology, Dec. 18, 2007, 7(69):1-10.
Tang et al., "mRNA-Seq whole-transcriptome analysis of a single cell," Nat Methods, 2009, 6:377-382.
Yang et al., "Nucleoside alpha-Thiotriphosphates, Polymerases and the Exonuclease III Analysis of Oligonucleotides Containing Phosphorothioate Linkages," Nucleic Acids Research, Apr. 22, 2007, 35(9):3118-3127.
Yao et al., "Influence of laser parameters on nanoparticle-induced membrane permeabilization," Journal of Biomedical Optics, 2009, 14(5):054034, 7 pages.
Crisalli et al., "Water-soluble Organocatalysts for Hydrazone and Oxime Formation," J Org Chem, Feb. 1, 2013, 78(3):1184-1189, 20 pages (Author Manuscript).
Devereux et al., "A comprehensive set of sequence analysis programs for the VAX," Nucleic Acids Res., 1984, 12:387-395.
Illumina, "M1_SamplePrepSlides," Slides of Broad/Illumina Genome Analyzer Boot Camp, Feb. 2010, 76 pages.
Illumina, "M2 Cluster Generation," Slides of Broad/Illumina Genome Analyzer (GA) Boot Camp, Feb. 2010, 45 pages.
Illumina, "M3_Sequencing," Slides of Broad/Illumina Genome Analyzer (GA) Boot Camp, Feb. 2010, 73 pages.
Kim et al., "Replication of DNA Microarrays Prepared by In Situ Oligonucleotide Polymerization and Mechanical Transfer," Anal Chem., 2007, 79:7267-7274.
Kuhn et al., "A novel, high-performance random array platform for quantitative gene expression profiling," Genome Res, 2004, 14:2347-2356.
Michael et al., "Randomly Ordered Addressable High-Density Optical Sensor Arrays," Analytical Chemistry, American Chemical Society, Apr. 1998, 70:1242-1248.
Zimmerman et al., "Chapter 13, Imaging of Cells and Tissue with Mass Spectrometry," Methods in Cell Biology, Biophysical Tools for Biologists, vol. Two: In Vivo Techniques, Jan. 2008, 89:361-390.
Bates et al., "Block copolymers-designer soft materials," Phys Today, Feb. 2000, 52:32-8.
Brown et al., "Multiplex Three-Dimensional Brain Gene Expression Mapping in a Mouse Model of Parkinson's Disease," Genome Research, 2002, 12:868-884.
Chapin et al., "Rapid microRNA Profiling on Encoded Gel Microparticles," Angew Chem Int Ed Engl., 2011, 50(10):2289-2293.
Eberwine et al., "Complementary DNA Synthesis in Situ: Methods and Applications," Methods in Enzymology, 1992, 216:80-100.
Fox, "Applications of Ultra-high-Throughput Sequencing," Plant Systems Biology, Methods in Molecular Biology, Belostotsky (ed.), Humana Press, 2009, 553:79-108.
Gerry et al., "Universal DNA Microarray Method for Multiplex Detection of Low Abundance Point Mutations, " J. Mol. Biol., 1999, 292:251-262.
Grigoryev, "How DNA microarrays are built," Bitesize Bio, first published Jul. 13, 2011, updated Oct. 2021, retrieved from URL <https://bitesizebio.com/7206/introduction-to-dna-microarrays/#:~:text=Microarrays%20evolved%20from%20a%20technique%20known%20as%20Southern,were%20constructed%20by%20immobilizing%20cDNAs%20onto%20filter%20paper.>, 11 pages.
Gruttadauria et al., "Supported proline and proline-derivatives as recyclable organocatalysts," Chemical Society Reviews, Aug. 1, 2008, 37(8):1666-1688.
Harold, "Molecules into Cells: Specifying Spatial Architecture," Microbiology and Molecular Biology Reviews, Dec. 2005, 69(4):544-564.
Hewitt et al., "Tissue Handling and Specimen Preparation in Surgical Pathology," Arch. Pathol. Lab. Med., 2008, 132:1929-1935.
Hong et al., "Background-Free Detection of Single 5 nm Nanoparticles through Interferometric Cross-Polarization Microscopy," Nano Letters, Jan. 4, 2011, 11(2):541-547.
Howell et al., "Glycosylases and AP-cleaving enzymes as a general tool for probe-directed cleavage of ssDNA targets," Nucleic Acids Research, Jan. 15, 2010, 38(7):e99, 10 pages.
Kuhn et al., "Poly(A) Tail Length Is Controlled by the Nuclear Poly(A)-binding Protein Regulating the Interaction between Poly(A) Polymerase and the Cleavage and Poladenylation Specificity Factor," The Journal of Biologic Chemistry, Aug. 21, 2009, 284(34):22803-22814.
Ligasová et al., "In situ reverse transcription: the magic of strength and anonymity," Nucleic Acids Research, 2010, 38(16):e167.
Moses et al., "Museum of spatial transcriptomics," Nature Methods, May 2022, 19:534-546.
Parameswaran et al., "A pyrosequencing-tailored nucleotide barcode design unveils opportunities for largescale sample multiplexing," Nucleic Acids Research, 2007, 35(19):e130.
Proudfoot et al., "Integrating mRNA Processing with Transcription," Cell, Feb. 22, 2002, 108:501-512.
Qiu et al., "Mutation detection using Surveyor nuclease," Biotechniques, Apr. 2004, 36(4):702-707.
Rusk, "Tracing Cell Lineage with 5hmC," Nature Methods, 2016, 13:710-711.
Scicchitano et al., "Preliminary Comparison of Quantity, Quality, and Microarray Performance of RNA Extracted From Formalin-

(56) References Cited

OTHER PUBLICATIONS fixed, Paraffin-embedded, and Unfixed Frozen Tissue Samples," J. Histochemistry & Cytochemistry, 2006, 54(11):1229-1237.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Science, Jun. 2016, Supplementary Materials, 353(6294):78-82, 41 pages.
Tecott et al., "In Situ Transcription: Specific Synthesis of Complementary DNA in Fixed Tissue Sections," Science, 1988, 240:1661-1664.
Trevino et al., "DNA Microarrays: a Powerful Genomic Tool for Biomedical and Clinical Research," Mol Med, 2007, 13(9-10):527-541.
Voelkerding et al., "Next-Generation Sequencing: From Basic Research to Diagnostics," Clinical Chemistry, 2009, 55(4):641-658.
Yamamoto et al., "Generation of stable co-cultures of vascular cells in a honeycomb alginate scaffold," Tissue Eng Part A, Jan. 1, 2010, 16(1):299-308.
Zhang et al., "A self-assembly pathway to aligned monodomain gels," Nat Mater, Jul. 2010, 9(7):594-601, 12 pages (Author Manuscript).
Zhao et al., "Ultrasensitive DNA detection using highly fluorescent bioconjugated nanoparticles," Journal American Chemical Society, 2003, 125:11474-11475.
Baerwald et al., "Discovery of genes implicated in whirling disease infection and resistance in rainbow trout using genome-wide expression profiling," BMC Genomics, Jan. 24, 2008, 9(1):37, 11 pages.
Bandiera et al., "Nuclear Outsourcing of RNA Interference Components to Human Mitochondria," PLoS ONE, Jun. 2011, 6(6):e20746, 1-16.
Dedeoglu et al., "On the Source of Asymmetry in Image Registration Problems," Technical Report, 2005, retrieve from URL<https://www.ri.cmu.edu/pub_files/pub4/dedeoglu_goksel_2005_1/dedeoglu_goksel_2005_1.pdf >, 18 pages.
Marsden et al., "3D small-molecule microarrays," Chem. Commun., 2009, pp. 7107-7109.
Pawloski, "Photolithographic synthesis of high-density DNA probe arrays: Challenges and opportunities," J. Vac. Sci. Technol. B, 2007, 25:2537-2546.
Sel et al., "Feasibility of Employing Model-Based Optimization of Pulse Amplitude and Electrode Distance for Effective Tumor Electropermeabilization," IEEE Transactions on Biomedical Engineering, May 2007, 54(5):773-781.
Shastry, "SNPs in disease gene mapping, medicinal drug development and evolution," J. Hum. Genet., 2007, 52:871-880.
Wu et al., "Detection DNA Point Mutation with Rolling-Circle Amplification Chip," Bioinformatics & Biomed Eng Conference, Piscataway, NJ, 2010, pp. 1-4.
Altman et al., "Phenotypic Analysis of Antigen-Specific T Lymphocytes," Science, Oct. 4, 1996, 274(5284):94-96.
Bakker et al., "Conditional MHC class I ligands and peptide exchange technology for the human MHC gene products HLA-A1, -A3, -A11, and -B7," Proc Natl Acad Sci USA, Mar. 11, 2008, 105(10):3825-3830.
Chu et al., "SV40 DNA transfection of cells in suspension: analysis of the efficiency of transcription and translation of T-antigen," Gene, Mar. 1981, 13(2):197-202, 1 page (Abstract Only).
Deininger et al., "Allograft inflammatory factor-1 defines a distinct subset of infiltrating macrophages/microglial cells in rat and human gliomas," Acta Neuropathol, Dec. 2000, 100(6):673-680.
Fan et al., "Illumina Universal Bead Arrays," Methods in Enzymology, 2006, 410:57-73.
Glorioso et al., "Development and Application of Herpes Simplex Virus Vectors for Human Gene Therapy, " Annu. Rev. Microbiol., 1995; 49:675-710, 1 page (Abstract Only).
Graham et al., "A new technique for the assay of infectivity of human adenovirus 5 DNA," Virology, Apr. 1973, 52(2):456-467, 3 pages (Abstract Only).
Hadrup et al., "Parallel detection of antigen-specific T-cell responses by multidimensional encoding of MHC multimers," Nat. Methods., Jul. 2009, 6(7), 520-526.
Landegren et al., "A Ligase-Mediated Gene Detection Technique," Science, 1988, 241(4869):1077-1080.
Mabruk et al., "In situ hybridization: detecting viral nucleic acid in formalin-fixed, paraffin-embedded tissue samples," Expert Rev. Mol. Diagn., 2004, 4(5):653-661.
Makaryus et al., "Coronary venous angioplasty and stenting for biventricular pacemaker left ventricular lead implantation," Journal of Invasive Cardiology, 2008, 19(5), 3 pages.
Manz et al., "Phylogenetic Composition, Spatial Structure, and Dynamics of Lotic Bacterial Biofilms Investigated by Fluorescent in situ Hybridization and Confocal Laser Scanning Microscopy," Microb Ecol, May 1999, 37(4):225-237.
Soen et al., "Detection and Characterization of Cellular Immune Responses Using Peptide-MHC Microarrays," PLOS Biology, Dec. 22, 2003, 1(3):429-438.
Stanton et al., "Altered patterns of gene expression in response to myocardial infarction," Circulation research, May 12, 2000, 86(9), 939-945.
Zhou et al., "Analysis of the expression profile of Dickkopf-1 gene in human glioma and the associate with tumor malignancy," Journal of Experimental & Clinical Cancer Research, Oct. 28, 2010, 29(138):1-7.
Cellosaurus, "Cellosaurus Hs 742.Sk (CVCL_0887)," cellosaurus.org, Apr. 4, 2012, retrieved on May 23, 2025, retrieved from URL <https://www.cellosaurus.org/CVCL_0887>, 1 page.
Cellosaurus, "Cellosaurus MDA-MB-231 (CVCL_0062)," cellosaurus.org, Apr. 4, 2012, retrieved on May 23, 2025, retrieved from URL <https://www.cellosaurus.org/CVCL_0062>, 13 pages.
Janda et al., "16S rRNA Gene Sequencing for Bacterial Identification in the Diagnostic Laboratory: Pluses, Perils, and Pitfalls," Journal of Clinical Microbiology, 2007, 45(9):2761-2764.
Litosh et al., "Improved nucleotide sensitivity and termination of 3'-OH unblocked reversible terminators by molecular tuning of 2-nitrobenzyl alkylated HOMedU triphosphates," Nucleic Acids Research, Jan. 11, 2011, 339(6):E39, 13 pages.
Manning et al., "Benefits and pitfalls of secondary antibodies: why choosing the right secondary is of primary importance," PLoS One, 2012, 7(6):e38313.
Mohanty et al., "Bacterial/archaeal/organellar poly adenylation," Wiley Interdiscip Rev RNA, Mar.-Apr. 2011, 2(2):256-76, 36 pages (Author Manuscript).
Pray, "Eukaryotic Genome Complexity," Nature Education, 2008, 1(1):96, pp. 1-4.
Simon et al., "Immunohistochemical analysis of tissue microarrays," Methods Mol Biol., 2010, 664:113-26.
Viralzone.com, "Coronaviridae," viralzone.com, available on or before May 21, 2017, retreived on Mar. 20, 2025, retrieved from URL <https://web.archive.org/web/20200525133654/https://viralzone.expasy.org/30>, 2 pages.
Webb et al., "Chapter 2: Epi-Fluorescence Microscopy," Cell Imaging Techniques, Methods in Molecular Biology, 2012, 931:29-59.
U.S. Appl. No. 16/353,937, filed Mar. 14, 2019, Frisen et al..
U.S. Appl. No. 17/707,189, filed Mar. 29, 2022, Chell et al..
U.S. Appl. No. 60/416,118, filed Oct. 3, 2002, Fan et al..
U.S. Appl. No. 62/839,575, filed Apr. 26, 2019, Bent et al..
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
Adessi et al., "Solid phase DNA amplification: characterisation of primer attachment and amplification mechanisms," Nucl. Acids Res., Oct. 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003.

(56) References Cited

OTHER PUBLICATIONS

Affymetrix, "Human Genome U95Av2," Internet Citation, retrieved from the internet: on the World Wide Web affymetrix.com, retrieved on Oct. 2, 2002.
Agbavwe et al., "Efficiency, error and yield in light-directed maskless synthesis of DNA microarrays," Journal of Nanobiotechnology, Dec. 2011, 9:57, 17 pages.
Ahern et al., "Biochemical, Reagents Kits Offer Scientists Good Return On Investment," The Scientist, 1995, 9(15):20, 7 pages.
Ahern, "Biochemical, Reagents Kits Offer Scientists Good Return On Investment," The Scientist, Jul. 1995, 9(15):20, 7 pages.
Ahlfen et al., "Determinants of RNA quality from FFPE samples," PLoS One, Dec. 2007, 2(12):e1261, 7 pages.
Akatsuka et al., "Rapid screening of T-cell receptor (TCR) variable gene usage by multiplex PCR: Application for assessment of clonal composition," Tissue Antigens, Jan. 5, 1999, 53:122-134.
Akatsuka et al., "T cell receptor clonal diversity following allogeneic marrow grafting," Human Immunology, Jun.-Jul. 1996, 48:125-134.
Akeroyd, "Click chemistry for the preparation of advanced macromolecular architectures," Stellenbosch University, PhD Dissertation, Mar. 2010, 138 pages.
Albretsen et al., "Applications of magnetic beads with covalently attached oligonucleotides in hybridization: Isolation and detection of specific measles virus mRNA from a crude cell lysate", Anal. Biochem. 189: 40-50, 1990.
Albretsen et al., "Optimal conditions for hybridization with oligonucleotides: a study with myc-oncogene DNA probes," Anal Biochem., Apr. 1988, 170(1):193-202.
Allawi and SantaLucia, "Thermodynamics and NMR of Internal GâT Mismatches in DNA," Biochemistry, 1996, 36:10581-10594.
Altaras et al., "Production and formulation of adenovirus vectors," Adv Biochem Eng Biotechnol., Nov. 2005, 99:193-260.
Altschul et al., "Basic local alignment search tool," J. Mol. Biol., Oct. 5, 1990, 215(3):403-410.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Andresen et al., "Deciphering the Antibodyome—Peptide Arrays for Serum Antibody Biomarker Diagnostics," Current Proteomics, 6(1), 1-12, 2009.
Andresen et al., "Helicase-dependent amplification: use in OnChip amplification and potential for point-of-care diagnostics," Expert Rev Mol Diagn., Oct. 2009, 9(7):645-650.
Angenendt et al., "Cell-free Protein expression and functional assay in a nanowell chip format," Analytical Chemistry, 2004, 76(7):1844-49.
Angenendt et al., "Generation of High Density Protein Microarrays by Cell-free in Situ Expression of Unpurified PCR Products," Molecular and Cellular Proteomics, (2006) Ch. 5.9, pp. 1658-1666.
Appella, "Non-natural nucleic acids for synthetic biology," Current Opinion in Chemical Biology, Dec. 2009, 13(5-6): 687-696.
Armani et al., "2D-PCR: a method of mapping DNA in tissue sections," Lab on a Chip, 2009, 9(24):3526-34.
Atkinson, Overview of Translation: Lecture Manuscript, U of Texas (2000) DD. 6.1-6.8.
Azioune et al., "Simple and rapid process for single cell micropatterning," Lab Chip, Jun. 2009, 9(11):1640-1642.
Bains et al., "A Novel Method for Nucleic Acid Sequence Determination", Journal of Theoretical Biology, 1988, 135(3), 303-7.
Baird et al., "Rapid SNP Discovery and Genetic Mapping Using Sequenced RAD markers," PLOS One, 2008, 3(10):e3376.
Baner et al., "Signal amplification of padlock probes by rolling circle replication," Nucleic Acids Res., 1998, 26(22):5073-5078.
Barbie et al., "Systematic RNA interference reveals that oncogenic KRAS-driven cancers require TBK1," Nature, Nov. 2009, 462(7269):108-12.
Barnes, "PCR amplification of up to 35-kb DNA with high fidelity and high yield from lambda bacteriophage templates.," Proc. Natl. Acad. Sci USA, 91: 2216-2220, 1994.
Baugh et al., "Quantitative analysis of mRNA amplification by in vitro transcription," Nucleic Acids Res., 2001, 29:5:e29.
Beattie et al., "Advances in genosensor research," Clin Chem., May 1995, 41(5):700-6.
Beier et al., "Versatile derivatisation of solid support media for covalent bonding on DNA-microchips, " Nucleic Acids Res., May 1999, 27(9): 1970-7.
Bell, "A Simple Way to Treat PCR Products Prior to Sequencing Using ExoSAP-IT," Biotechniques, 2008, vol. 44, No. 6.
Bentley et al., "Accurate whole human genome sequencing using reversible terminator chemistry", Nature, 2008, 456:53-59.
Berger et al., "Universal bases for hybridization, replication and chain termination," Nucleic Acid Res., Aug. 2000, 28(15):2911-2914.
Bessmertnykh et al., "Efficient Palladium-Catalyzed Synthesis of Aminopyridyl Phosphonates from Bromopyridines and Diethyl Phosphite," Synthesis, 2008, 10:1575-1579.
Bielas et al., "Human cancers express a mutator phenotype," Proc. Natl. Acad. Sci. USA, 2006, 103(48): 18238-18242.
Bielas et al., "Quantification of random genomic mutations," Nat. Methods, 2005, 2(4):285-290.
Biol.wwu.edu [online], "Principles of Di-Base Sequencing and the Advantages of Color Space Analysis in the SOLID System," 2008, retrieved on Mar. 11, 2022, retrieved from URL<https://biol.wwu.edu//young/470/stuff/abi-solid.pdf>, 4 pages.
Birney, et al., "Identification and analysis of functional elements in 1% of the human genome by the Encode pilot project," Nature, 2007, 447:799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blandini et al., "Animal models of Parkinson's disease," Febs J., Apr. 2012, 279(7):1156-66.
Blokzijl et al., "Profiling protein expression and interactions: proximity ligation as a tool for personalized medicine," J Intern. Med., 2010, 268:232-245.
Blow, "Tissue Issues," Nature, 448(23), 959-962, 2007.
Boeke et al., "Transcription and reverse transcription of retrotransposons," Annu Rev Microbiol, 1989, 43:403-34.
Bonfield et al., "The application of numerical estimates of base calling accuracy to DNA sequencing projects," Nucleic Acids Research, 1995, 23(8): 1406-1410.
Bos et al., "In Vitro Evaluation of DNA-DNA Hybridization as a Two-Step Approach in Radioimmunotherapy of Cancer," Cancer Res., Jul. 1, 1994, 54(13):3479-3486.
Boulé et al., "Terminal deoxynucleotidyl transferase indiscriminately incorporates ribonucleotides and deoxyribonucleotides," J Biol Chem., Aug. 2001, 276(33):31388-93.
Bowtell, "The genesis and evolution of high-grade serous ovarian cancer," Nat. Rev. Cancer, 2010, (11):803-808 Abstract.
Boutros et al., "The art and design of genetic screens: RNA interference," Nat Rev Genet., Jul. 2008, 9(7):554-66.
Brandon et al., "Mitochondrial mutations in cancer," Oncogene, 2006, 25(34):4647-4662.
Brenner et al., "In vitro cloning of complex mixtures of DNA on microbeads: physical separation of differentially expressed cDNAs," Proc. Natl. Acad. Sci. USA, 2000, 97, 1665-1670.
Brenner et al., "Gene expression analysis by massively parallel signature sequencing (MPSS) on microbead arrays", Nat. Biotech. 18: 630-634, 2000.
Brockman et al., "Quality scores and SNP detection in sequencing-by-synthesis systems," Methods, 2008, 18:763-770.
Brow, "35—The Cleavase I enzyme for mutation and polymorphism scanning," PCR Applications Protocols for Functional Genomics, 1999, pp. 537-550.

(56) References Cited

OTHER PUBLICATIONS

Brown et al., "Retroviral integration: structure of the initial covalent product and its precursor, and a role for the viral IN protein, " Proc Natl Acad Sci USA, Apr. 1989, 86(8):2525-9.
Bullard et al., "Direct comparison of nick-joining activity of the nucleic acid ligases from bacteriophage T4," Biochem. J. 2006, 398:135-144.
Burns et al., "Well-less, gel-permeation formats for ultra-HTS," DDT, 2001, 6(12):S40-S47.
Burton et al., "Coverslip Mounted-Immersion Cycled in Situ RT-PCR for the Localization of mRNA in Tissue Sections," Biotechniques, 1998, 24; pp. 92-100.
Calvert, "Materials science. Printing cells," Science, Oct. 2007, 318(5848):208-209.
Cardona et al., "TrakEM2 0.9a User Manual," Sep. 8, 2011, retrieved on Jul. 29, 2022, retrieved from URL <https://www.ini.uzh.ch/~acardona/trakem2_manual.html>, 38 pages.
Carlson et al., "Function and Structure of a Prokaryotic Formylglycine-generating Enzyme," J. of Biological Chemistry, 2008, 283(29):20117-125.
Carter et al., "Stabilization of an optical microscope to 0.1 nm in three dimensions," Applied Optics, 2007, 46:421-427.
Cerritelli et al., "Ribonuclease H: the enzymes in eukaryotes," FEBS Journal, Mar. 2009, 276(6):1494-505.
Cerutti et al., "Generation of sequence-specific, high affinity anti-DNA antibodies," Journal of Biological Chemistry, 2001, 276(16):12769-12773.
Cha et al., "Specificity, Efficiency and Fidelity of PCR," Genome Res., 1993, 3:518-29.
Chandra et al., "Cell-free synthesis-based protein microarrays and their applications," Proteomics, 2009, 5(6):717-30.
Chatterjee et al., "Protein Microarray On-Demand: A Novel Protein Microarray System," PLos One, 2008, 3(9):e3265.
Chatterjee, et al., "Mitochondrial DNA mutations in human cancer. Oncogene," 2006, 25(34): 4663-4674.
Chen et al., "A Homogeneous, Ligase-mediated DNA diagnostic test," Genome research, 1998, 8(5):549-556.
Chen et al., "DNA hybridization detection in a microfluidic Channel using two fluorescently labelled nucleic acid probes," Biosensors and Bioelectronics, 2008, 23:1878-1882.
Chen et al., "Geometric control of cell life and death," Science, May 1997, 276(5317):1425-1428.
Chen et al., "Gray-scale photolithography using microfluidic photomasks," PNAS, Feb. 2003, 100(4):1499-1504.
Chen et al., "Parallel single nucleotide polymorphism genotyping by surface invasive cleavage with universal detection," Anal Chem., Apr. 2005, 77(8):2400-5.
Cheng et al., "Sensitive Detection of Small Molecules by Competitive Immunomagnetic-Proximity Ligation Assay," Anal Chem, 2012, 84:2129-2132.
Cheng, "The Contrast Formation in Optical Microscopy," Handbook Of Biological Confocal Microscopy, 2006, Chapter 8, pp. 162-206.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Chial, "DNA Sequencing Technologies Key to the Human Genome Project," Nature Education, 2008, 1(1):219, 7 pages.
Chiang et al., "NFkappaB translocation in human microvessel endothelial cells using a four- compartment subcellular protein redistribution assay," J Biochem Biophys Methods, Nov. 2000, 46(1-2):53-68.
Chrisey et al., "Covalent attachment of synthetic DNA to self-assembled monolayer films," Nucleic Acids Res., Aug. 1996, 24(15):3031-9.
Chung et al., "Imaging single-cell signaling dynamics with a deterministic high-density single-cell trap array," Anal Chem, Sep. 2011, 83(18):7044-7052.
Ciaccio et al., "Systems analysis of EGF receptor signaling dynamics with microwestern arrays," Nat Methods, Feb. 2010, 7(2):148-55.
Cockroft et al., "A single-molecule nanopore device detects DNA polymerase activity with single- nucleotide resolution," J Am Chem Soc., Jan. 2008, 130(3):818-20.
Colegio et al., "In vitro transposition system for efficient generation of random mutants of Campylobacter jejuni," J Bacteriol., Apr. 2001, 183(7):2384-8.
Condina et al., "A sensitive magnetic bead method for the detection and identification of tyrosine phosphorylation in proteins by MALDI-TOF/TOF MS," Proteomics, 2009, 9:3047-3057.
Constantine et al., "Use of genechip high-density oligonucleotide arrays for gene expression monitoring," Life Sceience News, Amersham Life Science; 11-14, 1998.
Cook et al., "The effects of secondary structure and O2 on the formation of direct strand breaks upon UV irradiation of 5-bromodeoxyuridine-containing oligonucleotides," Chem Biol., Jul. 1999, 6(7):451-9.
Copeland et al., "Mitochondrial DNA Alterations in Cancer," Cancer Invest., 2002, 557-569.
Cornett et al., "MALDI imaging mass spectrometry: molecular snapshots of biochemical systems," Nature Methods, 2007, 4(10):828-833.
Cox et al., "Tissue subcellular fractionation and protein extraction for use in mass-spectrometry-based proteomics," Nat Protoc., 2006, 1(4):1872-8.
Craig, "Transposon Tn7," Curr Top Microbiol Immunol., 1996, 204:27-48.
Craig, "V(D)J recombination and transposition: closer than expected," Science, Mar. 1996, 271(5255):1512, 1 page.
Cujec et al. "Selection of v-abl tyrosine kinase substate sequences from randomized peptide and cellular proteomic libraries using mRNA display," Chemistry and Biology, 2002, 9:253-264.
Curtis et al., "Adhesion of cells to polystyrene surfaces," J Cell Biol., Nov. 1983, 97(5):1500-1506.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101:4548-4553.
Dalma-Weiszhausz et al., "The affymetrix GeneChip platform: an overview," Methods Enzymol., 2006, 410:3-28.
Darmanis, et al., "ProteinSeq: High-Performance Proteomic Analyses by Proximity, Ligation and Next Generation Sequencing," PLos One, 2011, 6(9):e25583.
Daubendiek et al., "Rolling-Circle RNA Synthesis: Circular Oligonucleotides as Efficient Substrates for T7 RNA Polymerase," J. Am. Chem. Soc., 1995, 117:77818-7819.
Dawson et al., "Genetic animal models of Parkinson's disease," Neuron, Jun. 2010, 66(5):646-661.
De Clercq, "A 40-year journey in search of selective antiviral chemotherapy," Annu Rev Pharmacol Toxicol., 2011, 51:1-24.
Deamer et al., "Characterization of nucleic acids by nanopore analysis," Acc Chem Res., Oct. 2002, 35(10):817-25.
Deamer et al., "Nanopores and nucleic acids: prospects for ultrarapid sequencing," Trends Biotechnol., Apr. 2000, 18(4):147-51.
Dean et al., "Comprehensive human genome amplification using multiple displacement amplification," Proc Natl. Acad. Sci. USA 99:5261-66, 2002.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deibel et al., "Biochemical properties of purified human terminal deoxynucleotidyltransferase," J Biol Chem., May 1980, 255(9):4206-12.
Deo et al., "Detection of mammalian microRNA expression by in situ hybridization with RNA oligonucleotides," Dev Dyn., Sep. 2006, 235(9):2538-48.
Devine et al., "Efficient integration of artificial transposons into plasmid targets in vitro: a useful tool for DNA mapping, sequencing and genetic analysis," Nucleic Acids Res., Sep. 1994, 22(18):3765-72.

(56) References Cited

OTHER PUBLICATIONS

Dhindsa et al., "Virtual Electrowetting Channels: Electronic Liquid Transport with Continuous Channel Functionality," Lab Chip, 2010, 10:832-836.
Diez-Roux et al., "A high-resolution anatomical atlas of the transcriptome in the mouse embryo," PLoS Biol., Jan. 2011, 9(1):e1000582, 14 pages.
Doddridge et al., "UV-induced strand break damage in single stranded bromodeoxyuridine-containing DNA oligonucleotides," Chem Commun., 1998, pp. 1997-1998.
Dressman et al., "Transforming single DNA molecules into fluorescent magnetic particles for detection and enumeration of genetic variations," Proc. Natl. Acad. Sci. USA, 2003, 100:8817-8822.
Drmanac et al., "Accurate sequencing by hybridization for DNA diagnostics and individual genomics," Nature Biotechnology, 16:54-58, 1998.
Druley et al., "Quantification of rare allelic variants from pooled genomic DNA," Nat. Methods 6: 263-65, 2009.
Duhr et al., "Why molecules move along a temperature gradient," Proc Natl Acad Sci USA, Dec. 2006, 103(52):19678-19682.
Duncan et al., "Affinity chromatography of a sequence-specific DNA binding protein using teflon-linked oligonucleotides", Anal. Biochem. 169: 104-108, 1988.
Eberwine et al., "Analysis of gene expression in single live neurons," Proc. Natl. Acad. Sci., USA 89, 3010-3014, 1992.
Eberwine, "Amplification of mRNA Populations Using aRNA Generated from Immobilized Oligo(dT)-T7 Primed cDNA," BioTechniques 20 (4), 584, 1996.
Ebihara et al., "Molecular detection of dermatophytes and nondermatophytes in onychomycosis by nested polymerase chain reaction based on 28S ribosomal RNA gene sequences," Br J Dermatol., Nov. 2009, 161(5):1038-44.
Eguiluz et al., "Multitissue array review: A chronological description of tissue array techniques, applications and procedures," Pathology Research and Practice, 2006, 202:561-568.
Ekins et al., "Microarrays: their origins and applications, " Trends in Biotechnology, Jun. 1999, 17(6):217-218.
Eldridge et al. "An in vitro selection strategy for conferring protease resistance to ligand binding peptides," Protein Eng Des Sel., 22(11): 691-698, 2009.
Ellington et al., "Antibody-based protein multiplex platforms: technical and operational challenges," Clin Chem 56(2): 186-193, 2010.
Emmert-Buck et al., "Laser capture microdissection," Science, Nov. 1996, 274(5289):998-1001.
Ergin et al., "Proteomic Analysis of PAXgene-Fixed Tissues," J Proteome Res., 2010, 9(10):5188-96.
Escholarship.org [online], "Methods and devices for fabricating and assembling DNA and protein arrays for high-throughput analyses [electronic resource]," 2010, retrieved on Jun. 8, 2022, retrieved from URL<https://escholarship.org/uc/item/6tf7p46s>, 155 pages.
Espina et al., "Laser-capture microdissection," Nat Protoc, 2006, 1(2):586-603.
Evers et al., "The effect of formaldehyde fixation on RNA: optimization of formaldehyde adduct removal," J Mol Diagn., May 2011, 13(3):282-8.
Extended European Search Report in European Appln. No. 11766613.1, dated Jan. 15, 2014, 4 pages.
Fahy et al., "Design and synthesis of polyacrylamide-based oligonucleotide supports for use in nucleic acid diagnostics," Nucleic Acids Res., Apr. 1993, 21(8):1819-26.
Falconnet et al., "Surface engineering approaches to micropattern surfaces for cell-based assays," Biomaterials, Jun. 2006, 27(16):3044-3063.
Fan et al., "Highly parallel SNP genotyping," Cold Spring Symp. Quant. Biol., 68: 69-78, 2003.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Faruqi et al., "High-throughput genotyping of single nucleotide polymorphisms with rolling circle amplification," BMC Genomics, Aug. 2001, 2:4, 10 pages.
Ferreira et al., "Photocrosslinkable Polymers for Biomedical Applications," Biomedical Engineering-Frontiers and Challenges, Prof. Reza, 2011, 22 pages.
Fire and Xu, "Rolling replication of short DNA circles," Proc. Natl. Acad. Sci., 92: 4641-4645, 1995.
Fischer et al., "Hematoxylin and eosin staining of tissue and cell sections," CSH Protoc., May 2008, 3(5):1-3.
Fodor et al., "Light-Directed, Spatially Addressable Parallel Chemical Synthesis," Science, 251(4995), 767-773, 1995.
Folch et al., "Microfabricated elastomeric stencils for micropatterning cell cultures," J Biomed Mater Res, Nov. 2000, 52(2):346-353.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant to pancreatic and ovarian cancer," Clin. Chem., 5(3): 582-89, 2008.
Fredriksson et al., "Protein detection using proximity-dependent DNA ligation assays," Nature Biotech., 20: 473-77, 2002.
Frese et al., "Formylglycine Aldehyde Tag-Protein Engineering through a Novel Posttranslational Modification," ChemBioChem., 10: 425-27, 2009.
Fu et al., "Counting individual DNA molecules by the stochastic attachment of diverse labels," PNAS, 108: 9026-9031, 2011.
Fu et al., "Repeat subtraction-mediated sequence capture from a complex genome," Plant J., Jun. 2010, 62(5): 898-909.
Fullwood et al., "Next-generation DNA sequencing of paired-end tags (PET) for transcriptome and genome analyses," Genome Res., 19: 521-532, 2009.
Galon et al., "The immune score as a new possible approach for the classification of cancer," J Transl Med., Jan. 2012, 10:1, 4 pages.
Gamper et al., "Gene expression profile of bladder tissue of patients with ulcerative interstitial cystitis," BMC Genomics, Apr. 28, 2009, 10(199):1-17.
Gans et al., "Inkjet Printing of Polymers: State of the Art and Future Developments," Advanced Materials, Feb. 2004, 16(3):203-213.
Gao et al., "High density peptide microarrays. In situ synthesis and applications," Molecular Diversity, 8, 177-187, 2004.
Geiss et al., "Direct multiplexed measurement of gene expression with color-coded probe pairs," nature biotechnology, 2008, 26(3):317-325.
Genbank Accession No. AC009495.1, "*Homo sapiens* clone NH0490102, * Sequencing in Progress * , 12 unordered pieces," Aug. 24, 1999, 53 pages.
Genbank Accession No. AC009495.5, "*Homo sapiens* BAC clone RP11-49012 from 2, complete sequence," Apr. 21, 2005, 32 pages.
Genbank Accession No. AC037198.2, "*Homo sapiens* chromosome 15 clone CTD-2033D15 map 15q14, * Sequencing in Progress * , 62 unordered pieces," Apr. 25, 2000, 39 pages.
Genbank Accession No. AC087379.2, "*Homo sapiens* chromosome 11 clone RP11-396020 map 11, * Sequencing in Progress * , 5 ordered pieces," Jul. 6, 2002, 47 pages.
Genbank Accession No. AC087741.1, "*Homo sapiens* chromosome 17 clone RP11-334C17 map 17, Low-Pass Sequence Sampling," Jan. 22, 2001, 18 pages.
Genbank Accession No. AC100826.1, "*Homo sapiens* chromosome 15 clone RP11-279F6 map 15, Low-Pass Sequence Sampling," Nov. 22, 2001, 21 pages.
Genbank Accession No. AL445524.1, "*Homo sapiens* chromosome 1 clone RP11-295G20, Working Draft Sequence, 19 unordered pieces," Oct. 14, 2000, 47 pages.
Genome.ucsc.edu, [online], "Genome Browser Gateway," 2000, retrieved on Jun. 11, 2021, retrieved from URL<https://genome.ucsc.edu/cgi-bin/hgGateway>, 3 pages.
Gerard et al., "Excess dNTPs minimize RNA hydrolysis during reverse transcription," Biotechniques, Nov. 2002, 33(5):984, 986, 988, 990.
Giam et al., "Scanning probe-enabled nanocombinatorics define the relationship between fibronectin feature size and stem cell fate," PNAS, Mar. 2012, 109(12):4377-4382.

(56) References Cited

OTHER PUBLICATIONS

Gibson et al., "Enzymatic assembly of DNA molecules up to several hundred kilobases," Nat Methods., May 2009, 6(5):343-5.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Gilles et al., "Single nucleotide polymorphic discrimination by an electronic dot blot assay on semiconductor microchips," Nat Biotechnol, Apr. 1999, 17(4):365-70.
Glass et al., "Simple: a sequential immunoperoxidase labeling and erasing method," J. Histochem. Cytochem., Oct. 2009, 57(10):899-905.
Gloor, "Gene targeting in *Drosophila*, " Methods Mol Biol., 2004, 260:97-114.
Gnanapragasam, "Unlocking the molecular archive: the emerging use of formalin-fixed paraffin-embedded tissue for biomarker research in urological cancer," BJU International, 105, 274-278, 2009.
Goebl et al., "Development of a sensitive and specific in situ hybridization technique for the cellular localization of antisense oligodeoxynucleotide drugs in tissue sections," Toxicologic Pathology, Jun. 2007, 35(4):541-548.
Goldkom and Prockop, "A simple and efficient enzymatic method for covalent attachment of DNA to cellulose. Application for hybridization-restriction analysis and for in vitro synthesis of DNA probes.", Nucleic Acids Res. 14:9171-9191, 1986.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gotz et al., "Animal models of Alzheimer's disease and frontotemporal dementia," Nat Rev Neurosci., Jul. 2008, 9(7):532-44.
Grant et al., "Pathways and mechanisms of endocytic recycling," Nat. Rev. Mol. Cell Biol., Sep. 2009, 10(9):597-608.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gudjonsson et al., "Myoepithelial cells: their origin and function in breast morphogenesis and neoplasia," J Mammary Gland Biol Neoplasia, Jul. 2005, 10(3):261-72.
Gunderson et al., "Decoding Randomly Ordered DNA Arrays," Genome Research 14: 870-877, 2004.
Guo et al., "Direct fluorescence analysis of genetic polymorphisms by hybridization with oligonucleotide arrays on glass supports," Nucleic Acids Res., Dec. 1994, 22(24):5456-65.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hajduk et al., "Drug discovery: A question of library design," Nature, Feb. 2011, 470(7332):42-43.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS ONE, 2012, 7(7):e40405.
Han et al., "3C and 3C-based techniques: the powerful tools for spatial genome organization deciphering", Molecular Cytogenetics (2018) 11:21, 10 pages, 2018.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Harris et al., "Chloroplast ribosomes and protein synthesis," Microbiol. Mol. Biol. Rev., Dec. 1, 1994, 58(4): 700-754.
Harris et al., "The design and application of target-focused compound libraries," Comb Chem High Throughput Screen, Jul. 2011, 14(6):521-531.
Hattersley et al., "Development of a microfluidic device for the maintenance and interrogation of viable tissue biopsies," Lab Chip., Nov. 2008, 8(11):1842-6.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 19:4-9, 2008.
He et al., "Printing protein arrays from DNA arrays," Nature Methods, 5:175-77, 2008.
He, "Cell-free protein synthesis: applications in proteomics and biotechnology," New Biotechnology 25: 126-132, 2008.
Healy, "Nanopore-based single-molecule DNA analysis," Nanomedicine (Lond), Aug. 2007, 2(4):459-81.
Hedskog et al., "Dynamics of HIV-1 Quasispecies during Antiviral Treatment Dissected using Ultra-Deep Pyrosequencing," PLoS One, 5(7):e11345, 2010.
Hein et al., "Click Chemistry, A Powerful Tool for Pharmaceutical Sciences", Pharm Res., 25(10): 2216-2230, 2008.
Hejatko et al., "In Situ Hybridization Techniques for mRNA Detection in Whole Mount Arabidopsis Samples," Nature Protocols, 2006, 1(4):1939-1946.
Hendrickson et al., "High sensitivity multianalyte immunoassay using covalent DNA-labeled antibodies and polymerase chain reaction," Nucleic Acid Research, Feb. 11, 1995, 23(3):522-529.
Henikoff et al., "Amino acid substitution matrices from protein blocks," Proc. Natl. Acad. Sci., Nov. 15, 1992, 89:10915-9.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally-derived short sequence reads," Nature Methods, 7(2): 119-25, 2010.
Higgins et al., "Clustal: A Package for Performing Multiple Sequence Alignment on a Microcomputer," Gene, 1988, 73:237-244.
Hlubek et al., "Heterogeneous expression of Wnt/beta-catenin target genes within colorectal cancer," Int J Cancer., Nov. 2007, 121(9):1941-8.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hober et al., "Human protein atlas and the use of microarray technologies," Curr Opin Biotechnol., Feb. 2008, 19(1):30-35.
Holmstrøm et al., "A highly sensitive and fast nonradioactive method for detection of polymerase chain reaction products," Anal Biochem, Mar. 1993, 209(2):278-83.
Hoyer et al., "Electrostatic spraying: a novel technique for preparation of polymer coatings on electrodes," Anal Chem, Nov. 1996, 68(21):3840-4.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.

(56) References Cited

OTHER PUBLICATIONS

Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Hytönen et al., "Design and construction of highly stable, protease-resistant chimeric avidins," J Biol Chem., Mar. 2005, 280(11):10228-33.
Ichikawa et al., "In vitro transposition of transposon Tn3," J Biol. Chem., Nov. 1990, 265(31):18829-32, Abstract.
Illumina.com [online], "Array-Based Gene Expression Analysis," 2011, retrieved on Dec. 13, 2021, retrieved from URL<https://www.illumina.com/documents/products/datasheets/datasheet_gene_exp_analysis.pdf>, 5 pages.
Im et al., "An Introduction to Performing Immunofluorescence Staining," Biobanking: Methods and Protocols, Method in Molecular Biology, Yong (ed.), 2019, 1897, Chapter 26, 299-311.
Imbeaud et al., "Towards standardization of RNA quality assessment using user-independent classifiers of microcapillary electrophoresis traces," Nucleic Acids Res., Mar. 2005, 33(6):e56, 12 pages.
Inoue and Wittbrodt, "One for All—A Highly Efficient and Versatile Method for Fluorescent Immunostaining in Fish Embryos," PLoS One 6, e19713, 2011.
Invitrogen, Immune Response Biomarker Profiling Service Report, Invitrogen, 2009, 1-33.
Jabara et al., Accurate sampling and deep sequencing of the HIV-1 protease gene using a Primer ID. PNAS 108(50); 20166-20171, 2011.
Jain, "Transport of molecules, particles, and cells in solid tumors," Annu. Rev. Biomed. Eng., 1999, 1:241-263.
Jamur and Oliver, "Permeabilization of cell membranes.," Method Mal. Biol., 588: 63-66, 2010.
Jawhar et al., "Tissue Microarray: A rapidly evolving diagnostic and research tool," Annals of Saudi Medicine, Mar. 2009, 29(2):123-7.
Jennane et al., "Photolithography of self-assembled monolayers: optimization of protecting groups by an electroanalytical method," Can. J Chem., Dec. 1996, 74(12):2509-2517.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jones et al., Comparative lesion sequencing provides insights into tumor evolution. Proc. Natl. Acad. Sci. USA 105(11): 4283-4288, 2008.
Joos et al., "Covalent attachment of hybridizable oligonucleotides to glass supports," Anal Biochem., Apr. 1997, 247(1):96-101.
Jucá et al., "Effect of dimethyl sulfoxide on reverse transcriptase activity," Braz. J. Med. Biol. Res., Mar. 1995, 28(3):285-90.
Kainkaryam et al., "Pooling in high-throughput drug screening" Curr Opin Drug Discov Devel., May 2009, 12(3):339-50.
Kanehisa, "Use of statistical criteria for screening potential homologies in nucleic acid sequences", Nucleic Acids Res. 12: 203-213, 1984.
Kap et al., "Histological Assessment of PAXgene Tissue Fixation and Stabilization Reagents," PLoS One 6, e27704, 10 pages, 2011.
Kapteyn et al., "Incorporation of Non-Natural Nucleotides Into Template-Switching Oligonucleotides Reduces Background and Improves cDNA Synthesis From Very Small RNA Samples, " BMC Genomics, 2010, 11(413): 1-9.
Karlin et al., "Applications and statistics for multiple high-scoring segments in molecular sequences," Proc. Natl. Acad. Sci., Jun. 15, 1993, 90:5873-7.
Kelleher et al., "Characterization of RNA Strand Displacement Synthesis by Moloney Murine Leukemia Virus Reverse Transcriptase," J Biol Chem, Apr. 1998, 273(16):9976-86.
Kibbe, "OligoCalc: an online oligonucleotide properties calculator," Nucleic Acids Res., Jul. 2007, 35:W43-6.
Kirby et al., "Cryptic plasmids of Mycobacterium avium: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Koch et al., "Photochemical immobilization of anthraquinone conjugated oligonucleotides and PCR amplicons on solid surfaces," Bioconjugate Chem., Jul. 2000, 11(4):474-483.
Kolb et al., "Click Chemistry: Diverse Chemical Function from a Few Good Reactions," Angew. Chem. Int. Ed., 40(11): 2004-2021, 2001.
Kolbert et al., "Ribosomal DNA sequencing as a tool for identification of bacterial pathogens," Curr Opin Microbiol, Jun. 1999, 2(3):299-305.
König et al., "iCLIP reveals the function of hnRNP particles in splicing at individual nucleotide resolution," Nat Struct Mol Biol., Jul. 2010, 17(7):909-915.
Korbel et al., "Paired-End Mapping Reveals Extensive Structural Variation in the Human Genome," Science, 318(5849): 420-426, 2007.
Korlach et al., "Selective aluminum passivation for targeted immobilization of single DNA polymerase molecules in zero-mode waveguide nanostructures," Proc. Natl. Acad. Sci. USA 105, 1176-1181, 2008.
Kozlov et al., "A High-Complexity Multiplexed Solution-Phase Assay for Profiling Protease Activity on Microarrays," Comb Chem High Throughput Screen, 11: 24-35, 2008.
Kozlov et al., "A Highly Scalable Peptide-Based Assay System for Proteomics," PLoS ONE, 7(6): e37441, 2012.
Kozlov et al., "A Method for Rapid Protease Substrate Evaluation and Optimization," Comb Chem High Throughput Screen, 9: 481-87, 2006.
Kristensen et al., "High-Throughput Methods for Detection of Genetic Variation," BioTechniques, Feb. 2001, 30(2):318-332.
Kuijpers et al. "Specific recognition of antibody-oligonucleotide conjugates by radiolabeled antisense nucleotides: a novel approach for two-step radioimmunotherapy of cancer," Bioconjugate Chem., Jan. 1, 1993, 4(1):94-102.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA-Protein Fusions: Covalent Protein-Gene Conjugates for the In Vitro Selection of Peptides and Proteins," ChemBioChem., 2: 666-72, 2001.
Kwok, "High-throughput genotyping assay approaches," Pharmocogenomics, Feb. 2000, 1(1):95-100.
Kwon et al., Polyelectrolyte Gels-Fundamentals and Applications, Nov. 10, 2006, Polymer Journal, 38, pp. 1211-1219.
Lage et al., "Whole Genome Analysis of Genetic Alterations in Small DNA Samples Using Hyperbranched Strand Displacement Amplification and Array—CGH," Genome Research 13: 294-307, 2003.
Lampe et al., "A purified mariner transposase is sufficient to mediate transposition in vitro," Embo J., Oct. 1996, 15(19):5470-9.
Lamture et al., "Direct detection of nucleic acid hybridization on the surface of a charge coupled device," Nucleic Acid Res., Jun. 1994, 22(11):2121-5.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl", Gene 36: 201-210, 1985.
Larman et al., "Autoantigen discovery with a synthetic human peptidome," Nature Biotechnology, doi:1 0.1038/nbt.1856, vol. 29, No. 6, pp. 535-541, 2011.
Larsen et al., "Characterization of a recombinantly expressed proteinase K-like enzyme from a psychrotrophic Serratia sp, " Febs J., Jan. 2006, 273(1):47-60.
Larsson et al., "In situ detection and genotyping of individual mRNA molecules," Nat Methods, May 2010, 7(5):395-7.
Larsson et al., "In situ genotyping individual DNA molecules by target-primed rolling-circle amplification of padlock probes," Nat Methods, Dec. 2004, 1(3):227-32.

(56) References Cited

OTHER PUBLICATIONS

Lassmann et al., A Novel Approach For Reliable Microarray Analysis of Microdissected Tumor Cells From Formalin-Fixed and Paraffin-Embedded Colorectal Cancer Resection Specimens, J Mol Med, 87, 211-224, 2009.
Laurell et al., "Chip integrated strategies for acoustic separation and manipulation of cells and particles," Chem. Soc. Rev., Mar. 2007, 36(3):492-506.
Lee et al., "A novel COL 3A1 gene mutation in patient with aortic dissected aneurysm and cervical artery dissections," Heart Vessels, Mar. 2008, 23(2):144-8.
Lee et al., "Cytokines in cancer immunotherapy," Cancers (Basel), Oct. 2011, 3(4):3856-3893.
Lee et al., "Improving the efficiency of genomic loci capture using oligonucleotide arrays for high throughput resequencing," BMC Genomics, Dec. 2009, 10:646, 12 pages.
Lee et al., "Protein nanoarrays generated by dip-pen nanolithography," Science, Mar. 2002, 295(5560):1702-1705.
Lenard, "Viral Membranes," Encyclopedia of Virology, Jul. 2008, pp. 308-314.
Leriche et al., "Cleavable linkers in chemical biology.", Bioorganic & Medicinal Chemistry, 20: 571-582, 2012.
Levene et al., "Zero-Mode Waveguides for Single-Molecule Analysis at High Concentrations," Science 299, 682-686, 2003.
Li et al., "A photocleavable fluorescent nucleotide for DNA sequencing and analysis," Proc. Natl. Acad. Sci., 100: 414-419, 2003.
Li et al., "DNA molecules and configurations in a solid-state nanopore microscope," Nat Mater., Sep. 2003, 2(9):611-5.
Li et al., "RASL-seq for Massively Parallel and Quantitative Analysis of Gene Expression," Curr Protoc Mol Biol., Apr. 2012, 4(13):1-10.
Linnarsson, "Recent advances in DNA sequencing methods—general principles of sample preparation," Experimental Cell Research, 316: 1339-1343, 2010.
Liu et al. "Barcoded oligonucleotides ligated on RNA amplified for multiplexed and parallel in situ analyses," Nucleic Acids Res., Mar. 8, 2021, 49(10):e58, 15 pages.
Liu et al., "Method for Quantitative Proteomics Research by Using Metal Element Chelated Tags Coupled with Mass Spectrometry," Analytical Chemistry, 2006, 78:6614-6621.
Liu et al., "Surface and interface control on photochemically initiated immobilization," J Am Chem Soc., Nov. 2006, 128(43):14067-72.
Liu et al., An integrated and sensitive detection platform for biosensing application based on Fe@Au magnetic nanoparticles as bead array carries Biosensors and Bioelectronics, 2010, 26(4):1442-1448.
Lizardi et al., "Mutation detection and single-molecule counting using isothermal rolling-circle amplification," Nat. Genet. 19: 225-232, 1998.
Lopez-Otín et al., "Protease degradomics: a new challenge for proteomics," Nat Rev Mol Cell Biol., Jul. 2002, 3(7):509-19.
Lu et al., "A microfluidic electroporation device for cell lysis," Lab Chip., Jan. 2005, 5(1):23-29.
Lund et al., "Assessment of methods for covalent binding of nucleic acids to magnetic beads, Dynabeads, and the characteristics of the bound nucleic acids in hybridization reactions.", Nucleic Acids Res., 16: 10861-80, 1988.
Lundberg et al., "High-fidelity amplification using a thermostable DNA polymerase isolated from Pyrococcus furiosus.," Gene., 108(1): 1-6, 1991.
Lundberg et al., "Homogeneous antibody-based proximity extension assays provide sensitive and specific detection of low-abundant proteins in human blood," Nucleic Acids Res., 39(15): e102, 2011.
Lundberg et al., "Multiplexed homogeneous proximity ligation assays for high-throughput protein biomarker research in serological material," Mol Cell Proteomics, 10(4): M110.004978, 2011.
Lundin et al., "Increased throughput by parallelization of library preparation for massive sequencing," PLoS One, Apr. 2010, 5(4):e10029, 7 pages.
Lundquist et al., "Parallel confocal detection of single molecules in real time," Opt. Lett. 33, 1026-1028, 2008.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck, et al., "Immunohistochemical Markers for Quantitative Studies of Neurons and Glia in Human Neocortex," J Histochem Cytochem 56, 201-21, 2008.
Lykidis et al., "Novel zinc-based fixative for high quality DNA, RNA and protein analysis," Nucleic Acids Res., Jun. 2007, 35(12):e85, 10 pages.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci. 58, 190-6, 2001.
Magaki et al., "An introduction to Performance of Immunohistochemistry," Biobanking: Methods and Protocols, Method in Molecular Biology, Yong (ed.), 2019, 1897, Chapter 25, 289-298.
Malkov et al., "Multiplexed measurements of gene signatures in different analytes using the Nanostring nCounter™ Assay System." BMC research notes., 2009, 2:80.
Marras, "Selection of fluorophore and quencher pairs for fluorescent nucleic acid hybridization probes," Methods Mol Biol., 2006, 335:3-16.
Martin, "Cutadapt removes adapter sequences from high-throughput sequencing reads," EMBnet Journal, 2011, 17(1):10-12.
Massey et al., "Fluorescence resonance energy transfer (FRET) for DNA biosensors: FRET pairs and Förster distances for various dye-DNA conjugates," Anal Chim Acta., May 2006, 568(1-2):181-9.
Masuda et al., "Analysis of chemical modification of RNA from formalin-fixed samples and optimization of molecular biology applications for such samples," Nucleic Acids Research, Nov. 1999, 27(22):4436-4443.
Materna et al., "High accuracy, high-resolution prevalence measurement for the majority of locally expressed regulatory genes in early sea urchin development," Gene Expr Patterns., 2010, 10(4-5):177-184.
Mattheyses et al., "Imaging with total internal reflection fluorescence microscopy for the cell biologist," J Cell Sci., Nov. 2010, 123(Pt 21):3621-3628.
McCloskey et al., "Encoding PCR Products with Batch-stamps and Barcodes," Biochem. Genet. 45: 761-767, 2007.
Mcgee, "Structure and Analysis of Affymetrix Arrays," UTSW Microarray Analysis Course, Oct. 28, 2005, 68 pages.
McKernan et al., "Sequence and structural variation in a human genome uncovered by short-read, massively parallel ligation sequencing using two-base encoding," Genome Res., 19: 1527-41, 2009.
Megason et al., "Imaging in Systems Biology," Cell 130, Sep. 7, 2007, pp. 784-795.
Metzker "Sequencing technologies—the next generation," Nature Reviews Genetics, 11: 31-46, 2010.
Meyer et al., "Fast evolving 18S rRNA sequences from Solenogastres (Mollusca) resist standard PCR amplification and give new insights into mollusk substitution rate heterogeneity," BMC Evol. Biol., Mar. 2010, 10:70, 12 pages.
Micke et al., "Biobanking of fresh frozen tissue: RNA is stable in nonfixed surgical specimens," Lab Invest., Feb. 2006, 86(2):202-11.
Miele et al., "Mapping cis- and trans- chromatin interaction networks using chromosome conformation capture (3C)," Methods Mol Biol., 2009, 464:105-21.
Miller et al., "Basic Concepts of Microarrays and Potential Applications in Clinical Microbiology," Clinical Microbiology Reviews, vol. 22, No. 4, pp. 611-633, 2009.
Miner et al., "Molecular barcodes detect redundancy and contamination in hairpin-bisulfite PCR," Nucleic Acids Res., Sep. 2004, 32(17):e135, 4 pages.
Mir et al., "Sequencing by cyclic ligation and cleavage (CycliC) directly on a microarray captured template," Nucleic Acids Research, 37(1):e5, 8 pages, 2009.

(56) References Cited

OTHER PUBLICATIONS

Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.
Mitra et al., "In situ localized amplification and contact replication of many individual DNA molecules," Nucleic Acids Res., Dec. 1999, 27(24):e34, 6 pages.
Mitsuhashi et al., "Gene manipulation on plastic plates," Nature 357: 519-520, 1992.
Mizusawa et al., "A bacteriophage lambda vector for cloning with BamHI and Sau3A," Gene, 20: 317-322, 1982.
Mlecinik et al., "Histopathologic-based prognostic factors of colorectal cancers are associated with the state of the local immune reaction," J Clin Oncol., Feb. 2011, 29(6):610-8.
Mortazavi et al., "Mapping and quantifying mammalian transcriptomes by RNA-Seq," Nature Methods, 5(7): 621-8, 2008.
Moshrefzadeh et al., "Nonuniform photobleaching of dyed polymers for optical waveguides," Applied Physics Letters, 1993, 62:16-18.
Motea et al., "Terminal deoxynucleotidyl transferase: the story of a misguided DNA polymerase," Biochim Biophys Acta., May 2010, 1804(5):1151-66.
Mueller et al., "RNA Integrity Number (RIN)—Standardization of RNA Quality Control," Agilent Technologies, 2004, 8 pages.
Nadji et al., "Immunohistochemistry of tissue prepared by a molecular-friendly fixation and processing system," Appl Immunohistochem Mol Morphol., Sep. 2005, 13(3):277-82.
Nagahara et al., "Neuroprotective effects of brain-derived neurotrophic factor in rodent and primate models of Alzheimer's disease," Nat Med., Mar. 2009, 15(3):331-337.
Nagai et al., "Site-specific DNA cleavage by antisense oligonucleotides covalently linked to phenazine di-N-oxide," J Biol. Chem., Dec. 1991, 266(35):23994-4002.
Nakamura et al., "Biocompatible inkjet printing technique for designed seeding of individual living cells," Tissue Eng, Nov. 2005, 11(11-12):1658-1666.
Nakao et al., "Myosin heavy chain gene expression in human heart failure," J Clin Invest., Nov. 1997, 100(9):2362-70.
Nallur et al., "Signal amplification by rolling circle amplification on DNA microarrays," Nucleic Acids Res., Dec. 1, 2001, 29(23):e118, 9 pages.
Nam et al., "Nanoparticle-Based Bio-Bar Codes for the Ultrasensitive Detection of Proteins," Science, Sep. 26, 2003, 301(5641):1884-1886.
Nandakumar et al., "How an RNA Ligase Discriminates RNA versus DNA Damage," Molecular Cell, 2004, 16(2):211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ng et al., "Gene identification signature (GIS) analysis for transcriptome characterization and genome annotation," Nature Methods, 2(2): 105-111, 2005.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nichols et al., "RNA Ligases," Curr Protoc Mol Biol., Oct. 2008, 84(1):3.15.1-3.15.4.
Nicholson, "Diffusion and related transport mechanisms in brain tissue," Rep. Prog. Phys., Jun. 2001, 64(7):815-884.
Niedringhaus et al., "Landscape of next-generation sequencing technologies," Anal Chem., Jun. 2011, 83(12):4327-41.
Niemeyer, "The developments of semisynthetic DNA-protein conjugates," Trends Biotechnol, Sep. 2002, 20(9): 395-401.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "Padlock Probes: Circularizing Oligonucleotides for Localized DNA Detection," Science, Sep. 30, 1994, 265(5181):2085-2088.
Nilsson et al., "RNA-templated DNA ligation for transcript analysis," Nucleic Acids Res., Jan. 2001, 29(2):578-81.
Nuovo, "In situ PCR: protocols and applications.," Genome Res, Feb. 1995, 4 (4):151-167.
Ohtsubo et al., "Bacterial insertion sequences," Curr Top Microbiol Immunol., 1996, 204:1-26.
Oleinikov et al., "Self-assembling protein arrays using electronic semiconductor microchips and in vitro translation," J Proteome Res, May-Jun. 2003, 2(3): 313-319.
Olivier, "The Invader assay for SNP genotyping," Mutat. Res., Jun. 2005, 573(1-2):103-110.
Oren et al., "Selective lysis of bacteria but not mammalian cells by diastereomers of melittin: structure- function study, " Biochemistry, Feb. 1997, 36(7):1826-35.
Osada et al., "Epitope mapping using ribosome display in a resconstituted cell-free protein synthesis system," J Biochem, May 2009, 145(5): 693-700.
O-Shannessy et al., "Detection and quantitation of hexa-histidine-tagged recombinant proteins on western blots and by a surface plasmon resonance biosensor technique," Anal Biochem, 229(1): 119-124, 1995.
Ostuni et al., "Patterning Mammalian Cells Using Elastomeric Membranes," Langmuir, Aug. 2000, 16(20):7811-7819.
Ozsolak et al., "Digital transcriptome profiling from attomole-level RNA samples," Genome Res., Apr. 2010, 20(4):519-25.
Palamanda et al., "Evaluation of CYP1A1 and CYP2B1/2 m-RNA Induction in Rat Liver Slices Using the NanoString® Technology: A Novel Tool for Drug Discovery Lead Optimization," Drug metabolism letters, Nov. 3, 2009, 3(3):171-175.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Cancer gene therapy using adeno-associated virus vectors," Front Biosci., Jan. 2008, 13:2653-59.
Park et al., "The Estimation of Breast Cancer Disease-Probability by Difference of Individual Susceptibility," Cancer Res. Treat., Feb. 2003, 35(1):35-51, Abstract.
Patil et al., "DNA-based therapeutics and DNA delivery systems: a comprehensive review," Aaps J, Apr. 2005, 7(1):E61-77.
Patton et al., "Rainbow's end: the quest for multiplexed fluorescence quantitative analysis in proteomics." Current Opinion in Chemical Biology, Feb. 1, 2002, 6(1):63-69.
PCT International Preliminary Report on Patentability in International Appln. No. PCT/US2011/031308, dated Oct. 9, 2012, 7 pages.
PCT International Search Report and Written Opinion in International Appln. No. PCT/US2011/031308, dated May 25, 2011, 8 pages.
Pearson et al., "Improved tools for biological sequence comparison," Proc. Natl. Acad. Sci., May 1988, 85:2444-2448.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penland et al., "RNA expression analysis of formalin-fixed paraffin-embedded tumors," Laboratory Investigation, Apr. 2007, 87(4):383-391.
Perler et al., "Intervening sequences in an Archaea DNA polymerase gene," PNAS USA, Jun. 1992, 89(12): 5577-5581.
Perocchi et al., "Antisense artifacts in transcriptome microarray experiments are resolved by actinomycin D," Nucleic Acids Res., 2007, 35(19):e128, 7 pages.

(56) References Cited

OTHER PUBLICATIONS

Petterson et al., "Generations of sequencing technologies," Genomics, 2009, 105-111.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Piston et al., "Fluorescent protein FRET: the good, the bad and the ugly," Trends Biochem Sci., Sep. 2007, 32(9):407-14.
Plasterk, "The Tc1/mariner transposon family," Curr Top Microbiol Immunol., 1996, 204:125-43.
Pluen et al., "Diffusion of macromolecules in agarose gels: comparison of linear and globular configurations," Biophys J., Jul. 1999, 77(1):542-552.
Polsky-Cynkin et al., "Use of DNA Immobilizedon Plastic and Agarose Supports to Detect DNA by Sandwich Hybridization," Clin. Chem. 31: 1438-1443, 1985.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009 (Year: 2009).
Punwaney et al., "Human papillomavirus may be common within nasopharyngeal carcinoma of Caucasian Americans: investigation of Epstein-Barr virus and human papillomavirus in eastern and western nasopharyngeal carcinoma using ligation-dependent polymerase chain reaction," Head & Neck, Jan. 1999, 21(1):21-29.
Raab et al., "Human tRNA genes function as chromatin insulators, " Embo J., Jan. 2012, 31(2):330-50.
Raj et al., "Imaging individual mRNA molecules using multiple singly labeled probes," Nature Methods, Oct. 2008, 5(10):877-879, 9 pages.
Ramachandran et al., "Next-generation high-density self-assembling functional protein arrays," Nature Methods, Jun. 2008, 5(6):535-538.
Ramanujan et al., "Diffusion and convection in collagen gels: implications for transport in the tumor interstitium," Biophys. J., Sep. 2002, 83(3):1650-1660.
Ranki et al., "Sandwich hybridization as a convenient method for the detection of nucleic acids in crude samples", Gene 21: 77-85, cellulose, 1983.
Razonable, "Antiviral drugs for viruses other than human immunodeficiency virus," Mayo Clinic Proceedings, Oct. 2011, 86(10):1009-26.
Reijenga et al., "Buffer Capacity, Ionic Strength and Heat Dissipation in Capillary Electrophoresis," Journal of Chromatography A, Sep. 13, 1996, 744(1-2):147-153.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rettig et al., "Large-scale single-cell trapping and imaging using microwell arrays," Anal Chem, Sep. 2005, 77(17):5628-5634.
Reznikoff, "Tn5 as a model for understanding DNA transposition," Mol Microbiol., Mar. 2003, 47(5):1199-206.
Ristova et al., "Study of hydrogenated amorphous silicon thin films as a potential sensor for He—Ne laser light detection," Applied Surface Science, Sep. 2003, 218(1-4):44-53.
Roberts et al., "RNA-peptide fusions for the in vitro selection of peptides and proteins," Pnas USA, Nov. 1997, 94: 12297-122302.
Robins et al., "Comprehensive assessment of T-cell receptor β-chain diversity in αβ T cells," Blood, Nov. 5, 2009, 114(19):4099-4107.
Robinson et al., "Small-sample estimation of negative binomial dispersion, with applications to SAGE data," Biostatistics, Apr. 2008, 9(2):321-332.
Rogers et al., "Immobilization of oligonucleotides onto a glass support via disulfide bonds: A method for preparation of DNA microarrays," Anal Biochem., Jan. 1999, 266(1):23-30.
Rogers et al., "Use of a novel cross-linking method to modify adenovirus tropism," Gene Ther., Dec. 1997, 4(12):1387-92.
Ronaghi et al., "A sequencing method based on real-time pyrophosphate," Science, Jul. 1998, 281(5375): 363-365.
Ronaghi et al., "Real-time DNA sequencing using detection of pyrophosphate release," Analytical Biochemistry, Nov. 1996, 242(1 ): 84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Rouillard et al., "OligoArray 2.0: design of oligonucleotide probes for DNA microarrays using a thermodynamic approach," Nuc. Acid Research, Jun. 2003, 31(12): 3057-3062.
Rountenberg et al., "Microfluidic probe: a new tool for integrating microfluidic environments and electronic wafer-probing," Lab Chip, Oct. 2009, 10(1):123-127.
Rubin et al., "Whole-genome resequencing reveals loci under selection during chicken domestication.," Nature, Mar. 2010, 464: 587-591.
Rubina et al., "Hydrogel-based protein microchips: manufacturing, properties, and applications," Biotechniques, May 2003, 34(5):1008-14.
Rush et al., "New Aldehyde Tag Sequences Identified by Screening Formylglycine Generating Enzymes in Vitro and in Vivo," J. of American Chemical Society, Aug. 2008, 130(37): 12240-12241.
Russell et al., "Molecular mechanisms of late endosome morphology, identity and sorting," Curr. Opin. Cell Bio., Aug. 2006, 18(4):422-428.
San Paulo et al., "High-resolution imaging of antibodies by tapping-mode atomic force microscopy: attractive and repulsive tip-sample interaction regimes," Biophys J., Mar. 2000, 78(3):1599-1605.
Sano et al., "Immuno-PCR: Very Sensitive Antigen Detection by Means of Specific Antibody-DNA Conjugates," Science, Oct. 2, 1992, 258(5079):120-122.
Schellings et al., "Absence of SPARC results in increased cardiac rupture and dysfunction after acute myocardial infarction, " J Exp Med., Jan. 2009, 206(1):113-23.
Schena et al., "Quantitative monitoring of gene expression patterns with a complementary DNA microarray," Science, Oct. 1995, 270(5235):467-470.
Schena et al., "Entering the Postgenome Era," Science, 1995, 270:368-9, 371.
Schlapak et al., "Glass surfaces grafted with high-density poly (ethylene glycol) as substrates for DNA oligonucleotide microarrays, " Langinuir, Jan. 2006, 22: 277-285.
Schmitt et al., "Detection of ultra-rare mutations by next-generation sequencing," PNAS (2012) 109:14508-14523.
Scholz et al., "The Molecular Chaperone Hsp90 Is Required for Signal Transduction by Wild-Type Hck and Maintenance of Its Constitutively Active Counterpart1," Cell Growth Differ., Aug. 2001, 12(8):409-417.
Schouten et al., "Relative quantification of 40 nucleic acid sequences by multiplex ligation-dependent probe amplification," Nucleic Acids Res., Jun. 2002, 30(12):e57, 13 pages.
Schroeder et al., "The RIN: an RNA integrity No. for assigning integrity values to RNA measurements," BMC Molecular Biology, Jan. 2006, 7:3, 14 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
ScienceDirect.com [online], "Plant Fibers," Definition, 2011, retrieved on Apr. 13, 2022, retrieved from URL<https://www.sciencedirect.com/topics/agricultural-and-biological-sciences/plant-fibers>, 9 pages.
Sekar et al., "Fluorescence resonance energy transfer (FRET) microscopy imaging of live cell protein localizations," J Cell Biol., Mar. 2003, 160(5):629-33.

(56) References Cited

OTHER PUBLICATIONS

Sergeeva et al., "Display technologies: Application for the discovery of drug and gene delivery aaents," Advanced Drug Delivery Reviews (2006) 58(15):1622-1654.
Seurynck-Servoss et al., "Evaluation of Surface Chemistries for Antibody Microarrays", Anal Biochem., 371(1): 105-115, 2007.
Shalon et al., "A DNA microarray system for analyzing complex DNA samples using two-color fluorescent probe hybridization, " Genome Res., Jul. 1996, 6(7):639-45.
Shelbourne et al., "Fast copper-free click DNA ligation by the ring-strain promoted alkyne-azide cycloaddition reaction.", Chem. Commun., 47: 6257-6259, 2011.
Shendure et al., "Accurate Multiplex Polony Sequencing of an Evolved Bacterial Genome," Science, 2005, 309:1728-1732.
Shi et al., "The MicroArray Quality Control (MAQC) project shows inter- and intraplatform reproducibility of gene expression measurements," Nature Biotechnology, 2006, 24(9):1151-61.
Shi, "Enabling large-scale pharmacogenetic studies by high-throughput mutation detection and genotyping technologies," Clin. Chem., Feb. 2001, 47(2):164-172.
Shibata et al., "Detection of human papilloma virus in paraffin-embedded tissue using the polymerase chain reaction," J Exp Med., Jan. 1988, 167(1):225-30.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Shoemaker et al., "Quantitative phenotypic analysis of yeast deletion mutants using a highly parallel molecular bar-coding strategy," Nature genetics (1996) 14:450-456.
Shults et al., "A multiplexed protein kinase assay," Chem Bio Chem (2007) 8:933-942.
Sievertzon et al., "Transcriptome analysis in primary neural stem cells using a tag cDNA amplification method," BMC Neuroscience, Dec. 2005, 6: 28.
Simonis et al., "Nuclear organization of active and inactive chromatin domains uncovered by chromosome conformation capture-on-chip (4C)," Nat Genet., Nov. 2006, 38(11):1348-54.
Slomovic et al., "Addition of poly(A) and poly(A)-rich tails during RNA degradation in the cytoplasm of human cells," Proc Natl Acad Sci USA, Apr. 2010, 107(16):7407-12.
Slonim and Yanai, "Getting started in gene expression microarray analysis," Plos Computational Biology, 2009, 5(10):e1000543.
Soderberg et al. "Characterizing proteins and their interactions in cells and tissues using the in situ proximity ligation assay, " Methods, Jul. 2008, 45(3):227-232.
Soderberg et al., "Direct observation of individual endogenous protein complexes in situ by proximity ligation," Nature Methods, 2006, 3:995-1000.
Son et al., "A platform for ultrasensitive and selective multiplexed marker protein assay toward early—stage cancer diagnosis," Nanomedicine, Feb. 7, 2007, 2(1):79-82.
Soni and Meller, "Progress toward ultrafast DNA sequencing using solid-state nanopores," Clin Chem., 2007, 53: 1996-2001.
Spiess et al., "A highly efficient method for long-chain cDNA synthesis using trehalose and betaine," Anal. Biochem., Feb. 2002, 301(2):168-74.
Spurgeon et al., "High Throughput Gene Expression Measurement with Real Time PCR in a Microfluidic Dynamic Array," Plos ONE, 2008, 3(2):e1662.
Stevens Jr. et al., "Enhancement of phosphoprotein analysis using a fluorescent affinity tag and mass spectrometry," Rapid Commun Mass Spectrom, 2005, 19(15):2157-62.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS U S A., May 2009, 106(19):7702-7707.
Stroh et al., "Quantum dots spectrally distinguish multiple species within the tumor milieu in vivo," Nat Med., Jun. 2005, 11(6):678-82.
Subramanian et al., "Gene set enrichment analysis: a knowledge-based approach for interpreting genome-wide expression profiles," PNAS, Oct. 2005, 102(43):15545-15550.
Suh et al., "A simple soft lithographic route to fabrication of poly(ethylene glycol) microstructures for protein and cell patterning," Biomaterials, Feb. 2004, 25(3):557-563.
Sumitomo et al., "Ca2+ ion transport through channels formed by -hemolysin analyzed using a microwell array on a Si substrate," Biosensors and Bioelectronics, 2012, 31(1):445-450.
Summersgill et al., "Fluorescence In Situ Hybridization Analysis of Formalin Fixed Paraffin Embedded Tissues, Including Tissue Microarrays," Chapter 4, Bridger, J. Ed., Methods in Molecular Biology 659, 2010, 51-70, 2010.
Sun et al., "Direct immobilization of DNA probes on non-modified plastics by UV irradiation and integration in microfluidic devices for rapid bioassay," Anal. Bio. Chem., 402: 741-748, 2012.
Surzhik et al., "Template-dependent biosynthesis of poly(G) x poly (C) and its antiviral activity in vitro and in vivo," Antiviral Res., May 1988, 38(2):131-40.
Sutherland et al., "Utility of formaldehyde cross-linking and mass spectrometry in the study of protein-protein interactions," J. Mass Spectrom., Jun. 2008, 43(6):699-715.
Swartz et al., "Interstitial flow and its effects in soft tissues," Annu Rev Biomed Eng., 2007, 9:229-56.
Syková et al., "Diffusion in brain extracellular space," Physiol Rev., Oct. 2008, 88(4):1277-340.
Tai et al., "Replication-competent retrovirus vectors for cancer gene therapy," Front Biosci., Jan. 2008, 13:3083-95.
Takahashi et al., "In Vitro Selection of Protein and Peptide Libraries Using mRNA Display," Nucleic Acid and Peptide Aptamers: Methods and Protocols (2009) 535:293-314 (Ch. 17).
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5: 516-35, 2010.
Taniguchi et al., "Quantitative analysis of gene expression in a single cell by qPCR," Nature Methods, 6, pp. 503-506, 2009.
Tawfik et al., "Man-made cell-like compartments for molecular evolution," Nat Biotechnol., Jul. 1998, 16(7):652-6.
Taylor et al., "Microfluidic local perfusion chambers for the visualization and manipulation of synapses," Neuron., Apr. 2010, 66(1):57-68, 25 pages.
Taylor et al., "Mitochondrial DNA mutations in human disease." Nature Reviews Genetics. May 2005, 6(5):389-402.
Tegtmeyer et al., "Alternative Interactions of the SV40 A Protein with DNA," Virology, 1981, 115:75-87.
Thacker et al., "Alkaline Hydrolysis—Carcass Disposal: A Comprehensive Review," National Agriculture Biosecurity Center, Aug. 2004, Chapter 6, pp. 1-12.
Thiery et al., "Multiplex target protein imaging in tissue sections by mass spectrometry—TAMSIM," Rapid Commun. Mass Spectrom., 2007, 21:823-829.
Thorne et al., "In vivo diffusion analysis with quantum dots and dextrans predicts the width of brain extracellular space," Proc Natl Acad Sci USA, Apr. 2006, 103(14):5567-5572.
Thornton, "High rate thick film growth." Annual review of materials science, Aug. 1977, 7(1):239-60.
Tian et al., "Antigen peptide-based immunosensors for rapid detection of antibodies and antigens," Anal Chem May 26, 2009, 81 (13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Timofeev et al., "Regioselective immobilization of short oligonucleotides to acrylic copolymer gels," Nucleic Acids Res., Aug. 1996, 24(16):3142-8.

(56) References Cited

OTHER PUBLICATIONS

Tolbert et al., "New Methods for Proteomic Research: Preparation of Proteins with N-Terminal Cysteines for Labeling and Conjugation," Angewandte Chemie International Edition, Jun. 17, 2002, 41(12):2171-4.
Totet et al., "Immunocompetent infants as a human reservoir for Pneumocystis jirovecii: rapid screening by non-invasive sampling and real-time PCR at the mitochondrial large subunit rRNA gene," J Eukaryot Microbiol., 2003, pp. 668-669.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Toy et al., "A Simple Plastic Perfusion Chamber for Continuous Maintenance and Cinematography of Tissue Cultures," Experimental Cell Research, 1958, 14:97-103.
Twyman et al., "Techniques Patents for SNP Genotyping," Pharmacogenomics, Jan. 2003, 4(1):67-79.
Tzanetakis et al., "The use of reverse transcriptase for efficient first- and second-strand cDNA synthesis from single- and double-stranded RNA templates," J Virol Methods, Mar. 2005, 24(1-2):73-7.
Ueno et al., "cDNA Display: Rapid Stabilitzation of mRNA Display," Antibody-Drug Conjugates, Methods in Molecular Biology, Jan. 2012, pp. 113-135.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Valencia et al., "mRNA-Display-Based Selections for Proteins with Desired Functions: A Protease-Substrate Case Study." Biotechnology progress, May 2008, 24(3):561-9.
Valley et al., "Optoelectronic tweezers as a tool for parallel single-cell manipulation and stimulation," IEEE Trans Biomed Circuits Syst., Dec. 2009, 3(6):424-31.
Van Gelder et al., "Amplified RNA synthesized from limited quantities of heterogeneous cDNA," Proc. Natl. Acad. Sci. USA 87, 1663-1667, 1990.
Van Ness et al., "A versatile solid support system for oligodeoxynucleotide probe-based hybridization assays", Nucleic Acids Res. 19: 3345-3350, 1991.
Vandenbroucke et al., "Quantification of splice variants using real-time PCR," Nucleic Acids Research, 2001, 29(13):e68, 7 pages.
Vasiliskov et al., "Fabrication of microarray of gel-immobilized compounds on a chip by copolymerization, " Biotechniques, Sep. 1999, 27(3):592-606.
Velculescu et al., "Serial analysis of gene expression." Science, Oct. 20, 1995, 270(5235):484-7.
Vermesh et al., "High-density, multiplexed patterning of cells at single-cell resolution for tissue engineering and other applications," Angew Chem Int Ed Engl, Aug. 2011, 50(32):7378-7380.
Villa et al., "Partial V(D)J Recombination Activity Leads to Omenn Syndrome," Cell, May 29, 1998, 93:885-896.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 3, 1999, 96:9236-9241.
Wade et al., "Genome sequence, comparative analysis, and population genetics of the domestic horse.," Science., 326: 865-7, 2009.
Waichman et al., "Functional immobilization and patterning of proteins by an enzymatic transfer reaction." Analytical chemistry, Jan. 21, 2010, 82(4):1478-85.
Walker et al., "Strand displacement amplification—an isothermal, in vitro DNA amplification technique." Nucleic acids research. Apr. 1, 19921, 1992, 20(7):1691-1696.
Walker et al., Ed., "Chapter 1: Basic Techniques in Molecular Biology," Medical Biomethods Handbook, Humana Press, Totowa, New Jersey, 2005, 19 pages.
Wang et al., "Mutations in NEXN, a Z-disc gene, are associated with hypertrophic cardiomyopathy," Am J Hum Genet., Nov. 2010, 87(5):687-93.
Wang et al., "Paramagnetic microspheres with core-shell-ed structures," Journal of Materials Science, Apr. 2012, 47(16):5946-54.
Wang et al., "Single cell analysis: the new frontier in 'omics'," Trends Biotechnol., 28: 281-90, 2010.
Wang et al., "High-fidelity mRNA amplification for gene profiling." Nature biotechnology. Apr. 2000, 18(4): 457-459.
Wang, "RNA amplification for successful gene profiling analysis," J Transl Med., Jul. 2005, 3:28, 11 pages.
Watanabe et al., "Cellular networks involved in the influenza virus life cycle," Cell Host & Microbe, Jun. 2010, 7(6):427-39.
Waxman et al., "De-regulation of common housekeeping genes in hepatocellular carcinoma," BMC Genomics, 2007, 1-9.
Weichhart et al., "Functional selection of vaccine candidate peptides from Staphylococcus aureus whole-genome expression libraries in vitro," Infection and Immunity, 2003, 71 (8):4333-4641.
Weinreich et al., "Evidence that the cis Preference of the Tn5 Transposase is Caused by Nonproductive Multimerization," Genes and Development, Oct. 1994, 8(19):2363-2374.
Wheeler et al., "Microfluidic device for single-cell analysis," Analytical Chemistry, Jul. 2003, 75(14):3581-3586.
Wiedmann et al., "Ligase chain reaction (LCR)—overview and applications," PCR Methods Appl., Feb. 1994, 3(4):S51-64.
Wikipedia.org [online], "Random hexamer," Jan. 2012, Retrieved on Jan. 21, 2022, retrieved from URL<https://en.wikipedia.org/w/index.php?title=Random_hexamer&oldid=47304223 6>, 1 page.
Williams et al., "Disc electrophoresis in polyacrylamide gels: extension to new conditions of pH and buffer," Annals of the New York Academy of Sciences, Dec. 1964, 121(2):373-381.
Williams, "RAC reviews serious adverse event associated with AAV therapy trial," Mol Ther., Dec. 2007, 15(12):2053-54.
Willi-Monnerat et al., "Comprehensive spatiotemporal transcriptomic analyses of the ganglionic eminences demonstrate the uniqueness of its caudal subdivision," Molecular and Cellular Nueorsciences 37(4):845-856, 2008.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles", Nucleic Acids Res. 15: 2911-2926, 1987.
Wong et al., "Direct Site-Selective Covalent Protein Immobilization Catalyzed by a Phosphopantetheinyl Transferase," J. Am. Chem Soc., 2008, 130:12456-64.
Woo et al., "A Comparison of cDNA, Oligonucleotide, and Affymetrix GeneChip Gene Expression Microarray Platforms," Journal of Biomolecular Techniques, 2004, 15(4), 276-284.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Analyt. Biochem, 2001, 294:169-175.
Wright et al., "Reusable, reversibly sealable parylene membranes for cell and protein patterning," J Biomed Mater Res A., May 2008, 85(2):530-538.
Wu et al., "Detection DNA Point Mutation with Rolling-Circle Amplification Chip," Bioinformatics and Biomedical Engineering (ICBBE), 2010 4th International Conference on IEEE, Piscatway, NJ, USA, Jun. 18, 2010, 1-4 pages.
Xiao et al., "Direct determination of haplotypes from single DNA molecules," Nature Methods, 2009, 6(3):199-201.
Xie et al., "CryoFISH: Fluorescence In Situ Hybridization on Ultrathin Cryosections," Fluorescence in situ Hybridization (FISH), Jul. 2010, pp. 221-230.
Yan et al., "Decorin gene delivery inhibits cardiac fibrosis in spontaneously hypertensive rats by modulation of transforming growth factor-beta/Smad and p38 mitogen-activated protein kinase signaling pathways," Hum Gene Ther., Oct. 2009, 20(10):1190-200.

(56) References Cited

OTHER PUBLICATIONS

Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.

Yeakley et al., "Profiling alternative splicing on fiber-optic arrays," Nature Biotechnology, Apr. 2002, 20(4):353-358.

Yershov et al., "DNA analysis and diagnostics on oligonucleotide microchips," Proc. Natl. Acad. Sci. USA, May 1996, 93(10):4913-4918.

Yet et al., "Cardiac-specific expression of heme oxygenase-1 protects against ischemia and reperfusion injury in transgenic mice," Circ Res., Jul. 2001, 89(2):168-73.

Yin et al., "Genetically encoded short peptide tag for versatile protein labeling by Sfp phosphopantetheinyl transferase," PNAS, 2005, 102(44):15815-20.

Yonezawa et al., "DNA display for in vitro selection of diverse peptide libraries," Nucleic Acids Research , 2003, 31 (19):e118.

Yusof et al., "Inkjet-like printing of single-cells," Lab Chip, Jul. 2011, 11(14):2447-2454.

Zhang et al., "A novel mechanism of transposon-mediated gene activation," PLoS Genet., Oct. 2009, 5(10):e1000689, 10 pages.

Zhang et al., "Binding-induced DNA assembly and its application to yoctomole detection of proteins," Anal Chem (2012) 84(2):877-884.

Zhang et al., "Single-base mutational analysis of cancer and genetic diseases using membrane bound modified oligonucleotides," Nucleic Acids Res., Jul. 1991, 19(14):3929-33.

Zhang et al., "Stripping custom microRNA microarrays and the lessons learned about probe-slide interactions," Anal Biochem., Mar. 2009, 386(2):222-7.

Zheng et al., Origins of human mitochondrial point mutations as DNA polymerase mediated errors. Mutat. Res. 599(1-2): 11-20, 2006.

Zheng, "Spectroscopy-based quantitative fluorescence resonance energy transfer analysis," Methods Mol Biol., 2006, 337:65-77.

Zhou et al., "Genetically encoded short peptide tags for orthogonal protein labeling by Sfp and AcpS phosphopantetheinyl transferases," ACS Chemical Biol., 2007 2 5 : 337-346.

Zhu et al., "Reverse Transcriptase Template Switching: A Smart Approach for Full-Length cDNA Library Construction," BioTechniques, 2001, 30(4): 892-897.

Zieba et al., "Bright-field microscopy visualization of proteins and protein complexes by in situ proximity ligation with peroxidase detection," Clin Chem, Jan. 2010, 56(1):99-110.

Zilberman et al., "Genome-wide analysis of DNA methylation patterns," Development (2007) 134: 3959-3965.

Zuker, "Mfold web server for nucleic acid folding and hybridization prediction," Nucleic Acids Res., Jul. 2003, 31(13):3406-15.

Bao et al., "Fluorescent probes for live-cell RNA detection," Annual review of biomedical engineering, 2009, 11:25-47, 28 pages (Author Manuscript).

Caprioli et al., "Molecular imaging of biological samples: localization of peptides and proteins using MALDI-TOF MS," Anal Chem, Dec. 1, 1997, 69(23):4751-4760.

Chou et al., "Optimization of probe length and the number of probes per gene for optimal microarray analysis of gene expression," Nucleic acids research, 2004, 32(12):e99, 8 pages.

Hodges et al., "High definition profiling of mammalian DNA methylation by array capture and single molecule bisulfite sequencing," Genome Research, Dec. 31, 2009, 19:1593-1605.

Lockhart et al., "Genomics, gene expression and DNA arrays," Nature, Jun. 15, 2000, 405(6788):827-836.

Meyer et al., "Targeted high-throughput sequencing of tagged nucleic acid samples," Nucleic Acids Res., 2007, 35(15):e97.

Preston, "The New Genome Analyzerllx Delivering more data, faster, and easier than ever before," Illumina, Jul. 2009, 23 pages.

Schuster, "Next-generation sequencing transforms today's biology," Nature Methods, Jan. 2008, 5:16-18.

Xu et al., "Aptamer-based microfluidic device for enrichment, sorting, and detection of multiple cancer cells," Anal Chem., Sep. 1, 2009, 81(17):7436-7442, 14 pages (Author Manuscript).

Youtube, "Microarray Hybridization Cassette AHC1x24," youtube.com, retrieved on Jul. 28, 2025, retrieved from URL <https://www.youtube.com/watch?v=spHIUg1jfAs>, 3 pages (with Machine Transcript).

Youtube, "Microarray Wash Tray & Multi-Well Hybridization Cassettes," youtube.com, available on or before Jul. 16, 2015, retrieved on Jul. 28, 2025, retrieved from URL <https://www.youtube.com/watch?v=147Kbe5BsbM>, 5 pages (with Machine Transcript).

Zlatanova et al., "Gel-immobilized microarrays of nucleic acids and proteins: production and application for macromolecular research," DNA Arrays: Methods and Protocols, 2001, 170:17-38.

SPATIALLY ENCODED BIOLOGICAL ASSAYS

CROSS-REFERENCE TO RELATED APPLICATIONS

This application is a continuation of U.S. patent application Ser. No. 17/878,519, filed on Aug. 1, 2022, which is a continuation of U.S. patent application Ser. No. 17/556,588, filed Dec. 20, 2021, now U.S. Pat. No. 11,401,545, which is a continuation of U.S. patent application Ser. No. 17/223,669, filed Apr. 6, 2021, now U.S. Pat. No. 11,208,684, which is a continuation of U.S. patent application Ser. No. 17/030,230, filed Sep. 23, 2020, now U.S. Pat. No. 11,384,386, which is a continuation of U.S. patent application Ser. No. 16/988,284, filed Aug. 7, 2020, now U.S. Pat. No. 10,961,566, which is a continuation of U.S. patent application Ser. No. 16/414,213, filed May 16, 2019, now U.S. Pat. No. 10,787,701, which is a continuation of U.S. patent application Ser. No. 16/402,098, filed May 2, 2019, now U.S. Pat. No. 10,472,669, which is a continuation of U.S. patent application Ser. No. 16/276,235, filed Feb. 14, 2019, now U.S. Pat. No. 10,480,022, which is a continuation application of U.S. patent application Ser. No. 15/187,661, filed Jun. 20, 2016, now U.S. Pat. No. 10,308,982, which is a continuation of U.S. patent application Ser. No. 13/080,616, filed Apr. 5, 2011, now U.S. Pat. No. 9,371,598, which claims the benefit of United States Provisional Patent Application No. 61/321,124, filed Apr. 5, 2010, each of which are herein incorporated by reference.

FIELD OF THE INVENTION

This invention relates to assays of biological molecules, and more particularly to assays for determining spatial distributions of a large number of biological molecules in a solid sample simultaneously.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Comprehensive gene expression analysis and protein analysis have been useful tools in understanding mechanisms of biology. Use of these tools has allowed the identification of genes and proteins involved in development and in various diseases such as cancer and autoimmune disease. Conventional methods such as in situ hybridization and other multiplexed detection of different transcripts have revealed spatial patterns of gene expression and have helped shed light on the molecular basis of development and disease. Other technologies that have enabled the quantitative analysis of many RNA sequences per sample include microarrays (see Shi, et al., Nature Biotechnology, 24(9): 1151-61 (2006); and Slonim and Yanai, Plos Computational Biology, 5(10):e1000543 (2009)); serial analysis of gene expression (SAGE) (see Velculescu, et al, Science, 270 (5235):484-87 (1995)), high-throughput implementations of qPCR (see Spurgeon, et al., Plos ONE, 3(2):e1662 (2008)) and in situ PCR (see Nuovo, Genome Res., 4:151-67 (1995)). As useful as these methods are, however, they do not enable simultaneous measurement of the expression of many genes or the presence and/or activity of multiple proteins at many spatial locations in a sample. Laser capture microdissection has permitted the analysis of many genes at a small number of locations, but it is very expensive, laborious, and does not scale well. Certain PCR assays in a 2D format preserve spatial information (see Armani, et al., Lab on a Chip, 9(24): 3526-34 (2009)), but these methods have low spatial resolution because they rely on physical transference of tissue into wells, which also prevents random access to tissue samples and high levels of multiplexing.

At present, no practical method exists to analyze at high resolution the spatial expression patterns of large numbers of genes, proteins, or other biologically active molecules simultaneously. There is thus a need for reproducible, high-resolution spatial maps of biological molecules in tissues. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The invention encompasses assay systems that provide high-resolution spatial maps of biological activity in tissues. The assay system comprises an assay capable of high levels of multiplexing where encoded probes are provided to a biological sample in defined spatial patterns; instrumentation capable of controlled delivery of reagents according to the spatial patterns; and a decoding scheme providing a readout that is digital in nature. In short, the present invention provides the ability to look at many biological targets in many locations, providing the resolution of in situ hybridization with the highly-parallel data analysis of sequencing.

Thus, in some embodiments, the invention provides an assay system to determine spatial patterns of abundance or activity or both of multiple biological targets at multiple sites in a sample, where the assay system performs the following steps: providing a sample affixed to a support; delivering encoded probes for the multiple biological targets to the multiple sites in the sample in a known spatial pattern, where each encoded probe comprises a probe region that may interact with the biological targets and a coding tag that identifies a location of the site to which the encoded probe was delivered; allowing the encoded probes to interact with the biological targets; separating encoded probes that interact with the biological targets from encoded probes that do not interact with the biological targets; determining all or a portion of a sequence of the encoded probes, and associating the abundance or activity or both of the multiple biological targets to the locations of the sites in the sample.

In particular aspects of the invention the biological targets comprise nucleic acids and the encoded probes are oligonucleotides, and in some aspects, there are two encoded probes for each of the multiple nucleic acid targets. In some aspects, the multiple biological targets comprise proteins, the probe regions of the encoding probes are proteins and the coding tags comprise oligonucleotides. In some aspects the multiple biological targets comprise enzymes. In some aspects the probe regions of the encoded probes comprise antibodies, aptamers or small molecules.

Some aspects of the assay system further comprise an amplification step between the separating step and the determining step. In some aspects, the determining step is performed by nucleic acid sequencing, and in preferred aspects, the sequencing is high-throughput digital nucleic acid sequencing.

In some aspects of the invention, the product of the multiple biological targets being assayed and the multiple sites in the sample is greater than 20, in some aspects product of the multiple biological targets being assayed and the multiple sites in the sample is greater than 50, in some aspects the product of the multiple biological targets being assayed and the multiple sites in the sample is greater than 75, 100, 150, 500, 750, 1,000, 5,000, 10,000, 25,000, 50,000, 100,000, 500,000, or 1,000,000 or more. In other aspects, the sequence of at least fifty thousand encoding probes are determined in parallel, in other aspects the sequence of at least one hundred thousand encoding probes are determined in parallel, in some aspects the sequence of at least five hundred thousand encoding probes are determined in parallel, and in some aspects the sequence of at least one million, ten million, one hundred million, one billion, ten billion, one hundred billion or more encoding probes are determined in parallel.

In some aspects, the known spatial pattern is determined by histological features of the sample. Also in some aspects, software programmed hardware performs at least two steps of the delivering step, the separation step, the determining step and the associating step.

In some aspects, the probe regions of the encoded probes are proteins and the separating step is accomplished by encoded probes that interact with the biological targets being captured by an affinity capture agent. In some aspects the probe regions of the encoding probes are nucleic acids and the separating step is accomplished by a washing of the sample.

In other embodiments there is provided an assay system to determine spatial patterns of abundance or activity or both of multiple nucleic acid targets at multiple sites in a sample, where the assay system performs the following steps: providing a sample affixed to a support; delivering oligonucleotide probes for multiple nucleic acid targets to the multiple sites in the sample in a known spatial pattern; allowing the oligonucleotide probes to hybridize with the nucleic acid targets; washing unhybridized encoded oligonucleotide probes from the sample; delivering one or more encoding agents to locations of the multiple sites in the sample according to a known spatial pattern, where the combination of encoding agents delivered to each site is different; coupling the encoding agents and the oligonucleotide probes to form encoded probes; determining all or a portion of a sequence of the encoded probes using high-throughput sequencing, and associating the abundance or activity or both of multiple biological targets to the locations of multiple sites in the sample.

Other embodiments of the invention provide an assay system to determine spatial patterns of abundance or activity or both of multiple protein targets at multiple sites in a sample, where the assay system performs the following steps: providing a sample affixed to a support; delivering encoded probes for the multiple protein targets to the multiple sites in the sample in a known spatial pattern, where each encoded probe comprises a protein probe region that may interact with the protein targets and a coding tag that identifies a location of the site to which the encoded probe was delivered and the protein probe region of the encoding probe of which the coding tag is part; allowing the encoded probes to interact with the protein targets; separating encoded probes that interact with the protein targets from encoded probes that do not interact with the protein targets; determining all or a portion of a sequence of the encoded probes by high throughput sequencing, and associating the abundance or activity or both of the multiple protein targets to the locations of the multiple sites in the sample.

Other embodiments provide an assay system to determine spatial patterns of abundance or activity or both of multiple biological targets at multiple sites in a sample, where the assay system performs the following steps: providing a sample affixed to a support; delivering encoded probes for the multiple biological targets to the multiple sites in the sample in a known spatial pattern, where each encoded probe comprises a probe region that may interact with the biological targets and a coding tag that identifies a location of the site to which the encoded probe was delivered and identifies the biological target; allowing the encoded probes to interact with the biological targets; determining all or a portion of a sequence of the encoded probes, and associating the abundance or activity or both of the multiple biological targets to the locations of the sites in the sample.

The assay system of the invention can utilize various detection mechanisms, based on the molecules to be detected and the reagents needed for such detection system. Exemplary methods that can be used with the assay systems of the invention are described in more detail below.

DESCRIPTION OF THE FIGURES

FIG. 4A shows two target-specific/encoding oligonucleotide constructs specifically bound to a target nucleic acid of interest in a sample. FIG. 4B shows a scheme for delivering twenty different coding tags, a1 through a10 and b1 through b10, to a sample to form a 10×10 coding tag grid. FIG. 4C shows a tissue section sample to which the coding tags are delivered, forming the coding tag grid in the sample.

DEFINITIONS

Figure 1:
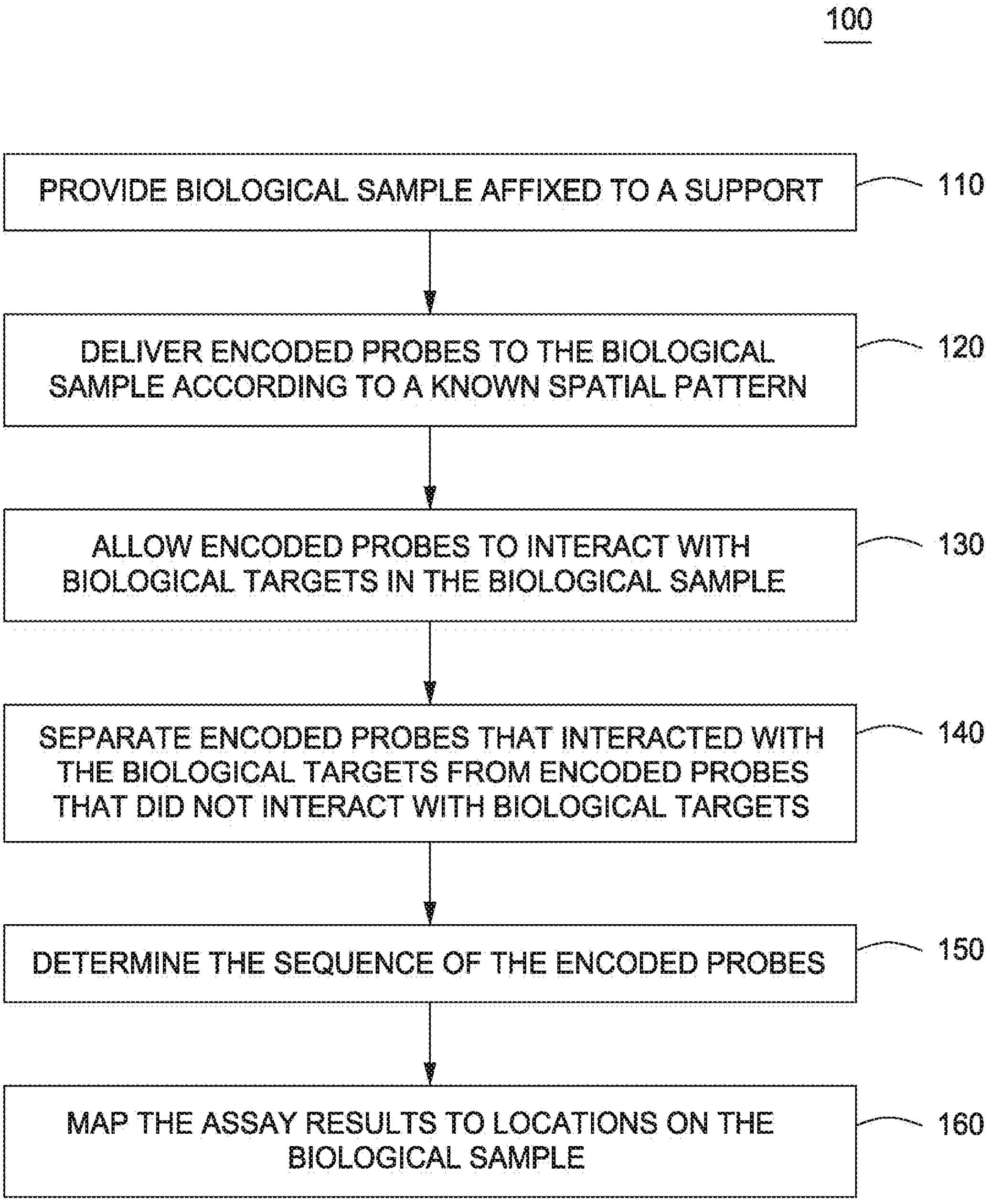
FIG. 1 provides a simplified overview of the assay system of the present invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "antibody" as used herein is intended to refer to an entire immunoglobulin or antibody or any functional fragment of an immunoglobulin molecule which is capable of specific binding to an antigen (antibodies and antigens are "binding partners" as defined herein). "Antibody" as used herein is meant to include the entire antibody as well as any antibody fragments capable of binding the antigen or antigenic fragment of interest. Examples of such peptides include complete antibody molecules, antibody fragments, such as Fab, F(ab')2, CDRS, VL, VH, and any other portion of an antibody which is capable of specifically binding to an antigen. Antibodies for assays of the invention are immunoreactive or immunospecific for, and therefore specifically and selectively bind to, proteins either detected (i.e., biological targets) or used for detection (i.e., probes) in the assays of the invention.

The term "binding agent" as used herein refers to any agent that specifically binds to a biological molecule of interest "Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%).

"Hybridization" refers to the process in which two single-stranded polynucleotides bind non-covalently to form a stable double-stranded polynucleotide, The resulting (usually) double-stranded polynucleotide is a "hybrid" or "duplex," "Hybridization conditions" will typically include salt concentrations of approximately less than 1M, often less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a primer will hybridize to its target subsequence but will not hybridize to the other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01 M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Nucleic acid", "oligonucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

The term "SNP" or "single nucleotide polymorphism" refers to a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present invention and their respective alleles may be derived from any number of sources, such as public databases (U.C. Santa Cruz Human Genome Browser Gateway or the NCBI db SNP website, or may be experimentally determined as described in U.S. Pat. No. 6,969,589; and US Pub. No. 2006/0188875 entitled "Human Genomic Polymorphisms." Although the use of SNPs is described in some of the embodiments presented herein, it will be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele," and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations. It will be further appreciated that references to DNA herein may include genomic DNA, mitochondrial DNA, episomal DNA, and/or derivatives of DNA such as amplicons, RNA transcripts, cDNA, DNA analogs, etc. The polymorphic loci that are screened in an association study may be in a diploid or a haploid state and, ideally, would be from sites across the genome.

The term "selectively binds", "selective binding" and the like as used herein, when referring to a binding partner (e.g. protein, nucleic acid, antibody or other affinity capture agent, etc.), refers to a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular "target" molecule and does not bind in a significant amount to other molecules present in the sample.

"Sequencing", "sequence determination" and the like means determination of information relating to the nucleotide base sequence of a nucleic acid. Such information may include the identification or determination of partial as well as full sequence information of the nucleic acid. Sequence information may be determined "with varying degrees of statistical reliability or confidence. In one aspect, the term includes the determination of the identity and ordering of a plurality of contiguous nucleotides in a nucleic acid, "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, CT); sequencing by ligation (for example, as commercialized in the SOLiD™ technology, Life Technology, Inc., Carlsbad, CA); sequencing by synthesis using modified nucleotides (such as commercialized in TruSee™ and HiSeq™ technology by Illumina, Inc., San Diego, CA, HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA); sequencing of DNA nanoballs (Complete Genomics, Inc., Mountain View, CA); nanopore-based sequencing technologies (for example, as developed by Oxford Nanopore Technologies, LTD, Oxford, UK), and like highly parallelized sequencing methods.

The term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m$=81.5+0.41 (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-4 (1997)) include alternative methods of computation which take structural and environmental, as well as sequence characteristics into account for the calculation of $T_m$.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, *Biochemistry* (4th Ed.) (1995) W. H, Freeman, New York N.Y.; Gait, "*Oligonucleotide Synthesis: A Practical Approach*" (2002) IRL Press, London; Nelson and Cox, Lehninger, *Principles of Biochemistry* (2000) $3^{rd}$ Ed., W. H. Freeman Pub., New York, N.Y,; and Berg, et al., *Biochemistry* (2002) $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a nucleic acid" refers to one or more nucleic acids, and reference to "the assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention, In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The assay systems of the invention provide spatially-encoded, multiplexed assays comprising 1) an assay capable of high levels of multiplexing with an efficient spatial encoding scheme; 2) instrumentation capable of delivering reagents according to a spatial pattern; and 3) decoding determined by a readout that is digital in nature. The assay systems of the invention detect the presence or absence and relative amount of a biological target or biological activity indicative of a biological target, as well as the location of the biological target or activity in a biological sample, e.g., a tissue section or other biological structure disposed upon a support such as a microscope slide or culture dish.

The assay system further provides instrumentation with an ability to deliver reagents in a spatially-defined pattern. This instrumentation, together "with software, reagents and protocols, provides a key component of the highly innovative assay system of the invention, allowing for measurement of numerous biological targets or activities in a meaningful spatial environment, including gene expression and peptide localization, An encoding scheme used in these assay systems allows one to determine the location of biological targets or activity (or lack thereof) in the biological samples after the products of the multiplexed assay are removed from the biological sample and pooled for analysis. Decoding of the encoding scheme can be performed by, e.g., next-generation sequencing, which easily provides millions to trillions of data points at low cost. The assay results such as the amount or activity of biological targets can then be mapped back to specific location in the biological sample. The assay systems open a new analytical window into the complex spatial patterns of cellular function and regulation in biological samples.

A simplified overview of the assay system 100 of the present invention is provided at FIG. 1, At step 110, a biological sample affixed to a support is provided. The biological sample contains biological targets of interest. Biological targets can include any molecule of interest, such as nucleic acids (including, e.g, RNA transcripts, genomic DNA sequences, cDNAs, amplicons, or other nucleic acid sequences) and proteins, enzymes and the like. At step 120, encoded probes are delivered to the biological sample according to a known spatial pattern. Encoded probes comprise probes, which can interact "with biological targets of interest, and coding tags, which identify the positions in the sample of the biological targets being assayed, and thus can be used to link assay results back to locations in the sample. Coding tags in most embodiments are oligonucleotides. However, coding tags may also be mass tags, fluorescent labels, or other moieties.

In some embodiments, the probe and coding tag portions of the encoded probe are pre-coupled before being delivered to the biological sample, For example, in the case where the encoded probes are oligonucleotides, both the probe and coding tag sequence can be synthesized as a single oligonucleotide. Alternatively, the probe and coding tag portions of the encoding probes can be synthesized or obtained separately and combined before delivery to the biological sample (e.g., two separate oligonucleotides can be synthesized and coupled by, e.g., ligation; or an antibody and an oligonucleotide can be prepared separately and conjugated before delivery to the biological sample). Also, as is described in FIGS. 2-5, the probes and the coding tags (in encoding oligonucleotides) are synthesized separately, and are delivered to the biological sample at different steps (e.g., probes first and coding tags thereafter, or vice versa) in the assay.

At step 130, the encoded probes are allowed to react or interact with the biological targets, i.e., conditions are provided to allow e.g., oligonucleotides to hybridize to nucleic acid targets, enzymes to catalyze reactions with protein targets, antibodies to bind epitopes, etc. In the case where the biological targets are nucleic acids, the encoded probes are typically oligonucleotides and hybridize to the target nucleic acids. In the case that the biological targets are proteins, the encoded probes typically are aptamers, small molecules, or oligonucleotide-conjugated proteins that interact with target proteins by binding to them or by reacting with them (that is, one of the proteins is a substrate for the other). Encoding oligonucleotides may be coupled to the probes (proteins) by conjugation, chemical or photo-crosslinking via suitable groups and the like.

Once encoded probes interact with the biological targets, the encoded probes that interacted with the biological targets must be separated from the encoded probes that did not interact with the biological targets at step 140. In the case where the biological targets are nucleic acids and the encoded probes are oligonucleotides, the separation can be accomplished by, e.g., washing the unhybridized encoded probes from the sample. Similarly, for other assays that are based on affinity binding, including those using aptamer, small molecule, and protein probes, washing steps can be used to remove low affinity binders. In the case where the probe is transformed via interaction with the target, e.g., in the case of a peptide, e.g., via cleavage by a protease or phosphorylation by a kinase, it is convenient to collect, all encoded probes—both encoded probes that interacted with the biological targets and were transformed and encoded probes that were not transformed. After collection or pooling, an antibody or other affinity capture agent can be used to capture probes that were transformed by addition of a moiety (e.g., a phosphate group). In cases where probes have been transformed via cleavage, the transformed probes can be separated, e.g., by capturing the non-transformed probes via a tag that is removed from the transformed probes during the transformation (e.g., by cleavage), or by adding a new tag at the site of cleavage.

Once the reacted (transformed) or interacted encoded probes are separated from the unreacted or un-interacted encoded probes, the sequence of the reacted and/or interacted encoded probes is determined at step 150 by, preferably, sequencing. The sequence of the encoded probes allows the mapping of the assay results at step 160 back to locations in the biological sample.

Figure 2:
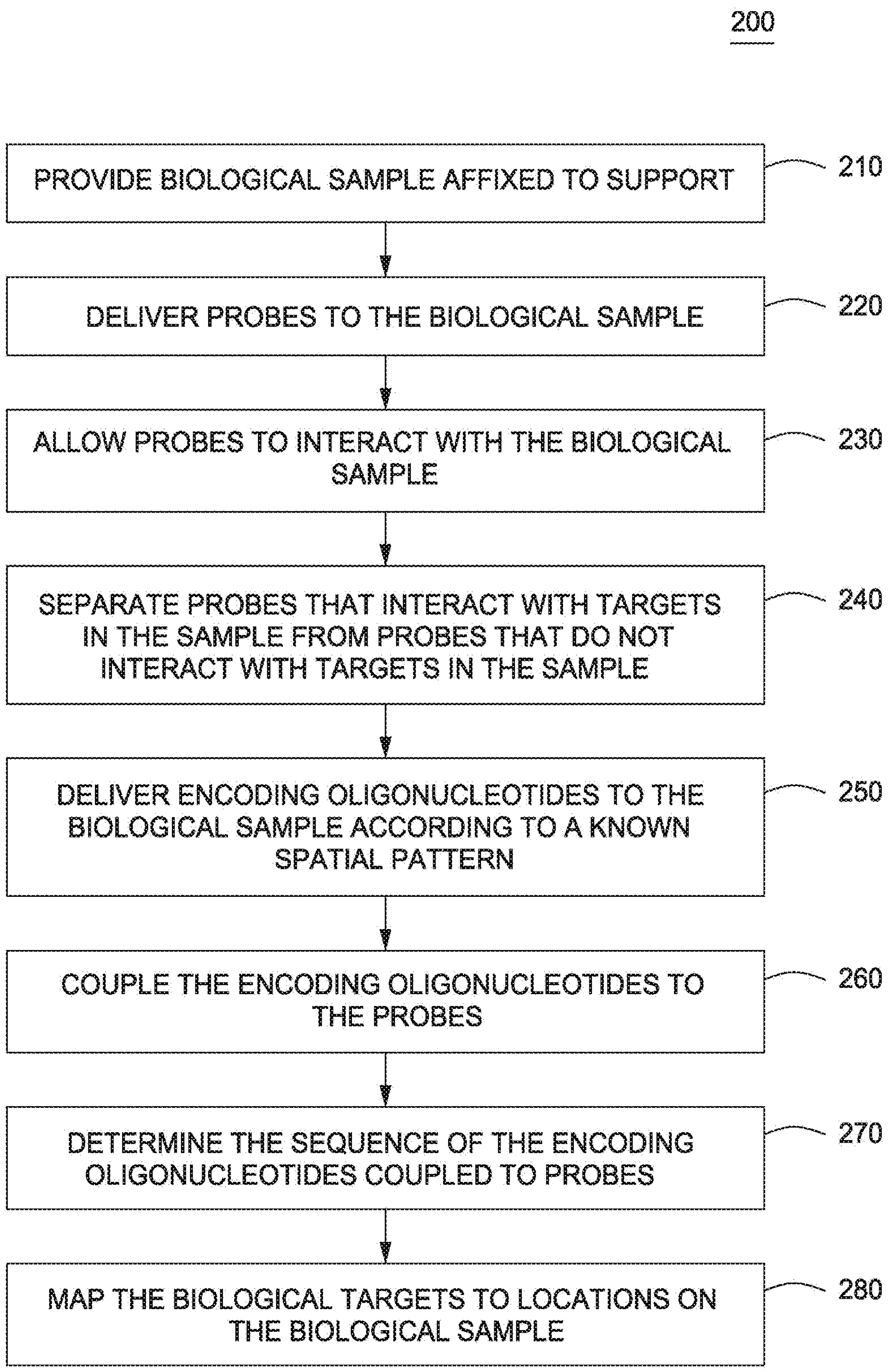
FIG. 2 provides a simplified overview of one embodiment of the assay system of the present invention for detecting nucleic acids.

FIG. 2 provides a simplified overview of an assay system 200 of the present invention embodying an efficient implementation of a combinatorial coding scheme for the encoding of spatial information. For purposes of this overview, the probes are oligonucleotides, but as explained elsewhere, other types of probes can also be used. In step 210, a biological sample affixed to a support, e.g., a tissue sample or other biological structure, is provided. In step 220, one or more oligonucleotide probes are delivered to the biological sample, where the oligonucleotide probes are capable of hybridizing with biological targets in the biological sample. In step 230, the oligonucleotide probes are allowed to interact with (hybridize to) the nucleic acid targets; that is, appropriate conditions are provided where oligonucleotide probes can hybridize to the target nucleic acids.

In step 240, the oligonucleotide probes that did not hybridize to target nucleic acids are removed, and thereby separated from oligonucleotide probes that did hybridize to target nucleic acids. In this embodiment, separation can be accomplished by, e.g., washing the sample to remove unhybridized oligonucleotide probes. Next, in step 250, encoding oligonucleotides (the encoding agents) are delivered to the biological sample according to a chosen spatial pattern, where the encoding oligonucleotides comprise coding tags that are used to encode the location of biological targets in the biological sample. Note that in contrast to the assay system of FIG. 1, here the probes and encoding agents (encoding oligonucleotides) are delivered in separate steps. In step 260, the encoding oligonucleotides are coupled to the oligonucleotide probes to create encoded probes. In this case where the probes are oligonucleotides, the encoding oligonucleotides may be coupled to the oligonucleotides probes by, e.g., ligation. Alternatively, the information in the encoding oligonucleotides can be transferred by using a DNA polymerase to extend a probe oligonucleotide that acts as a primer, and thereby copy and incorporate the sequence of the encoding oligonucleotides.

In step 270, the sequence of the coding tags in the encoded probes as well as the sequence or a portion of the sequence of the probe itself is determined, and in step 280, the target nucleic acids are mapped back to the biological sample. In some embodiments, the abundance of sequences reveals the relative quantity of biological targets at the location. Although this embodiment shows the individual steps in a particular order, so as to better explain the invention, the precise order of the steps can be varied. For example, steps 220 and 250 can be combined, so that a mixture of the probes and encoding oligonucleotides is delivered according to a chosen spatial pattern. Coupling step 260 can then be carried out immediately after the combined steps 220 and 250, or concomitantly with them. In this case, step 240 would then occur after step 260. It can therefore be appreciated that the two key results of this series of steps, i.e., the location-specific encoding of probe molecules and the separation of probe molecules based on their ability to interact with corresponding target molecules, can be accomplished with some flexibility in the implementation of the particular steps. Similarly, there is considerable flexibility in the design of the coding scheme. As described infra, the assays of the invention are particularly amenable to combinatorial methods.

Thus, the present invention provides an ability to look at many different biological targets in many locations, providing the resolution of in situ hybridization with the highly-parallel data analysis of sequencing. In some embodiments, the sum of the multiple biological targets being assayed and the multiple sites in the biological sample is greater than 20, in other embodiments, the sum of the multiple biological targets being assayed and the multiple sites in the biological sample is greater than 50, in other embodiments, the sum of the multiple biological targets being assayed and the multiple sites in the biological sample is greater than 100, greater than 500, 1,000, 10,000, 25,000, 100,000, 500,000, 1,000,000. It will be appreciated that, due to the spatial encoding dimension of the invention, even much larger numbers can be contemplated. For example, assaying 10,000 targets per location×10,000 locations would generate $10^8$ different assays, and even larger numbers than these can easily be contemplated, particularly if spatial locations with resolution on the order of that of single cells are utilized. Further, in embodiments where high-throughput digital sequencing is employed, the sequences of at least 1,000 encoding probes are typically determined in parallel. More typically, using a digital readout, it is desirable to obtain multiple sequence reads for each assay (defined by a probe and a spatial location code). It is desirable to obtain an average of at least 3 copies per assay, and more typically at least 10 or at least 30 copies per assay, depending on the design of the experiment and requirements of the assay. For a quantitative readout with suitable dynamic range, it may be desirable to obtain at least 1,000 reads per assay. Therefore, if 1,000,000 assays are carried out, the number of sequence reads may be 1 billion or more. With high-throughput digital sequencing, and allowing for redundancy, the sequence of at least 10,000 encoding probes are determined in parallel, or the sequence of at least 100,000, 500,000, 1,000,000, 10,000,000, 100,000,000, 1,000,000,000 or more encoding probes are determined in parallel.

Assays

The assay portion of the assay systems of the present invention comprise the following general steps: delivering probes and encoding agents where the encoding agents (in some embodiments pre-coupled to the probes) are delivered to the sample according to a known spatial pattern, allowing the probes to interact or react with biological targets in the sample, and, if the probes and encoding agents have not been pre-coupled, coupling the encoding agents to probes.

The samples of the present invention include virtually any biological sample or samples that can be affixed to a support or provided essentially in a two-dimensional manner, where the ability to tie an assayed biological target or activity back to the location within the biological sample is important. Exemplary biological samples include tissue sections (e.g., including whole animal sectioning and tissue biopsies), cell populations on slides or culture dishes, and the like. The assay systems of the invention are particularly advantageous in that they are compatible with numerous biological sample types, including fresh samples, such as primary tissue sections, and preserved samples including but not limited to frozen samples and paraformalin-fixed, paraffin-embedded (FFPE) samples. An important aspect of the assay systems of the invention is that the biological samples are immobilized on a substrate surface having discrete, independently measurable areas.

The biological targets to be detected can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc.

Figure 3:
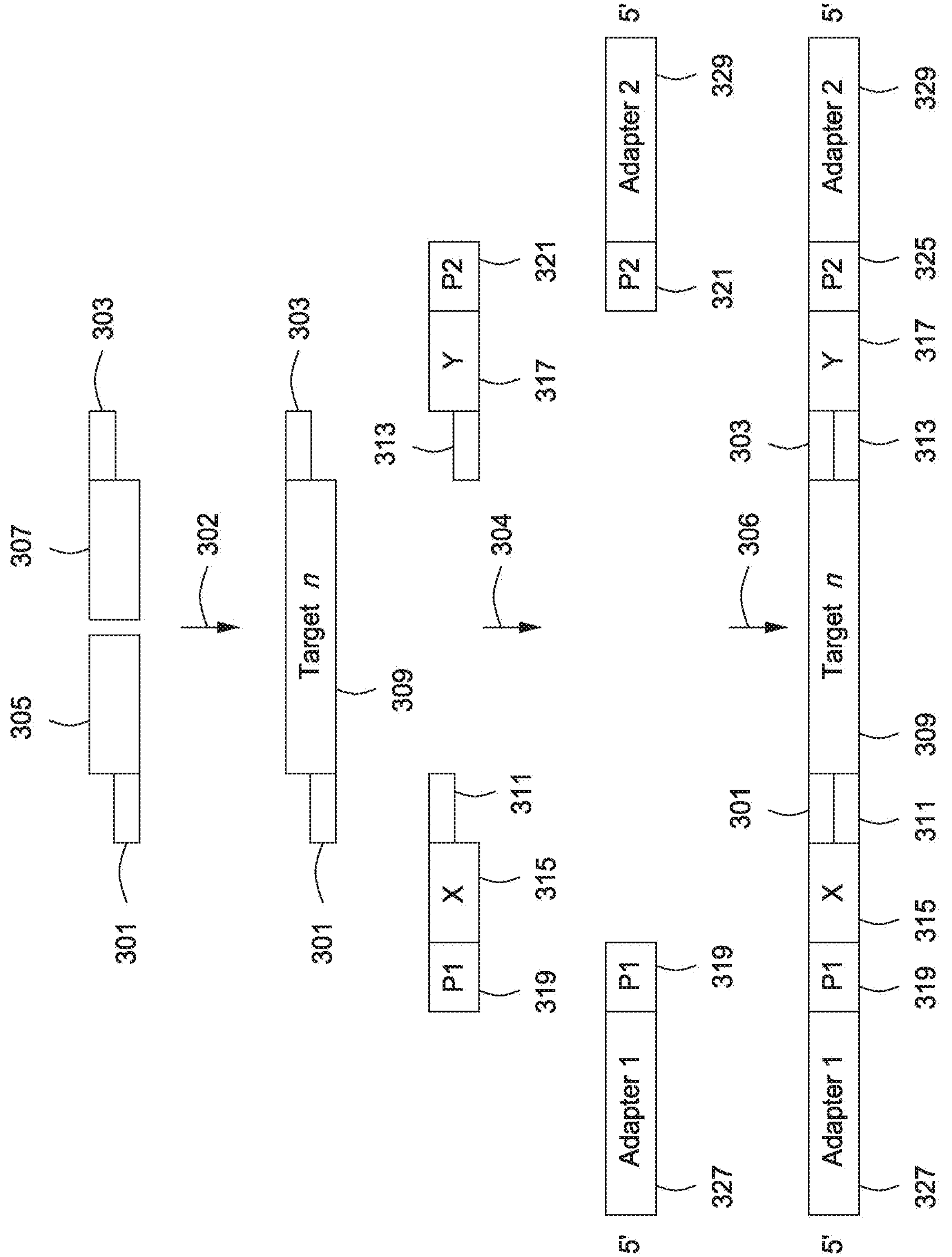
FIG. 3 is a representational depiction of one embodiment of the assay overviewed in FIG. 2.

In some particular embodiments, the assay system is used to analyze nucleic acids, e.g., by genotyping, quantitation of DNA copy number or RNA transcripts, localization of particular transcripts within samples, and the like. FIG. 3 illustrates an overall scheme for an exemplary assay for, e.g., detecting single nucleotide polymorphisms (SNPs) that can be used with the assay system of the invention. In FIG. 3, two oligonucleotide probes are provided. Each oligonucleotide probe comprises a target-specific region (located on either side of the SNP to be analyzed) seen at 305 and 307, and ligation regions, seen at 301 and 303, The oligonucleotide probes are allowed to hybridize to a target nucleic acid (not shown) in the biological sample. At step 302, one of the oligonucleotide probes is extended to incorporate the SNP sequence and ligated to the other probe to form an extended probe comprising target nucleic acid region 309 and ligation regions 301 and 303.

Two encoding agents, both comprising a coding tag (seen at 315 and 317), a ligation region (seen at 311 and 313), and a primer region (seen at 319 and 321) are combined with and ligated to the extended probe at step 304 to form an encoded target-specific oligonucleotide. Again, in contrast with FIG. 1, the probes and encoding agents are delivered at separate steps. Doing so allows use of the combinatorial embodiments described infra. In preferred embodiments, the encoding oligonucleotides within a pair of encoding oligonucleotides ligate specifically to one side of the target sequence or the other (i.e., 5' or 3' of the target sequence) in step 306. Also, typically, the ligation and primer regions of the encoding oligonucleotides and probes are universal; that is, the set of ligation and primer regions used in constructing the probes and encoding oligonucleotides are constant, and only the target-specific regions of the probes and the coding tags of the encoding oligonucleotides differ. However, again in alternative embodiments, the ligation and primer regions are not universal and differ between probes and encoding agents.

Following ligation, the encoded probes are eluted, pooled, and, optionally, sequencing adapters are added to the encoded probes via PCR. In alternative embodiments, sequencing primers may be ligated to the encoding oligonucleotides, or sequencing primer sequences can be included as part of the encoding oligonucleotide. As seen in FIG. 3, each sequencing adapter comprises primer region 319 or 321, compatible with the primer regions 319 and 321 on the encoded probes. The final construct comprising first adapter 327, first primer region 319, first coding tag 315, ligation regions 311 and 301, target region 309, ligation regions 313 and 303, second coding tag 317, second primer region 325 and second adapter 329 is now ready for input into a digital high-throughput sequencing process.

A combination of extension and ligation reactions are exemplified in FIG. 3, but it should be appreciated that a variety of reactions may be used to couple the encoding oligonucleotides to the target-specific oligonucleotides, including ligation only (e.g., for oligonucleotides that hybridize to contiguous portions of the target nucleic acid sequence). Alternatively, an assay utilizing an additional oligonucleotide, such as in the GOLDENGATE® assay (see Fan, et al., Cold Spring Symp. Quant. Biol., 68:69-78 (2003); (Ilumina, Inc., San Diego, CA)), may be employed.

In other embodiments, the assay system of the invention also can be used to analyze peptides or proteins, the presence of antibodies, enzymatic and other protein activities, post-translational modifications, active and non-active forms of peptides, as well as peptide isoforms in a biological sample. Accordingly, the probes may comprise an active region of an enzyme, a binding domain of an immunoglobulin, defined domains of proteins, whole proteins, synthetic peptides, peptides with introduced mutations, aptamers and the like.

In certain aspects, the probes are substrates for enzymes or proenzymes, e.g., kinases, phosphatases, zymogens, proteases, or fragments thereof. In certain aspects, the probes are phosphorylation substrates used to detect proteins involved in one or more signal transduction pathways, e.g., a kinase or a phosphatase. In another specific aspect of the invention, the probes are specific protease substrates that associate only with individual proteases or classes of proteases. In other aspects, the probes are different processed forms, isoforms and/or domains of an enzyme. Protein-based probes are typically conjugated or otherwise linked to oligonucleotide encoding agents. The oligonucleotide encoding agents in this case would also include a nucleotide sequence component that allows for identification of the protein probe.

In certain aspects, the present invention provides assays for evaluating differences in the amount and/or activity of biological targets between different locations in a sample and/or between samples. The method includes determining a plurality of encoded results from the biological sample and evaluating the differences in quantity of the biological targets at each location in the biological sample.

Combinatorial Embodiments

To maximize the efficiency of encoding, a combinatorial approach using pairs of coding tags in the encoding oligonucleotides can be used. By de-coupling the target-specific information and the coding tags, the number of oligonucleotides required is dramatically reduced, with a concomitant decrease in cost.

Figure 4A:
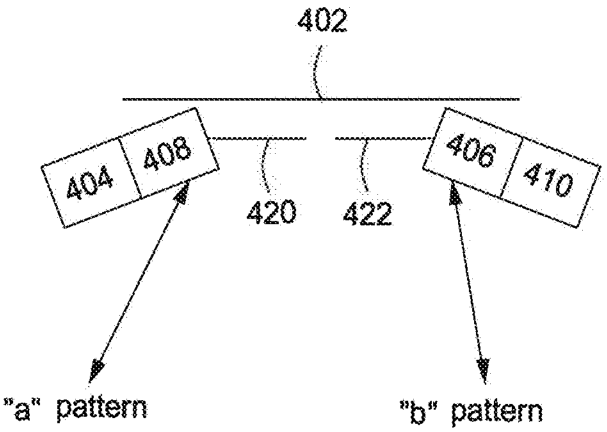
FIG. 4A-C illustrates a general mechanism for one embodiment of a combinatorial encoding scheme of the assay systems of the invention.
Figure 4B:
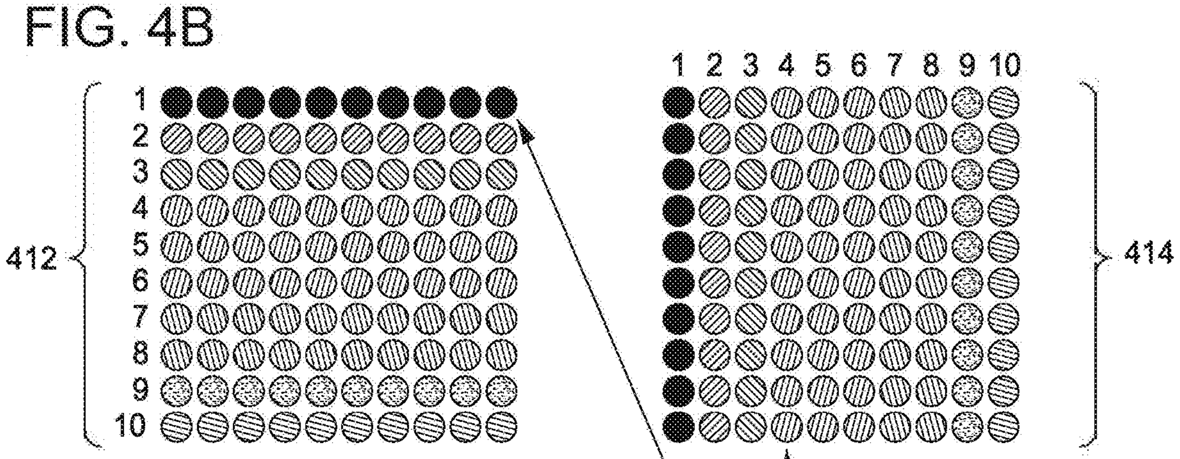
Figure 4C:
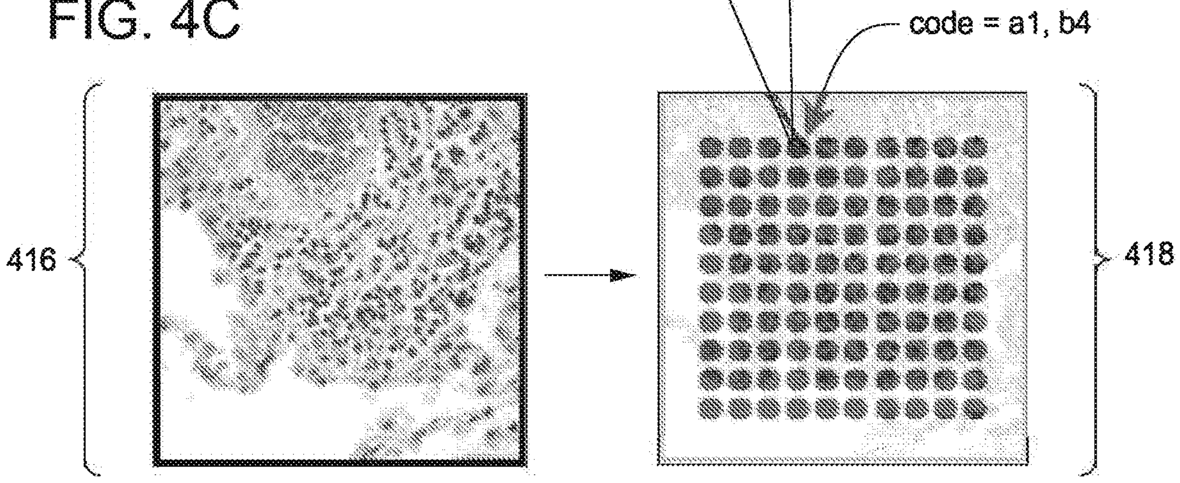

FIG. 4 illustrates a general mechanism for one embodiment of a combinatorial encoding scheme of the assay systems of the invention, where nucleic acids in a representative tissue section (shown at 416) are assayed. FIG. 4 at A shows two target-specific/encoding oligonucleotide constructs 420 and 422 (e.g., formed between steps 302 and 304 of FIG. 3) specifically bound to a target nucleic acid 402 of interest, The first encoded probe 420 comprises coding tag 408, associated with, e.g., a universal priming site for amplification of the assay products or an adapter to enable identification of the coding identifiers using sequencing technologies 404. The second encoded probe 422 comprises coding tag 406, associated with, e.g., a universal priming site for amplification of the assay products or an adapter to enable identification of the coding identifiers using sequencing technologies 410.

FIG. 4 at B shows the spatial pattern that may be used for twenty different coding tags, a1 through a10 (coding tag 406 on encoded probe 420) and b1 through b10 (coding tag 408 encoded probe 422). Coding tag a1., for example, is deposited on the biological sample in ten discrete areas or spots (shown as the first horizontal line of spots in 412). Coding tag a2 is deposited on the biological sample in ten spots on the second horizontal line in 412. Coding tag a3 is deposited on the biological sample in ten spots on the third horizontal line in 412, and so on. Whereas the "a" tags are deposited in ten horizontal rows, the "b" tags are deposited in ten vertical rows as shown in 414. For example, coding tag b1 is deposited on the biological sample in ten discrete spots in the first vertical row of 414, coding tag b2 is deposited on the biological sample in ten discrete spots in the second vertical row of 414, and so on. Using such a configuration allows for twenty coding tags to uniquely define 100 different locations on the biological sample.

FIG. 4 at C shows a representative tissue section 416 coincident with coding tag grid 418. The arrows show how the "a" coding tags and the "b" coding tags are deposited on grid 418 that is coincident with tissue section 416. If, once sequenced, coding tags a1 and b4, e.g., are associated with a target nucleic acid sequence, then that target nucleic acid sequence (i.e., biological target) was present in the tissue section at location a1, b4.

Figure 5:
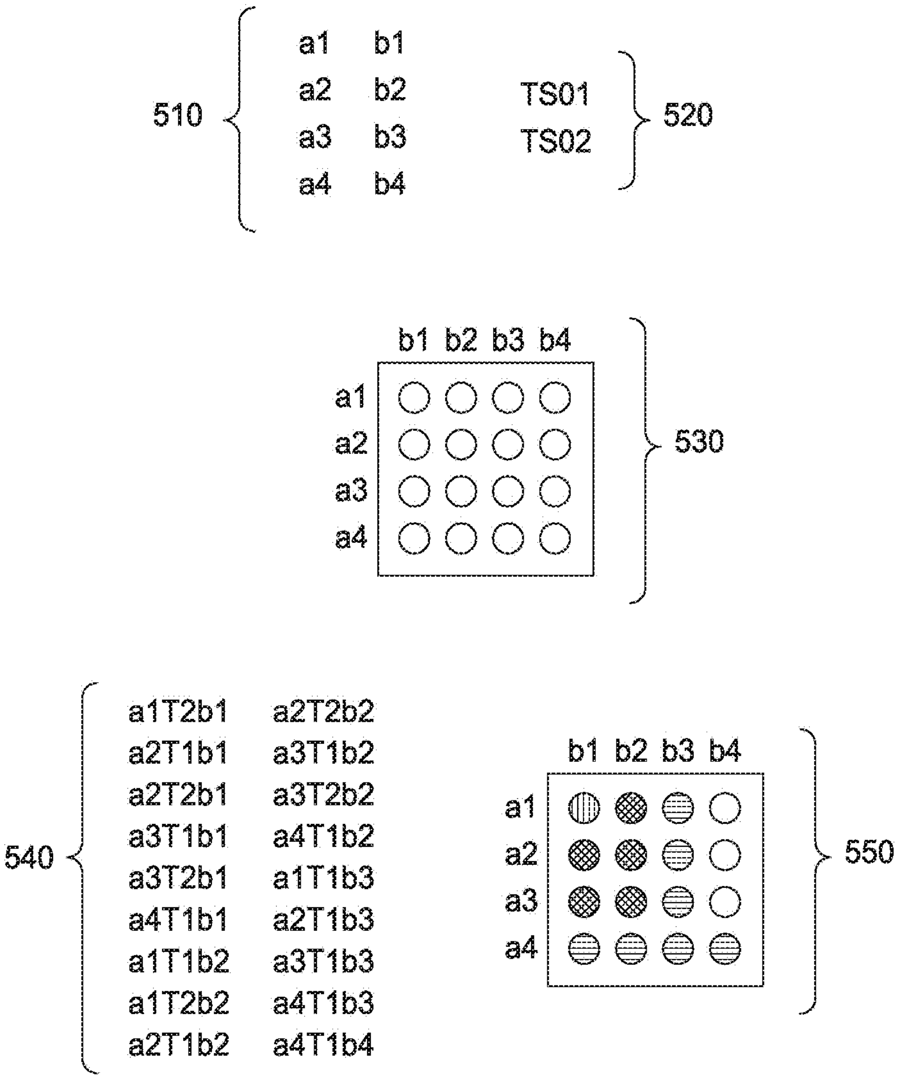
FIG. 5 provides a simplified, specific example of the embodiment of a combinatorial encoding scheme shown in FIG. 4.

FIG. 5 provides a simplified, specific example of the encoding scheme of the assay systems of the invention. FIG. 5 shows encoding oligonucleotides 510, comprising a2, a2, a3, a4 and b1, b3, b3 and b4. Target-specific oligonucleotides (TSOs) (probes) 1 and 2 are shown at 520. A deposit or dispensing scheme is shown at 530. Like the grid exemplified in FIG. 4, encoding oligonucleotides a1 through a4 are deposited in spots in a pattern (here, in a vertical pattern), and encoding oligonucleotides b1 through b4 are deposited in spots in a pattern (here, a horizontal pattern). The grid though shown as a square with spots is actually a deposition pattern on a biological sample (not shown) such as tissue section 416 shown in FIG. 4.

The target-specific oligonucleotides are delivered to the biological sample, where the target-specific oligonucleotides hybridize to target nucleic acids in the biological sample if target nucleic acids are present. Unhybridized target-specific oligonucleotides are then removed, e.g., by washing. The encoding oligonucleotides are then delivered to the biological sample according to the spatial pattern shown at 530. The encoding oligonucleotides are ligated (or, e.g., extended and ligated) to any target-specific oligonucleotides that hybridized to the target nucleic acid in the biological sample, the ligated constructs are then eluted from the biological sample, pooled, and sequencing adapters are added through, e.g., PCR or ligation, if the sequences were not previously included in the encoding oligonucleotides. The ligated constructs are sequenced by, e.g., high throughput or "next generation" sequencing.

The pool of resulting sequences is shown at 540. A sequence readout was obtained for target-specific oligonucleotide 1 only at a4b1, a4b2, a1b3, a2b3, a3b3, a4b3 and a4b4 (positions shown with horizontal lines). A sequence readout was obtained for target-specific oligonucleotide 2 only at a1b1 (position shown with vertical lines). A sequence readout was obtained for both target-specific oligonucleotides 1 and 2 at positions a2b1, a3b1, a1b2, a2b2, and a3b2 (positions shown with cross-hatching). No sequence readout was obtained for either target-specific oligonucleotides at a1b4, a2b4 or a3b4 (positions shown without shading). Thus, in the biological sample on which the assay took place the first target nucleic acid was detected in a large portion of the left side and at the bottom of the biological sample, the second target nucleic acid was detected only in the upper left portion of the biological sample, and neither target nucleic acid was detected in the upper right portion of the biological sample. The differential expression of the two target nucleic acids now can be mapped back to the biological sample and to the biological structures or cell types in these locations in the biological sample, as shown in 550.

In addition to location information, information relating to relative abundance of the encoded tags can be obtained. For example, if it is found that there are ten times as many a4T1b1 sequences occurring in the data set as compared to a4T1b2 sequences, this would indicate that target nucleic acid sequence 1 is ten times more abundant at the a4T1b1 location than at the a4T1b2 location.

In the case of nucleotide analysis as shown in FIG. 3, by ligating the coding tags directly to target-specific oligonucleotides, only 2n target-specific oligonucleotides are needed for n targets. For example, using the combinatorial approach outlined in FIG. 2, assaying 100 different targets at 10,000 spatial locations would require 2×100 target-specific oligonucleotides and 2×100 encoding oligonucleotides. The total count of assay oligonucleotides would be only 400 (200 target-specific and 200 encoding), not counting universal primers. In contrast, if the coding oligonucleotides were not decoupled from the target-specific oligonucleotides, (n×X positional codes)+(n×Y positional codes) would be needed, or in the above example, 20,000 oligonucleotides, not counting universal primer sequences. Moreover, though the embodiments shown in FIGS. 2-5 depict a combinatorial scheme using two encoding agents (coding tags), three, four or more encoding agents and coding tags may be used, and attached to the probe or one another by varying means and in varying combinations of steps.

Due to the spatial encoding aspect of the assay system of the invention, a large amount of information can be generated with even a modest number of assays. For example, five or more biological targets assayed at five or more positions in the sample generates 25 or more combinations. Using digital sequencing as a readout, the optimum number of sequence reads per combination depends on the sensitivity and dynamic range required, and can be adjusted, For example, if for each combination on average 100 reads are sampled, the total for 25 combination is 25,000 reads. If 1,000 targets are assayed at 1,000 locations with an average sampling depth of 1,000, then $10^9$ reads are required. These numbers, although large, are within the capacity of intrinsically parallel digital sequencing methods, which can generate datasets of billions or even trillions of reads in a reasonable timeframe and at a very low cost per read. Therefore, by varying the numbers of positions interrogated or biological targets assayed, or both, and using digital sequencing, large amounts of information can be obtained. In specific aspects, multiple locations are interrogated for two or more biological molecules.

Reagent Delivery Systems

The reagent delivery system of the invention includes instrumentation that allows the delivery of reagents to discrete portions of the biological sample, maintaining the integrity of the spatial patterns of the encoding scheme. Reagent delivery systems of the assay systems of the invention comprise optional imaging means, reagent delivery hardware and control software. Reagent delivery can be achieved in a number of different ways. It should be noted that reagent delivery may be to many different biological samples at one time. A single tissue section has been exemplified herein; however, multiple biological samples may be affixed and analyzed simultaneously. For example, pions of a tissue sample can be analyzed in parallel and the data combined to build a 3D map.

Integral to the assay system of the invention is instrumentation that allows for spatial patterning of reagents onto the biological sample. Technologies for formulating and delivering both biological molecules (e.g. oligonucleotides or antibodies) and chemical reagents (e.g., small molecules or dNTPs) are known in the art, and uses of these instrument systems are known to one skilled in the art and easily adaptable to the assay systems of the invention. One example of a suitable reagent delivery system is the Labcyte™ Echo acoustic liquid handier, which can he used to deliver nanoliter scale droplets containing biological molecules with high precision and reproducibility. One skilled in the art could incorporate this reagent delivery device into the overall system, using software to specify the locations to which reagents should be delivered.

Other instruments that can be used for the deposition of agents and/or coding identifiers onto biological samples include, but are not limited to, ink jet spotting; mechanical spotting by means of pin, pen or capillary; micro contact printing; photochemical or photolithographic methods; and the like. For several applications, it may be preferred to segment or sequester certain areas of the biological samples into one or more assay areas for different reagent distributions and/or biological target determination. The assay areas may be physically separated using barriers or channels.

In one exemplary aspect, the reagent delivery system may be a flow-based system. The flow-based systems for reagent delivery in the present invention can include instrumentation such as one or more pumps, valves, fluid reservoirs, channels, and/or reagent storage cells. Reagent delivery systems are configured to move fluid to contact a discrete section of the biological sample. Movement of the reagents can be driven by a pump disposed, for example, downstream of the fluid reagents. The pump can drive each fluid reagent to (and past) the reaction compartment. Alternatively, reagents may be driven through the fluid by gravity. US Pub. Nos. 20070166725 and 20050239192 disclose certain general-purpose fluidics tools that can be used with the assay systems of the invention, allowing for the precise manipulation of gases, liquids and solids to accomplish very complex analytical manipulations with relatively simple hardware.

In a more specific example, one or more flow-cells can be attached to the substrate-affixed biological sample from above. The flow-cell can include inlet and outlet tubes connected thereto and optionally an external pump is used to deliver reagents to the flow-cell and across the biological sample. The flow cells are configured to deliver reagents only to certain portions of the biological sample, restricting the amount and type of reagent delivered to any specific section of the biological sample.

In another aspect, a microfluidic system can be integrated into the substrate upon which the biological sample is disposed or externally attached on top of the substrate. Microfluidic passages for holding and carrying fluid may be formed on and/or above the planar substrate by a fluidics layer abutted to the substrate. Fluid reagents can be selected and delivered according to selective opening and closing of valves disposed between reagent reservoirs.

Pumps generally include any mechanism for moving fluid and/or reagents disposed in fluid. In some examples, the pump can be configured to move fluid and/or reagents through passages with small volumes (i.e., microfluidic structures). The pump can operate mechanically by exerting a positive or negative pressure on fluid and/or on a structure carrying fluid, electrically by appropriate application of an electric field(s), or both, among other means. Exemplary mechanical pumps may include syringe pumps, peristaltic pumps, rotary pumps, pressurized gas, pipettors, etc. Mechanical pumps may be micromachined, molded, etc. Exemplary electrical pumps may include electrodes and may operate by electrophoresis, electroendoosmosis, electrocapillarity, dielectrophoresis (including traveling wave forms thereof), and/or the like.

Valves generally include any mechanism for regulating the passage of fluid through a channel. Valves can include, for example, deformable members that can be selectively deformed to partially or completely close a channel, a movable projection that can be selectively extended into a channel to partially or completely block a channel, an electrocapillary structure, and/or the like.

An open gasket can be attached to the top of the biological sample and the sample and reagents can be injected into the gasket. Suitable gasket materials include, but are not limited to, neoprene, nitrile, and silicone rubber. Alternatively, a watertight reaction chamber may be formed by a gasket sandwiched between the biological sample on the substrate and a chemically inert, water resistant material such as, but not limited to, black-anodized aluminum, thermoplastics (e.g., polystyrene, polycarbonate, etc), glass, etc.

In an optional embodiment, the assay system comprises imaging means to determine features and organization of the biological sample of interest. The images obtained, e.g., may be used to design the deposition pattern of the reagents, Imaging means are optional, as an individual can instead view the biological sample using, e.g., a microscope, analyze the organization of the biological sample, and specify a spatial pattern for delivery assay reagents. If included, the delivery system can comprise a microcircuit arrangement including an imager, such as a CCD or IGFET-based (e.g., CMOS-based) imager and an ultrasonic sprayer for reagent delivery such as described in US Pub. No. 20090197326, which is incorporated herein by reference. Also, it should be noted that although FIGS. 4 and 5 illustrate using a x,y grid configuration, other configurations can be used, such as, e.g., following the topology of a tissue sample; targeting certain groups of cells, cell layers and/or cell types in a tissue, and the like.

In yet another alternative, the reagent delivery system controls the delivery of reagents to specific patterns on a biological sample surface using semiconductor techniques such as masking and spraying. Specific areas of a biological sample can be protected from exposure to reagents through use of a mask to protect specific areas from exposure. The reagents may be introduced to the biological sample using conventional techniques such as spraying or fluid flow. The use of masked delivery results in a patterned delivery scheme on the substrate surface.

In a preferred aspect of the invention, the reagent delivery instrumentation is based on inkjet printing technology. There are a variety of different ink-jetting mechanisms (e.g., thermal, piezoelectric) and compatibility has been shown with aqueous and organic ink formulations. Sets of independently actuated nozzles can be used to deliver multiple reagents at the same time, and very high resolutions are be achieved.

In order to target specific sites of interest, an informative image of the biological sample to be assayed may be used to assist in the reagent delivery methods and associated encoding scheme. Sample regions of the biological sample can be identified using image processing (e.g., images of cell types differentiated by immunohistochemistry or other staining chemistries) integrated with other features of the assay system. In some aspects, software is used to automatically translate image information into a reagent delivery pattern. A mechanism to register and align very precisely the biological sample for reagent delivery is thus an important component of the assay systems of the invention. Mechanisms such as the use of fiducial markers on slides and/or other very accurate physical positioning systems can be adapted to this purpose.

The invention preferably comprises a complete suite of software tailored to the assay system. Optionally, oligonucleotide design software is used to design the encoding nucleotides (and in embodiments where nucleic acids are assayed, the target-specific oligonucleotides) for the specific assay to be run, and may be integrated as a part of the system. Also optionally, algorithms and software for reagent delivery and data analysis (i.e., sequence analysis) may be integrated to determine assay results. Integrated data analysis is particularly useful, as the type of dataset that is generated may be massive as a consequence of scale. Algorithms and software tools that are specifically designed for analysis of the spatially-associated data generated by the assay systems, including pattern-analysis software and visualization tools, enhance the value of the data generated by the assay systems.

In certain aspects, the assay system comprises processes for making and carrying out the quality control of reagents, e.g., the integrity and sequence fidelity of oligonucleotide pools. In particular, reagents are formulated according to factors such as volatility, stability at key temperatures, and chemical compatibility for compatibility with the reagent delivery instrumentation and may be analyzed by instrumentation integrated within the assay system.

Sequencing

Numerous methods can be used to identify the coding tags and probe sequences in the encoded probes of the assay systems of the invention. The coding tags can be detected using techniques such as mass spectroscopy (e.g., Maldi-T of, LC-MS/MS), nuclear magnetic resonance imaging, or, preferably, nucleic acid sequencing. Examples of techniques for decoding the coding tags of the present invention can be found, for example, in US Pub. No. 20080220434, which is incorporated herein by reference. For example, the coding tags may be oligonucleotide mass tags (OMTs or massTags). Such tags are described, e.g., in US Pub. No. 20090305237, which is incorporated by reference in its entirety. In yet another alternative, the encoded probes can be amplified and hybridized to a microarray. This would require separate amplification reactions to be carried out, in which each amplification is specific to a particular spatial code or subset of codes, accomplished by using code-specific primers. Each amplification would also incorporate a different resolvable label (e.g. fluorophor). Following hybridization, the relative amounts of a particular target mapping to different spatial locations in the sample can he determined by the relative abundances of the resolvable labels.

In one particularly preferred aspect, the resulting coding tags according to the assay system are substrates for high-throughput, next-generation sequencing, and highly parallel next-generation sequencing methods are used to confirm the sequence of the coding tags, for example, with SOLiD™ technology (Life Technologies, Inc.) or Genome Ananlyzer (Illumina, Inc.). Such next-generation sequencing methods can be carried out, for example, using a one pass sequencing method or using paired-end sequencing. Next generation sequencing methods include, but are not limited to, hybridization-based methods, such as disclosed in e.g., Drmanac, U.S. Pat. Nos. 6,864,052; 6,309,824; and 6,401,267; and Drmanac et al, U.S. patent publication 2005/0191656; sequencing-by-synthesis methods, e.g., U.S. Pat. Nos. 6,210,891; 6,828,100; 6,969,488; 6,897,023; 6,833,246; 6,911,345; 6,787,308; 7,297,518; 7,462,449 and 7,501,245; US Publication Application Nos. 20110059436; 20040106110; 20030064398; and 20030022207; Ronaghi, et al, Science, 281: 363-365 (1998); and Li, et al, Proc. Natl. Acad. Sci., 100: 414-419 (2003); ligation-based methods, e.g., U.S. Pat. Nos. 5,912,148 and 6,130,073; and U.S. Pat. Appin Nos. 20100105052, 20070207482 and 20090018024; nanopore sequencing e.g., U.S. Pat. Appln Nos. 20070036511; 20080032301; 20080128627; 20090082212; and Soni and Meller, Clin Chem 53: 1996-2001 (2007)), as well as other methods, e.g., U.S. Pat. Appln Nos. 20110033854; 20090264299; 20090155781; and 20090005252; also, see, McKernan, et al., Genome Res., 19:1527-41 (2009) and Bentley, et al., Nature 456:53-59 (2008), all of which are incorporated herein in their entirety for all purposes.

Applications of Assay System

It will be apparent to one skilled in the art upon reading the present disclosure that there are numerous important areas of biological research, diagnostics, and drug development that will benefit from a high throughput multiplexed assay system that can measure simultaneously the amount and spatial location of a biological target in a biological sample. For example, combining the ability to estimate the relative abundance of different RNA transcripts with the ability to reconstruct an image of spatial patterns of abundance across many locations, which may be as small as or even smaller than individual cells, in a tissue enables many different areas of basic research. The following are exemplary uses and are by no means meant to be limiting in scope.

In one example, 3-dimensional patterns of gene expression are determined by analyzing a series of tissue sections, in a manner analogous to image reconstruction in CT scanning, Such a method can be used to measure changes in gene expression in disease pathology, e.g., in cancerous tissue and/or a tissue upon injury, inflammation or infection. With the assay systems of the invention, more detailed information on gene expression and protein localization in complex tissues is obtained, leading to new insights into the function and regulation both in normal and diseased states, and provides new hypotheses that can be tested. For example, an assay system of the invention may enable some of the insights gained from many individual studies and larger programs like ENCODE (Birney, et al., Nature, 447: 799-816 (2007)) and modENCODE to be integrated at the tissue level. The assay systems also aid computational efforts to model interacting networks of gene expression in the field of systems biology.

The assay systems also provide a novel approach to analysis of somatic variation, e.g., somatic mutations in cancer or variability in response to infectious organisms. For example, tumors are typically highly heterogeneous, containing cancer cells as well as genetically normal cells in an abnormal local environment. Cancer cells undergo mutation and selection, and in this process it is not unusual for local clones to develop. Identifying relatively rare somatic mutations in the context of tumors may enable the study of the role of key mutations in the selection of clonal variants. Transcriptional patterns associated with angiogenesis, inflammation, or other cancer-related processes in both cancer and genetically normal cells can be analyzed for insights into cancer biology and assist in the development of new therapeutic agents for the treatment of cancers. In another example, individuals have varying susceptibility to infectious organisms, and the assay systems of the invention can be used to study the interaction between microbes and tissues or the various cell types within the tissue.

Importantly, in addition to providing spatially-associated information, the invention allows a great increase in the sensitivity of detecting rare mutations, as signal to noise can he dramatically increased since only a small location is assayed in any given reaction. In a typical assay for rare mutations in a mixed sample, the sample is treated in bulk, i.e., nucleic acids are extracted from many cells into a single pool. Thus, if a mutation is present in one cell in 10,000, it must be detected against a background of normal DNA from ~10,000 cells. In contrast, with the assay systems of the invention many cells can be analyzed, but individual cells or small groups of cells would be identified by the spatial coding system. Therefore, in the assay systems of the present invention, background is reduced by orders of magnitude, greatly increasing sensitivity. Furthermore, the spatial organization of mutant cells can be observed, which may be particularly important in detecting key mutations in tissue sections in cancer. Already molecular histological analyses are yielding insights into cancer biology and may have potential for use in diagnostics. The technology of the invention promises to greatly increase the power of such approaches.

The present invention provides assays, assay systems, and methods of using such assays in spatially encoded biological assays. The invention provides an assay system comprising one or more agents provided in defined spatial patterns on a substrate surface, and a detection system for identifying the presence or absence, relative amount, and location of a biological molecule. Such biological molecules include, but are not limited to, nucleic acids, peptides, carbohydrates, cellular components, and the like. The assay system is a novel multiplexing approach, as it allows multiple molecules and their respective multiple locations to be identified in a single system using a unique encoding scheme. This encoding scheme uses both molecule-specific binding agents and coding identifiers to provide a practical and cost-effective determination of information on multiple biological molecules, including specific positional information of such molecules in a biological sample, e.g., a tissue section. The single molecule detection analysis using the encoding system also allows relative amounts of biological molecules to be detected, thus providing information on expression levels, sequestering in specific locales, and the like.

The assay systems detect the presence or absence, and relative amount, of a biological molecule at more than one spatial location in a sample. In addition, the assays provide methods for doing this for multiple biological molecules simultaneously. The assay systems utilize one or more binding agents that specifically bind to the biological molecule of interest and unique coding identifiers associated with specific binding agents. The detection system utilizes a method for identifying the presence and spatial address of the agent binding based on the positive and/or negative results that are obtained using detection of the agent and identifier and the encoding scheme of the spatial patterns on the substrate surface. In a specific aspect, the encoding scheme employs limited reagent delivery to the spatial patterns on the substrate surface, and access of the coding identifiers and/or binding agents to portions of the sample is controlled through such limited delivery.

In one aspect, the assay system detects the presence or absence and spatial location of a biological molecule based on the positive and/or negative results that are obtained using limited reagent delivery and the encoding scheme of the spatial patterns on the substrate surface.

The assay system and methods of the invention are based on relational, solid-state substrates with positions that represent specific spatial locations within a biological sample, e.g., a cell, organelle or tissue. The ability to use encoding features to represent locations allows high-throughput analysis of the presence or absence, and relative amount, of a biological molecule at more than one spatial location in a sample. The encoding features also allow provide assaying of multiple biological molecules at these multiple locations simultaneously.

A primary feature of the invention is the preservation of the spatial organization of elements in a sample of interest through the use of an encoding scheme. For example, the assay may be designed to preserve the relative position of cells in a tissue, and the assay may interrogate the individual cells for genomic DNA variation (including epigenetic modifications), and RNA and protein expression.

In one specific aspect, the encoding scheme of the assay system comprises the use of two or more coding patterns, each comprising regions defined by spatial patterns on the substrate surface. For example, the assay system can utilize an encoding scheme that comprises a 2-dimensional grid format based on the discrete positioning of the binding agents in the substrate surfaces. In another example, the spatial patterns may be based on more randomized cell locations, e.g., the patterns on the substrate surface follow an underlying biological structure rather than a strict, x,y grid pattern. This aspect includes systems with two or more substantially identical spatial patterns using different binding agents and/or coding identifiers, as well as systems having different patterns for different agents and/or coding identifiers. The encoding scheme of the systems can be controlled by delivery of different reagents to discrete regions on the substrate surfaces, which allows different reactions to take place on substantially similar agents of known location on the substrate surfaces.

In one specific aspect, the invention provides high resolution, high-throughput analysis of nucleic acids and/or expression levels that provides both detection and spatial identification of large numbers of nucleic acids, e.g., DNA or RNA.

In another specific aspect, the invention provides high resolution, high-throughput analysis of proteins that provides both detection and spatial identification of large numbers of such proteins, e.g., kinases or proteases.

Numerous reagent delivery systems can be used with the assay system of the invention. The primary criteria of such reagent delivery systems is the ability to direct delivery of specific agents based on spatial patterns on the substrate surface.

In one preferred aspect, the encoding scheme utilizes a reagent delivery system based on printing and informatics technologies to implement the spatial patterns used for identification and localization of the biological materials. For example, the patterns found in the encoding scheme may be created using ink jet printing technology to provide reagents at specific locations on one or more substrate surfaces. The desired patterns are set out in specific coding patterns on the substrate surface.

In certain aspects of the invention, the binding agents are immobilized directly to the substrate surface, and the location of the binding agents is known or determined prior to use of the substrate surface in the assay system. In another aspect, the binding agents are immobilized onto beads or other separate structural elements that are then provided in known locations on the substrate surface. In yet another aspect, the binding agents may be provided in or on features of the substrate surface, e.g., provided in wells or channels.

In specific aspects of the invention, the binding agents are nucleic acids immobilized directly or indirectly to the substrate surface, e.g., directly through the use of amino groups on the substrate surface or indirectly through the use of a linker. The location of the nucleic acid sequences is known or determined prior to use of the substrate surface in the assay system. In another specific aspect, the nucleic acids may be immobilized directly or indirectly onto beads that are then provided in known locations on the substrate surface. In yet another aspect, the nucleic acids may be provided in or on features of the substrate surface, e.g., provided in wells.

In these aspects involving nucleic acid agents, any methods of sequence determination can be used, e.g., sequencing, hybridization and the like. In a preferred aspect, nucleic acid sequencing, and preferably next-generation sequencing, is used to decode the spatial encoding scheme in the assay system of the invention. This provides a very wide dynamic range for very large numbers of assays, allowing for efficient multiplexing.

In some aspects, the assay utilizes two or more oligonucleotides, the oligonucleotides comprising a universal primer region and a region that correlates specifically to a single spatial pattern within the spatial encoding scheme. In a specific aspect, the assay comprises two allele specific oligonucleotides and one locus specific oligonucleotides. These oligonucleotides allow the identification of specific SNPs, indels or mutations within an allele. This is useful in the identification of genetic changes in somatic cells, genotyping of tissues, and the like.

In other specific aspects of the invention, the binding agents are peptides. In one aspect, these peptides are associated directly or indirectly to known locations on a substrate surface, e.g., using binding protein pairs or through oligonucleotide linkers complementary to oligonucleotides on the substrate surface. In another aspect, the binding agents are peptides are immobilized directly or indirectly onto beads or other separate structural elements that are then provided in known locations on the substrate surface. In yet another aspect, the peptides may be provided in or on features of the substrate surface, e.g., provided in wells.

In yet other specific aspects of the invention, the binding agents are chemical entities (e.g., small molecules) that are coded, e.g. using sequence tags or mass spectroscopy tags as coding identifiers. In one aspect, these chemical entities can be are immobilized directly to the substrate surface. In another aspect, the binding agents are immobilized onto beads or other separate structural elements that are then provided in known locations on the substrate surface. In yet another aspect, the binding agents may be provided in or on features of the substrate surface, e.g., provided in wells.

The assay system of the invention can utilize various detection mechanisms, based on the molecules to be detected and the reagents needed for such detection system. Exemplary methods that can be used with the assay systems of the invention are described in more detail below.

The Invention in General

The assay system and methods of the invention are based on relational methods that allow extraction of data to detect the presence or absence and relative amount of a biological molecule, and the location of this molecule in a sample having a distinct structure, e.g., a tissue section or other biological structure with distinct locations of specific biological molecules. The encoding scheme used in these systems corresponds to the structural elements of the sample, and the information obtained using a two-dimensional coding system is indicative of the spatial addresses of these molecules in a sample of interest.

Integral to the assay system of the invention is a method for spatial patterning of reagents. Technologies for formulating and delivering both biological molecules (e.g. DNA or antibodies) and chemical reagents (e.g., small molecules or dNTPs) have already been demonstrated, and use of these systems will be available to one skilled in the art and easily adaptable upon reading this specification.

The assay design of the invention provides an accurate and easily scalable spatial encoding system. The ability to deliver reagents in a spatially defined pattern together with software, reagents and protocols comprises a novel and highly innovative assay system for spatial analysis of various biological molecules and activities. This allows the assays to measure numerous biological functions in a meaningful spatial environment, including functions such as gene expression and peptide localization. The systems provide the potential to open a new analytical window into the complex spatial patterns of cellular function and regulation in biological systems.

The biological molecules to be detected can be any biological molecules such as proteins, nucleic acids, lipids, carbohydrates, ions, or multicomponent complexes containing any of the above. Further examples of subcellular objects include organelles, e.g., mitochondria, Golgi apparatus, endoplasmic reticulum, chloroplast, endocytic vesicle, exocytic vesicles, vacuole, lysosome, etc.

FIG. 4 illustrates such a target-specific assay system for identification of nucleic acid sequences in a sample. In this system, two reagents 420, 422 that specifically bind to a biological molecule of interest are associated with coding identifiers 406, 408 that encode for a spatial location in the sample. These coding identifiers 406, 408 are optionally associated with sites that assist in their identification in the assay format, e.g., universal priming sites 404, 410 for amplification of the assay products or adapters to enable identification of the coding identifiers and the binding agents using sequencing technologies. The sample that is tested, here shown as a tissue section 416 is encoded using the combination of the patterns 412, 414 created using the separate coding identifiers 406, 408 which provide a two dimensional code 418 that shows the location of any positive detection of the biological molecule 402 as well as quantifying the biological molecule 402 at each location assayed in the tissue.

The assay systems of the invention are particularly advantageous in that they are compatible with numerous samples types, such as fresh samples, such as primary tissue sections, and preserved samples including but not limited to frozen samples and paraformalin-fixed, paraffin-embedded (FFPE) samples. An important aspect of the assay systems of the invention is that the binding agents are immobilized on a substrate surface in discrete, independently measureable areas. These discrete areas can be formed by spatially selective deposition of the binding agents on the substrate surface. Numerous methods can be used for the deposition of the agent and the coding identifiers associates with the agent. For example, the coding identifiers can be delivered together or separately from the agent. If delivered together they can be attached (e.g., synthesized as a single molecule or attached through ligation or a chemical coupling mechanism) or simply mixed together to be attached after delivery to the substrate. In a preferred aspect, the agent and the coding identifier are made separately, mixed together for attachment, and delivered either attached or as a mixture to be attached on the surface. In a specific aspect the binding agents are delivered generally over the substrate surface and the coding identifiers are delivered in a pattern-specific manner.

Examples of methods that can be used for deposition of agents and/or coding identifiers onto the substrate surface include, but are not limited to, ink jet spotting, mechanical spotting by means of pin, pen or capillary, micro contact printing, fluidically contacting the measurement areas with the biological or biochemical or synthetic recognition elements upon their supply in parallel or crossed micro channels, upon exposure to pressure differences or to electric or electromagnetic potentials, and photochemical or photolithographic immobilization methods.

For several applications, it may be preferred to arrange the substrates into segments of one or more measurement areas for reagent distribution and agent determination. These regions may be physically separated using barriers or channels. They may still comprise several additional discrete measurement areas with agents that are different or in different combination from each other.

In certain aspects, the present invention provides a method, e.g., a machine-based method, for evaluating changes in the presence and/or location of a biological molecule over time. The method includes providing a plurality of encoded array results representative of the biological molecule over time and evaluating the differences in detection and/or localization of the biological molecules.

Nucleic Acid Detection and Localization

In a particular aspect, the assay system is used to analyze nucleic acids, e.g genotyping, gene expression analysis, localization of particular transcripts within samples, and the like.

Genotyping may be performed using any technique known to those of skill in the art. Preferred techniques permit rapid, accurate determination of multiple variations with a minimum of sample handling. Some examples of suitable techniques involve but are not limited to direct DNA sequencing, capillary electrophoresis, hybridization, allele-specific probes or primers, single-strand conformation polymorphism analysis, nucleic acid arrays, bead arrays, restriction fragment length polymorphism analysis, cleavage fragment length polymorphism analysis, random amplified polymorphic DNA, ligase detection reaction, heteroduplex or fragment analysis, differential sequencing with mass spectrometry, atomic force microscopy, pyrosequencing, FRET (e.g., TaqMan (Applied Biosystems, Inc., Foster City, Calif.) and Molecular Beacon (Stratagene, La Jolla, Calif.) assays), and other related techniques. Several methods for DNA sequencing are well known and generally available in the art. See, for example, Sambrook, et al., Molecular Cloning: A Laboratory Manual (Cold Spring Harbor Laboratory, New York) (2001); Ausubel, et al., Current Protocols in Molecular Biology (John Wiley and Sons, New York) (1997), Twyman, et al. (2003) “Techniques Patents for SNP Genotyping”, Pharmacogenomics 4(1):67-79; and Kristensen, et al. (2001) “High-Throughput Methods for Detection of Genetic Variation”, BioTechniques 30(2):318-332. For details on the use of nucleic acid arrays (DNA chips) for the detection of, for example, SNPs, see U.S. Pat. No. 6,300,063 issued to Lipshultz, et al., and U.S. Pat. No. 5,837,832 to Chee, et al., HuSNP Mapping Assay, reagent kit and user manual, Affymetrix Part No. 90094 (Affymetrix, Santa Clara, Calif.). The molecular inversion probe (MIP) assay format (Hardenbol et al., 2003) is another example of a highly multiplexable assay that may be used with the assay systems of the invention.

In one exemplary and preferred method for analyzing nucleic acids using the assay system of the invention, the detection of nucleic acids uses two allele-specific oligonucleotides and a locus specific oligonucleotide. The assay methods are carried out according to the strategy outlined in FIG. 2 using next-generation sequencing or another highly parallel nucleic acid assay technology. In this assay, a set of two oligonucleotides is designed to hybridize to each target sequence, with a common oligonucleotide and two unique coding identifiers. The allele can be determined, e.g. by primer extension of the locus specific oligonucleotide. Following primer extension and ligation, an amplifiable template is formed with universal primer sequences at either end. Assay oligonucleotides are annealed to a template and enzymatic reactions are used to join the two oligonucleotides only when both are correctly annealed. The detection techniques and read out parameters used in this system of the invention include a much shorter tag than the oligonucleotides used in the assays that are based on capture by hybridization. These shorter tags are designed to be read out by sequencing or, preferably, used to ligate codes onto both ends of the fragment as illustrated in FIG. 2.

In FIG. 3, two target-specific assay oligonucleotides are ligated together 302 following in situ hybridization to target sequences. At the same time, encoding oligonucleotides containing tag sequence sets X and Y are ligated 304 to the target specific oligonucleotides. Oligonucleotides containing X ligate specifically to one side of the targeting construct and oligonucleotides containing Y ligate to the other. The oligonucleotides contain universal primer sites P1 and P2. Following ligation, the constructs are eluted and, optionally, sequencing adapters can be attached 306, e.g., via PCR.

In one preferred aspect, the final construct created from the assay method is a substrate for next-generation sequencing, and highly parallel next-generation sequencing methods are used to confirm the sequence of constructs. Such sequencing methods can be carried out, for example, using a one pass sequencing method or using paired-end sequencing. Next generation sequencing methods include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, and sequencing by synthesis methods, e.g., Nyren et al, U.S. Pat. No. 6,210,891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci., 100: 414-419 (2003); Smith et al, PCT publication WO 2006/074351; use of reversible extension terminators, e.g., Turner, U.S. Pat. No. 6,833,246 and Turner, U.S. Pat. No. 6,833,246 and ligation-based methods, e.g., Shendure et al (2005), Science, 309: 1728-1739, Macevicz, U.S. Pat. No. 6,306,597; which references are incorporated by reference. Soddart et al., PNAS USA. 2009 Apr. 20; Xiao et al., Nat Methods. 2009 March; 6(3):199-201. Epub 2009 Feb. 8.

To maximize the efficiency of encoding, a combinatorial approach using pairs of oligonucleotides can be used. For example, with only two sets of 100 codes, a substrate can theoretically encode up to 10,000 locations. The number of assay oligonucleotides required is dramatically reduced, the cost decreased, and the robustness of the approach increased by decoupling the coding sequences from the genome-specific sequences. Alternative assay formats can also be used (e.g. ligation or primer extension followed by ligation).

By ligating the codes on separately, only 2n target-specific assay oligonucleotides are needed for n targets. For example, assaying 100 different targets at 10,000 spatial locations would require 2×100 targeting oligonucleotides and 2×100 encoding oligonucleotides, using a combinatorial approach outlined in FIG. 2. The total count of assay oligonucleotides would be only 400 (200 target-specific and 200 encoding), not counting universal primers. In contrast, if the coding oligonucleotides were not decoupled, (n×X positional codes)+(n×Y positional codes) would be needed, or in the above example, 20,000 oligonucleotides, not counting universal primer sequences.

Due to the matrix system of the invention, a large amount of information can be obtained even using five or more positions interrogated for five or more biological molecules. By varying one or the other of these, large amounts of information can be obtained, both in terms of locations and/or specific biological In specific aspects, multiple locations are interrogated for two or more biological molecules. As an example, for each datapoint 1,000 reads may be sampled, for a total of −10E9 reads for 10E6 datapoints.

Peptide Detection Systems

The assay system of the invention can be used to analyze biological molecules using peptide agents that are associated with the substrate surface in a spatial pattern. Such peptides may comprise an active region of an enzyme, a binding domain of an immunoglobulin, defined domains of proteins, whole proteins, synthetic peptides, peptides with introduced mutations, etc.

The assay system of the invention allows the identification and spatial location of various forms of peptides, including isoforms and peptides that have undergone post-translational modification. Importantly, certain aspects of the invention allow the identification of active versus non-active forms of such peptides in a sample. This allows the identification of the presence or absence of specific peptide isoforms, and also acts as a proxy for identification of peptide activity in a sample.

In certain aspects of the invention, the binding agents associated with the substrate surfaces of the assay system include substrates for enzymes or proenzymes, e.g., a kinase, a phosphatase, a zymogen, a protease, or a fragment thereof. In certain aspects, the binding agents associated with the substrate surfaces are phosphorylation substrates used to detect proteins involved with one or more signal transduction pathways, e.g., a kinase or a phosphatase. In another specific aspect of the invention, the binding agents are specific protease substrates that associate only with individual or classes of proteases. In other aspects, the binding agents on the substrate surface are different processed forms, isoforms and/or domains of an enzyme.

Reagent Delivery

The reagent delivery system of the invention can be any system that allows the delivery of reagents to discrete portions of the array in order to keep the integrity of the defined spatial patterns of the encoding scheme. Such discrete delivery can be achieved in a number of different ways.

In one exemplary aspect, the reagent delivery system can be a flow-based system. The flow-based systems for reagent delivery in the present invention can include one or more pumps, valves, fluid reservoirs, channels, and/or reagent storage cells. Such a reagent delivery system is configured to move fluid in contact with a discrete section of the substrate surface. Movement of the reagents can be driven through a fluid by a pump disposed, for example, downstream of the fluid reagents. The pump can drive each fluid reagent to (and past) the reaction compartment. Alternatively, the reagents may be driven through the fluid by gravity.

US Appln Nos. 20070166725 and 20050239192 disclose certain general-purpose fluidics tools that can be used with the assay systems of the invention. These allow the precise manipulation of gases, liquids and solids to accomplish very complex analytical manipulations with relatively simple hardware.

In a more specific example, one or more flow-cells can be attached to the substrate from above. The flow-cell can include inlet and outlet tubes connected thereto and optionally an external pump can be used to deliver the sample or reagents to the flow-cell and across the substrate. The flow cell is configured to deliver reagents only to certain portions of the array, restricting the amount and type of reagent delivered to any specific section of the array.

In another aspect, a microfluidic system can be integrated into the substrate or externally attached on top of the substrate. Microfluidic passages for holding and carrying fluid can be formed on and/or above the planar substrate by a fluidics layer abutted to the substrate. Fluid reagents can be selected according to selective opening and closing of valves disposed between reagent reservoirs.

Pumps generally include any mechanism for moving fluid and/or reagents disposed in fluid. In some examples, the pump can be configured to move fluid and/or reagents through passages with small volumes (i.e., microfluidic structures). The pump can operate mechanically by exerting a positive or negative pressure on fluid and/or on a structure carrying fluid, electrically by appropriate application of an electric field(s), or both, among others. Exemplary mechanical pumps may include syringe pumps, peristaltic pumps, rotary pumps, pressurized gas, pipettors, etc. The mechanical pumps may be micromachined, molded, etc. Exemplary electrical pumps can include electrodes and may operate by electrophoresis, electroendoosmosis, electrocapillarity, dielectrophoresis (including traveling wave forms thereof), and/or the like.

Valves generally include any mechanism for regulating the passage of fluid through a channel. The valves can include, for example, deformable members that can be selectively deformed to partially or completely close a channel, a movable projection that can be selectively extended into the channel to partially or completely block the channel, an electrocapillary structure, and/or the like.

In yet another aspect, an open gasket can be attached to the top of the substrate and the sample and reagents can be injected into the gasket. Suitable gasket materials include, but are not limited to, neoprene, nitrile, and silicone rubber. Alternatively, a watertight reaction chamber formed by a gasket sandwiched between the substrate and a chemically inert, water resistant material such as, but not limited to, black-anodized aluminum, thermoplastics (e.g., polystyrene, polycarbonate, etc), glass, etc.

In a specific aspect of the present invention, the delivery system can compnse a microcircuit arrangement including an imager, such as a CCD or IGFET-based (e.g., CMOS-based) imager and an ultrasonic sprayer for reagent delivery such as described in US Appln No. 20090197326, which is incorporated herein by reference.

In yet another aspect of the invention, the reagent delivery system controls the delivery of reagents to specific patterns on a substrate surface using semiconductor techniques such as masking and spraying. Specific areas of a substrate surface can be protected from exposure to reagents through use of a mask to protect specific areas from exposure. The reagents may be introduced to the substrate using conventional techniques such as spraying or fluid flow. The use of the masked substrate delivery results in a patterned delivery scheme on the substrate surface.

In a preferred aspect of the invention, the reagent delivery instrumentation is based on inkjet printing technology. There are a variety of different ink-jetting mechanisms (e.g., thermal, piezoelectric) and compatibility has been shown with aqueous and organic ink formulations. Sets of independently actuated nozzles can be used to deliver multiple reagents at the same time, and very high resolutions can be achieved.

Software for Use in the Assay System

In order to target specific sites of interest, an informative image of the biological section to be analyzed can be used to assist in the reagent delivery methods and associated encoding scheme. Sample regions can be identified using image processing (e.g., images of cell types differentiated by immunohistochemistry or other staining chemistries) integrated with the other features of the assay system. In some aspects, software is used to automatically translate this information into a reagent delivery pattern. A mechanism to register and align very precisely the biological sample in a targeting system is thus a preferred component of the assay systems of the invention. Mechanisms such as the use of fiducial markers on slides and other very accurate physical positioning systems can be adapted to this purpose.

Additional software components will also be key components that will be part of a complete assay system. The invention thus preferably comprises a complete suite of software tailored to the assay system. Optionally, oligonucleotide design software will be customized for the specific assay to be run, and may be integrated as a part of the system. Also optionally, algorithms and software for data analysis may be integrated to assist in determination of results of the assays. This can be especially useful, as the type of dataset that will be generated will be novel, particularly as a consequence of scale. The ability to provide algorithms and software tools that are specifically designed for analysis of spatially-associated data for significant patterns, including pattern-analysis software and visualization tools, is a novel feature that will enhance the value of the data generated by the assay systems.

In certain aspects, the assay system will comprise processes for making and carrying out quality control of reagents, e.g., the integrity and sequence fidelity of oligonucleotide pools. In particular, reagents will need to be formulated for compatibility with the reagent delivery instrumentation. Factors such as volatility, stability at key temperatures, and chemical compatibility can be optimized by those skilled in the art upon reading the present disclosure.

Applications of Assay System

It will be apparent to one skilled in the art upon reading the present disclosure that there are numerous very important areas of biological research, diagnostics, and drug development that will benefit from a high throughput means to simultaneously measure the presence or absence and spatial location of a biological molecule in a sample. For example, this technology combining the ability to analyze semi-quantitatively the expression of many different genes with the ability to image the spatial organization of expression across many cells in a tissue is enabling for many different areas of basic research. The following are exemplary uses and are by no means meant to be limiting in scope.

In one example, 3-dimensional patterns of expression can be determined by analyzing a series of tissue sections, in a manner analogous to image reconstruction in CT scanning. This can be used to measure changes in gene expression in disease pathology, e.g., in cancerous tissue and/or a tissue upon injury, inflammation or infection. With the assay systems of the invention, more detailed information on gene expression and protein localization in complex tissues can be obtained. This may lead to new insights into the function and regulation both in normal and diseased states, and is likely to provide new hypotheses that can be tested. For example, a system of the invention may enable some of the insights gained from many individual studies and larger programs like ENCODE (Birney et al., 2007) and modENCODE to be integrated at the tissue level. The assay systems will also aid in computational efforts to model interacting networks of gene expression in the field of systems biology.

The assay systems also provide a novel approach that enables the analysis of somatic variation, e.g., somatic mutations in cancer or variability in response to infectious organisms. For example, tumors are typically highly heterogeneous, containing cancer cells as well as genetically normal cells in an abnormal local environment. Cancer cells undergo mutation and selection, and in this process it is not unusual for local clones to develop. Identifying relatively rare somatic mutations in the context of tumors may enable the study of the role of key mutations in the selection of clonal variants. Transcriptional patterns associated with angiogenesis, inflammation, or other cancer related processes in both cancer and genetically normal cells can be analyzed for insights into cancer biology and assist in the development of new therapeutic agents for the treatment of cancers.

In another example, different people have varying susceptibility to infectious organisms, and much of this may be to underlying genetic differences in individuals and/or populations. Identifying these differences will aid in an understanding of the underlying disease pathologies and assist in the development of vaccines or therapeutics to prevent or ameliorate these disease states.

Importantly, in addition to providing spatially associated information, the technology of the invention will allow a great increase in the sensitivity of detecting rare mutations. The reason is that signal to noise can be dramatically increased because the approach of the invention assays a small location in any given reaction. In a typical assay for rare mutations in a mixed sample, the sample is treated in bulk, i.e. nucleic acids are extracted from many cells into a single pool. Thus, if a mutation is present in 1 cell in 10,000, it must be detected against a background of normal DNA from 10,000 cells. In contrast, with the systems of the invention many cells can be analyzed, but individual cells or small groups of cells would be identified by the spatial coding system. Therefore, the background can be reduced by orders of magnitude, greatly increasing sensitivity. Furthermore, the spatial organization of mutant cells can be observed. This may be particularly important in detecting key mutations in tissue sections in cancer. Already, molecular histological analyses are yielding insights into cancer biology and may have potential for use in diagnostics (Choe et al., 2003). The technology of the invention promises to greatly increase the power of such approaches.

EXAMPLES

The following examples are put forth so as to provide those of ordinary skill in the art with a complete disclosure and description of how to make and use the present invention, and are not intended to limit the scope of what the inventor regards as his invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: Initial Proof of Concept of Encoding Scheme

As an initial proof of concept, a model system is developed using a microarray to demonstrate a working singleplex assay. The basic design validates the concept of the assay, and establishes a working assay prior to addressing issues related to the analysis of a more complicated biological sample. Conventional sequencing is used as a readout for this proof of concept.

A microarray is used as a proxy for a tissue section. The target sequences of the microarray are fully specified, so that the composition of the targets are known and can be varied systematically. Synthetic oligonucleotide templates are attached to a glass slide via a 5' amino modification. Each slide has a single oligonucleotide template sequence, and the assays that are carried out may employ either ligation, or extension followed by ligation as this may be useful in determining certain polymorphisms.

Once the in situ part of the assay is complete, the reaction products are eluted and analyzed by qPCR to determined presence or absence of a product and estimate yield, and by conventional sequencing to determine the structure of the assay products. The single plex assays that are tested include appropriate positive and negative controls, and a single nucleotide variant (SNV) to check ability to discriminate single base variants.

Example 2: Scalability

The complexity of the assay system is increased to establish scalability of the assay for use in high throughput studies. Scalability of both the spatial encoding and assay systems is demonstrated by carrying out a 24-plex×24-site assay using a microarray model system.

The amount of biological target, here a DNA target sequence, at each assay location is systematically varied on microarray substrate. For example, in a microarray with 50 micron spot size (center to center), a 1 $mm^2$ area contains ~400 spots. The region around each site is optionally occupied by a region that is devoid of these spots to allow individual resolvability of the target sequences. Alternatively, the spots may be clustered, with two or more directly adjacent spots surrounded by or adjacent to a region that is devoid of target sequences.

In order to demonstrate that spatial encoding is accurate, the sites comprise different target compositions to show that the assay readout matches the expected composition of each site. With 24 target sequences, a simple digital pattern is made with each site having a different set of 12 targets present and 12 targets absent, to make a binary code (0=absent, 1=present). The assay readout is then determined to show that the detected regions match the expected signal after spatial decoding. In this particular example, the code space is large enough ($2^{24}$) so that even a few errors would not result in different codes being mixed up. Moreover, this design allows identification of errors and allows an estimation not only of accuracy of spatial encoding but also of accuracy calling the presence or absence of target sequences.

In an exemplary aspect, a 4×4 arrangement of 16 sequences is used for the array configuration. A white square indicates that the sequence is absent and a black square that it is present, i.e. 8 of the 16 possible sequences are present in this sample. In a different sample, a different pattern of absent and present sequences can be constructed. In this way, unique patterns are associated with spatial locations so that the accuracy of spatial encoding can be measured.

The ability to detect quantitative differences is evaluated by generating dose-response curves for each of the 24 assays that are carried out at each site in a 24-site assay. This allows estimation of the limit of detection, dynamic range, and power to detect a given fold-change across the range.

In one aspect, a latin square design is used to represent individual targets at different ratios by varying the number of features for each target. In other words, with multiple spots in a site, the number of spots allocated to each of the 24 target sequences can be varied and each of the 24 sites can have a different composition. A 1×3 inch microarray is sufficiently large to permit multiple replicates. This larger set of 24 sequences will require deconvolution, and this is accomplished using high throughput techniques such as next-generation sequencing technologies (e.g., SOLiD™ technology (Life Technologies, Inc., Carlsbad, CA) or Genome Analyzer (Illumina, Inc., San Diego, CA)). The use of the 24-plex assay demonstrates both the accuracy of spatial encoding and decoding, and the quantitative response of the assay system.

Example 3: Adaptation of the Assay to Preserved Samples

Genomic DNA is assayed as a proof of concept for assaying RNA, as it provides a way to establish a single-copy reference signal. Once a working assay is developed for FFPE samples, it is adapted to an RNA assay. To this end, assay oligonucleotide concentrations are assayed to ensure compatibility with high multiplexing. Assuming a cell diameter of 10 microns, and delivery of a 10 micron diameter reagent droplet to an individual cell, the volume of the droplet will be ~500 μl and can contain ~$3\times10^{11}$ molecules at a 1 μM concentration. To assay 1,000 target sequences in 10,000 cells, 2,000 targeting oligonucleotides would be required in a droplet. Therefore, each droplet could contain ~160 million copies of each assay oligo, a vast excess over the few thousand target sequences in a cell.

The handling of small absolute numbers of product molecules generated from very small or compromised samples are enhanced to counter the issue of low recovery efficiency; that is, elution is efficient and losses resulting from adsorption of molecules to surfaces are prevented. An approach to addressing the latter issue is to include a carrier material, such as glycogen or carrier nucleic acids.

Example 4: Adapting the Assay to a Biological Sample

A control RNA template is immobilized to a solid support in order to create an artificial system. The assay is performed using T4 DNA ligase, which can repair nicks in DNA/RNA hybrids. Assays are carried out on matched slides, or different sections of the same slide, where in one case gDNA is assayed and in the other RNA is assayed. When assaying gDNA the slide can be pretreated with RNase, and when assaying RNA the slide is pretreated with DNase. Results of the assay are confirmed by extracting gDNA or RNA and quantitating the relative amounts by qPCR or RT-qPCR respectively.

In order make the tissue section RNA assays as informative as possible, pre-existing information on expression levels in specific tissues to target transcripts across a range of abundances are used in the assay design. Both high abundance transcripts, as well as some medium and low abundance transcripts, are targeted to enable an initial assessment of the quantitative performance characteristics of the assay.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶6.

The invention claimed is:

1. A method of detecting a mitochondrial DNA at a location in a biological sample comprising:

(a) contacting the biological sample comprising mitochondrial DNA with a first probe and a second probe, wherein:

the first probe comprises a first sequence that hybridizes to a first portion of the mitochondrial DNA and a first universal priming site;

the second probe comprises a second sequence that hybridizes to a second portion of the mitochondrial DNA and a second universal priming site;

the first probe and the second probe hybridized to the mitochondrial DNA are capable of being ligated together; and one or both of: (i) the first probe further comprises a nucleic acid sequence identifying the location to where the first probe was delivered and (ii) the second probe further comprises a nucleic acid sequence identifying the location to where the second probe was delivered;

(b) ligating the first probe and the second probe together to generate a ligation product;

(c) amplifying the ligation product using a first amplification primer that is capable of hybridizing to the first universal priming site, and a second amplification primer that is capable of hybridizing to the second universal priming site, to produce an amplification product; and (d) determining all or a portion of the sequence of the amplification product or a complement thereof, and using the determined sequence to detect the mitochondrial DNA at the location in the biological sample.

2. The method of claim 1, wherein the ligating in step (b) comprises the use of a ligase.

3. The method of claim 2, wherein the ligase is T4 DNA ligase.

4. The method of claim 1, wherein the method further comprises the use of one or both of an RNase and a protease.

5. The method of claim 1, wherein the method further comprises, between steps (a) and (c), washing away the first probe and the second probe not hybridized to the mitochondrial DNA.

6. The method of claim 1, wherein the amplifying in step (c) comprises the use of a DNA polymerase.

7. The method of claim 1, wherein step (d) comprises sequencing all or a portion of the sequence of the amplification product or a complement thereof.

8. The method of claim 7, wherein the sequencing is high-throughput sequencing.

9. The method of claim 8, wherein the high-throughput sequencing is digital nucleic acid sequencing or sequencing-by-ligation.

10. The method of claim 1, wherein the biological sample is affixed to a support.

11. The method of claim 10, wherein the support is a slide or a culture dish.

12. The method of claim 1, wherein the biological sample is a tissue sample.

13. The method of claim 12, wherein the tissue sample is a tissue section.

14. The method of claim 13, wherein the tissue section is a fresh, frozen tissue section.

15. The method of claim 13, wherein the tissue section is a fixed tissue section.

16. The method of claim 15, wherein the fixed tissue section is a formalin-fixed, paraffin-embedded (FFPE) tissue section.

17. The method of claim 1, wherein:

the biological sample further comprises a second mitochondrial DNA at a different location in the biological sample;

step (a) further comprises contacting the biological sample with a third probe and a fourth probe, wherein:

the third probe comprises a first sequence that hybridizes to a first portion of the second mitochondrial DNA and the first universal priming site;

the fourth probe comprises a second sequence that hybridizes to a second portion of the second mitochondrial DNA and the second universal priming site;

the third probe and the fourth probe hybridized to the second mitochondrial DNA are capable of being ligated together; and one or both of: (i) the third probe further comprises a nucleic acid sequence identifying the location to where the third probe was delivered and (ii) the fourth probe further comprises a nucleic acid sequence identifying the location to where the fourth probe was delivered;

step (b) further comprises ligating the third probe and the fourth probe together to generate a second ligation product;

step (c) further comprises amplifying the second ligation product using the first amplification primer and the second amplification primer to produce a second amplification product; and step (d) further comprises determining all or a portion of the sequence of the second amplification product or a complement thereof, and using the determined sequence to detect the second mitochondrial DNA at a location in the biological sample.

18. The method of claim 17, wherein the method further comprises, between steps (a) and (c), washing away the third probe and the fourth probe not hybridized to the second mitochondrial DNA.

19. The method of claim 17, wherein step (d) comprises sequencing all or a portion of the sequence of the second amplification product or a complement thereof.

20. The method of claim 19, wherein the sequencing is high-throughput sequencing.

* * * * *